United States Patent [19]

Bussler et al.

[11] Patent Number: 5,484,760
[45] Date of Patent: Jan. 16, 1996

[54] HERBICIDE ANTIDOTES AS SAFENERS FOR REDUCING PHYTOTOXICITY RESULTING FROM SYNERGISTIC INTERACTION BETWEEN HERBICIDES AND OTHER PESTICIDES

[75] Inventors: Brett H. Bussler, St. Louis Park, Minn.; Harrison R. Hakes, Ballwin; David J. Mayonado, Chesterfield, both of Mo.

[73] Assignee: Monsanto Company, St. Louis, Mo.

[21] Appl. No.: 808,590

[22] Filed: Dec. 20, 1991

Related U.S. Application Data

[63] Continuation-in-part of Ser. No. 636,360, Dec. 31, 1990, abandoned.

[51] Int. Cl.$^6$ .................................................. A01N 25/32
[52] U.S. Cl. .................... 504/103; 504/104; 504/105; 504/106; 504/107; 504/108; 504/109; 504/110; 504/111; 504/112
[58] Field of Search ........................ 71/92, 88; 514/144; 504/103, 104, 105, 106, 107, 108, 109, 110, 111, 112; A01N 25/32

[56] References Cited

U.S. PATENT DOCUMENTS

| | | | |
|---|---|---|---|
| 3,989,503 | 11/1976 | Pallos et al. | 71/88 |
| 4,021,224 | 5/1977 | Pallos et al. | 71/88 |
| 4,915,725 | 4/1990 | Hyzak et al. | 71/87 |
| 4,936,901 | 6/1990 | Surgant et al. | 71/92 |
| 4,956,129 | 9/1990 | Scher et al. | 264/4.7 |
| 5,049,182 | 9/1991 | Scher et al. | 71/93 |
| 5,143,539 | 9/1992 | Lovell | 71/92 |
| 5,397,765 | 3/1995 | Cary | 504/110 |

FOREIGN PATENT DOCUMENTS

| | | |
|---|---|---|
| 0304409 | 2/1989 | European Pat. Off. . |
| 0312763 | 4/1989 | European Pat. Off. . |
| 0524394 | 1/1993 | European Pat. Off. . |

OTHER PUBLICATIONS

Ogawa, Y., et al., CAS 111:189595X, Abst. of JP 01,110, 604, Apr. 27, 1989, Abst. from JPO ABS attached.

Kimura et al., CAS 112:172972c "56–950, A Novel Sulfonylurea Herbicide for Corn", Brighton Crop. Prot. Conf.–Weeds, 1989.

Can. J. Plant Sci. 58:1119–1121 (Oct. 1978), "Evidence . . . Corn".

*Primary Examiner*—S. Mark Clardy
*Attorney, Agent, or Firm*—William I. Andress; Grace L. Bonner; Richard H. Shear

[57] ABSTRACT

The disclosure herein relates to means for combatting the adverse phytotoxic action to crops arising from the interaction of various herbicidal compounds and biocidal compounds, e.g., insecticidal and/or fungicidal compounds. The means employed to reduce said interaction involves the safening action of various antidotal compounds.

25 Claims, No Drawings

1

HERBICIDE ANTIDOTES AS SAFENERS FOR REDUCING PHYTOTOXICITY RESULTING FROM SYNERGISTIC INTERACTION BETWEEN HERBICIDES AND OTHER PESTICIDES

This is a Continuation-In-Part of Ser. No. 07/636,360, filed Dec. 31, 1990 now abandoned.

FIELD OF THE INVENTION

The field of the invention contemplated herein pertains to the safening of enhanced herbicidal phytotoxicity induced by the interaction with various biocides, especially insecticides. The safening action is effected by the presence of various antidotal (safener) compounds.

BACKGROUND OF THE INVENTION

It is a common practice in agricultural practice to apply herbicidal compositions to control undesirable vegetation in cultivated crops. Such herbicidal compositions may contain other additaments such as fertilizers, biocides, e.g., insecticides, fungicides, nematicides, etc., herbicide antidotes, etc.

Additional agricultural practices include the application of said herbicidal compositions to soils or vegetation previously treated with said biocides. However, a long history of experience with focused attention developing in the early 1960s has shown that major problems can arise as a result of the interaction of herbicides and various biocides, particularly various insecticides and/or fungicides. The common result of such interaction is the enhancement of the phytoxic activity of the herbicide in various crops. This enhanced phytotoxicity is referred to in the literature and will be so used herein as "negative synergy/synergism" between the herbicide(s) and the biocide(s). Such negative synergism is expressed in terms of decreased emergence of a crop, reduced crop survival or vigor, crop stand reduction and/or crop yield.

The herbicides and biocides giving rise to negative synergy when in contact with each other have been found to include members from a variety of classes, including, but not limited to, in the case of herbicides, sulfonylureas, imidazolinones, aliphatic and aromatic carboxylic acids, amides salts and esters, isoxazolidinones, ureas, triazines, thiocarbamates, acetanilides, etc., etc. In the case of insecticides, organic phosphates ("organophosphates" or "OPs"), carbamates, pyrethroids, cyclopropanecarboxylic acid esters, carboxamides, dicarboximides, perchlorocyclohane, etc.

Negative synergism has been found to occur between herbicides and insecticides in a variety of crops including small grain crops, narrow leaf crops, e.g., corn, rice, barley, sorghum, wheat and broadleaf crops such as cotton, soybeans and sugarbeets.

Illustrative examples of the phenomenon of negative synergism from the literature are plentiful and readily available and typical ones are cited here. For example, Walter et al, Texas Agricultural Experiment Station Progress Report 2284 (1963) and J. Hacskaylo et al Weeds 2:88–291 (1964) reported injury to cotton seedlings following use of combinations of monuron or diuron herbicides and phorate (also known as thimet) or disulfoton systemic insecticides. Schweizer and Ranney reported on interactions among EPTC plus diuron and trifluralin herbicides and captan-terrachlor fungicide and phorate on cotton. Mississippi Agr. Exp. Sta. Information Sheet 877 (1965).

A series of studies in 1966–1969 by A. Y. Chambers et al reported in Proc. SWSS, 21:54–66 (1966) and 83–92 (1969) and Tennessee Farm and Home Science, 66:13–15 (1968), summarized work initiated at the University of Tennessee West Tennessee Experiment Station to evaluate cotton herbicides for interactions when applied with soil fungicides and systemic insecticides. The studies reported by Chambers et al involved a variety of types of pesticides, including as herbicides fluometuron, diuron and norea ureas; CIPC (a carbamate); DCPA (a terephthalate); prometryne (a triazine); trifluralin (a dinitrotoluidine) and nitralin (an aniline) and as fungicides, captan plus terrachlor plus terrazole and as insecticides, disulfoton with and without phorate. In these studies Chambers et al observed significant interactions between the pesticides, with many combinations of pesticides giving a variety of negative synergistic effects, including reduction in seedling emergence, significant reduced cotton seedling survival and/or vigor and/or stand reduction and/or yield.

Reports by H. W. Ivy et al in Proc. SWSS, p. 94, 1969 and p. 132, 1973 cite a variety of pesticide interactions with the same herbicides used by Chambers et al; chloroneb or PCNB with or without Terrazole fungicides and phorate, disulfoton and UC-21149 (aldecarb) insecticides. Various combinations resulted in negative synergism in cotton.

In Proc. SWSS-95, 1969, B. J. Johnson reported negative synergism in terms of significantly reduced seedling vigor in soybeans due to the interaction of various combinations of Amiben ethyl ester, trifluralin and linuron herbicides and methomyl and phorate insecticides.

R. M. Hayes et al reported that use of non-recommended rates of the herbicide metribuzin and the insecticides disulfoton and phorate resulted in significant reductions in yield and stand reductions of two varieties of soybeans. Proc. SWSS-1976 p. 95.

More recently, C. D. Applewhite reported (Proc. SWSS, p. 83, 1990) on tests in cotton with various application modes (granular in-furrow or tank spray) of clomazone with and without fluometuron herbicides in combination with the OP insecticides disulfoton, phorate, aldecarb and acephate and the nematicide fenamiphos. A number of combinations of these chemicals and application modes gave a variety of responses ranging from the safening of clomazone by the interaction of disulfoton and phorate applied in-furrow as granular formulations, but accompanied by some plant discoloration and a 7% stand reduction; no effect on safening by fenamiphos, but producing the same plant discoloration and stand reduction as the OP insecticides. Applied as in-furrow sprays at various rates, disulfoton safened clomazone, but gave 5% discoloration and stand reduction, whereas without the safening, fenamiphos and acephate gave the same discoloration and stand reduction.

Applewhite further reported that combinations of clomazone alone or with fluometuron applied PPI or PRE at different rates to aldecarb or phorate resulted in no adverse reactions. However, at lower rates aldecarb applied in-furrow failed to reduce cotton discoloration and stand reduction.

In a recent technical bulletin dated Sep. 5, 1990 to its dealers, the proprietary owner of the sulfonylurea herbicide, ACCENT® (common name "nicosulfuron") cautioned that COUNTER® soil insecticide (an OP) can react with ACCENT, resulting in damage to corn. Thus, the ACCENT label prohibits the use of that product if COUNTER has been applied as a soil insecticide. The recommendation is to use alternative soil insecticides (but none are specified).

In a similar technical bulletin dated Oct. 23, 1990 to its dealers, the proprietor of BEACON® (common name "primisulfuron") herbicide, also a sulfonylurea herbicide, stated that: "Extensive field tests and scientific research shows that when COUNTER is present in the corn plant, an application of a sulfonylurea herbicide like BEACON often can cause injury to the corn plant. The chemistry in COUNTER slows the metabolism of the plant, which interferes with the detoxification process . . . we have conducted extensive lab and field tests, independently and in cooperation with American Cyanamid, to discover ways to avoid this negative synergy. We've examined application timing and methods and various Counter formulations—including COUNTER 20 CR—but to date there is no reliable solution to this problem . . . . The Beacon label for 1991 will continue to prohibit use of BEACON whenever COUNTER has been applied . . . growers have other options to control troublesome insects." (Underlines in cited document).

In an article in the Canadian Journal of Plant Science, Vol. 58, pp. 1119–1121 (October, 1978), numerous citations are made to studies resulting in findings of negative synergism between various herbicides and insecticides in various crops, including corn injury by the interaction of Eradicane and fonofos.

In the study reported in said article, the authors evaluated the effect on corn of applications of the insecticide fonofos on the herbicides EPTC and vernolate containing the antidote dichlormid (i.e., Eradicane and Surpass, respectively). In tests in succeeding years (1976 and 1977) the authors found no negative synergy between fonofos and the herbicides containing the antidote in 1976, but in 1977 found severe damage to corn ear quality and reduction in tiller numbers, albeit insignificant, by Eradicane plus fonofos. The 1977 results confirmed reports by some growers in 1975. No negative synergy was found between the Surpass plus fonofos treatments in either of the two-year trials.

The authors concluded that negative synergy with these herbicides and fonofos in corn can be inconsistent from year to year, possibly because of soil and weather conditions. It is noteworthy that the authors did not even discuss, much less recognize, any significance in the presence of the antidote dichlormid— which in their 1977 tests did not prevent corn injury. Nor did the authors comment on the fact that the particular combination of vernolate plus dichlormid caused no injury to corn, with or without fonophos, an inference, therefore, that vernolate and fonophos may not induce negative synergism.

On the other hand, in tests with fonofos and other soil-insecticides, e.g., terbufos, chlorpyrifos and thimet, with another herbicide, the sulfonylurea nicosulfuron (active ingredient in Accent® herbicide), in corn Drs. H. Wilson at VIP & SU and F. Webb, University of Delaware, found negative synergism in all treatments (in-furrow, T-band, side-band and surface band applications).

It is seen from the literature that various postulates have been advanced to explain the basis for the noted negative synergy between various herbicides and biocides, especially OP systemic insecticides, in various crops. Thus, Hayes et al, supra, point to use of off-recommended rates of the pesticides. The above-mentioned technical bulletin regarding BEACON herbicide points to interruption of plant metabolism leading to detoxification thereof.

A variety of solutions have been proposed to avoid the negative synergy problem. Thus, Chambers et al, supra, concentrated on intensive evaluations of combinations of preemergence herbicides, systemic insecticides and soil fungicides in cotton. Still other proposed solutions to the problem include the avoidance of tank mixing the herbicide and biocide or delaying the application for many days or weeks after the biocide has been applied to the soil. Various workers have proposed formulating the biocide as a controlled release ("CR") formulation. Both of the above technical bulletins concerning ACCENT and BEACON herbicides solve the negative synergy problem by avoiding it, i.e., prohibit use of those herbicides, both sulfonylureas, when the soil insecticide COUNTER, has been used.

It is, therefore, an object of this invention to minimize, reduce or eliminate negative synergy arising from the interaction of herbicides and biocides. Particular embodiments of the invention refer to the use of herbicides which exhibit ALS inhibitory action in weed plants, especially sulfonylurea, imidazolidinones, azolopyrimidine sulfonamides, and the like. However, other herbicides not included in the foregoing classes of compounds have also exhibited negative synergy with biocides, even though such other herbicides, e.g., acetamides, thiocarbamates, etc., are not known to be ALS inhibitors, but do exhibit a similar mode of inhibitory action.

SUMMARY OF THE INVENTION

In one aspect, the present invention relates to compositions comprising: (a) a herbicidal component; (b) a biocidal component and (c) an antidotal component, which latter component inhibits, reduces or prevents the tendency to interact or the actual interaction of the former two components to enhance the phytotoxicity of said herbicidal component. Such enhanced phytotoxicity is defined as "negative synergy or synergism".

In another aspect, this invention relates to a method for combatting, inhibiting, reducing or preventing negative synergism resulting from the interaction of herbicidal and biocidal compounds by use of an antidotal compound.

In preferred embodiments, the herbicidal component is a compound which causes an ALS inhibition reaction in plants. By "ALS inhibition" is meant that the effect of the herbicide on the plant is to interrupt or inhibit the aceto lactate synthase ("ALS") enzyme in the amino acid pathway leading to plant proteins. Compounds known to exhibit such ALS inhibitory reaction in plants include sulfonylureas, imidazolinones and azolopyrimidine sulfonamides.

Other herbicidal compounds which cause negative synergy, either through an ALS or non-ALS or some other form of inhibitory action in weed plants include α-haloacetamides, thiocarbamates, aliphatic and aromatic carboxylic acids, amides, salts and esters, isoxazolidinones, ureas, triazines, nitrobenzenes, etc.

In more particular, preferred herbicidal compounds useful in the present invention are selected from azolopyrimidine sulfonamide, sulfonylurea, imidazoline, acetanilide and thiocarbamate compounds more particularly defined below.

preferred azolopyrimidine sulfonamide compounds useful herein include those according to Formula I or agriculturally-acceptable salts thereof:

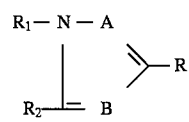

wherein A and B are independently N or $CR_3$, provided that at least one of A or B is N;

R is —N(R$_4$)SO$_2$R$_5$ or —SO$_2$N(R$_6$)R$_7$;

R$_1$ is hydrogen, alkyl, alkenyl, alkynyl, acyl, acyloxy, cycloalkyl, cycloalkenyl, aryl, aralkyl, alkoxy, alkoxyalkyl, alkoxycarbonyl, aminocarbonyl, alkylsulfinyl, alkylsulfonyl or heterocyclic group or where not self inclusive any of these non-hydrogen radicals substituted with cyano, halogen, amino, mono- or di- C$_{1-4}$ alkyl amino, C$_{1-6}$ alkyl, haloalkyl, alkylthio, alkoxy, alkoxyalkyl, alkoxycarbonyl, alkylthio, alkylsulphinyl or alkylsulfonyl;

R$_2$ is an R$_1$ member, halogen, cyano, amino, mono- or di-C$_{1-4}$ alkyl amino, pyrrolyl or pyrrolyl substituted with halogen, cyano, amino C$_{1-4}$ alkyl or alkoxy;

R$_1$ and R$_2$ may be combined to form a divalent group which together with the N and C atoms to which they are respectively attached form a heterocyclic ring fused with the azolo ring, said heterocyclic ring containing up to 10 ring members of which up to 4 may be N, S and/or O atoms and having saturated and/or unsaturated bonds;

R$_3$ is an R$_2$ member or NO$_2$, S(O)$_n$C$_{1-4}$ alkyl, where n is an integer 0, 1, 2 or 3, C(O)R$_8$, phenyl, phenoxy, phenylthio, or these phenyl, phenoxy or phenylthio members substituted with from 1 to 4 halogen, CN, CF$_3$, NO$_2$ and/or C$_{1-4}$ alkyl or alkoxy members; R$_8$ is C$_{1-6}$ alkyl, haloalkyl, alkylthio, alkoxy, alkoxyalkyl, amino, mono- or di-C$_{1-4}$ alkylamino, phenyl or an R$_3$ phenyl-substituted member;

R$_4$ and R$_6$ are independently H or alkyl, acyl, alkenyl, alkenyloxy, alkenyloxycarbonyl, alkynyl, alkynyloxy, alkanoyl, alkoxy, haloalkoxy, haloalkylthio, alkoxyalkyl, alkoxycarbonyl, or alkoxythiocarbonyl, each having up to 10 carbon atoms; phenyl, benzyl, naphthylphenylthio, phenoxy, phenoxythio, phenoxycarbonyl, phenyl S(O)$_n$; phenyl S(O)$_n$C$_{1-4}$ alkyl; phenyl S(O)$_n$C$_m$(K)$_{2m}$H; phenyl S(O)$_n$CK$_3$, where n is 0, 1, 2 or 3, m is 1-3 and K is halogen; phenoxy- carbonyl, phenoxythiocarbonyl, aminocarbonyl, or where not self-inclusive said R$_4$ and R$_6$ members substituted with halogen, CN, CF$_3$, NO$_2$, OH and/or C$_{1-10}$ alkyl, haloalkyl, alkoxy, alkoxy- alkoxy, hydroxyalkoxy, alkylthioalkoxy, alkoxycarbonyl, or polyalkoxycarbonyl, phenyl, halophenyl, benzyl, benzyloxy, phenoxyalkoxy and agriculturally-acceptable salts thereof when R$_4$ and R$_6$ are H and R$_5$ and R$_7$ are independently an aromatic hydrocarbon or heterocyclic radical having up to 10 ring members of which up to four may be N, O and/or S in the heterocyclic radical and said R$_5$ and R$_7$ members substituted with one or more R$_4$ members, 2-pyridyl, 2-pyridyloxy or 2-pyridylmethoxycarbonyl, dialkylaminoalkoxycarbonyl having up to 10 carbon atoms and the radical C(O)ON=C(R$_9$)$_2$, wherein R$_9$ is H, phenyl, phenylcarbonyl, benzyl, C$_{1-10}$ alkyl, alkoxy, mono- or di-C$_{1-6}$ alkylamino or -alkylaminocarbonyl, —S(O)$_n$R$_{10}$, where n is 0, 1, 2 or 3 and R$_{10}$ is C$_{1-6}$ alkyl, haloalkyl, mono- or di-C$_{1-4}$ alkylamino or alkylcarbonyl, said compound of Formula I being used alone or in admixture with other known herbicidal compounds as co-herbicides, preferably an α-haloacetamide as defined hereinafter.

Preferred herbicidal compounds according to Formula I are those wherein A and B are both nitrogen; R is —SO$_2$N(R$_6$)(R$_7$); R$_1$ is phenyl, pyrimidinyl, triazinyl, thiadiazolyl, pyrazinyl, pyridinyl, or any of said R$_1$ radicals substituted with cyano, halogen, amino, mono- or di-C$_{1-4}$ alkylamino, C$_{1-6}$ alkyl, haloalkyl, alkylthio, alkoxy, alkoxyalkyl, alkoxycarbonyl, alkylthio, alkylsulfinyl or alkylsulfonyl; R$_2$ is hydrogen, halogen, cyano, amino, mono- or di-C$_{1-4}$ alkylamino, C$_{1-6}$ alkyl, alkylsulfinyl, alkylsulfonyl, alkoxy, alkoxyalkyl, alkoxycarbonyl, acyl, acyloxy or pyrrolyl optionally substituted with C$_{1-4}$ alkyl; R$_6$ is hydrogen, C$_{1-4}$ alkyl, acyl, alkylsulfonyl, alkoxy, alkoxycarbonyl, dialkyl-carbamoyl or benzyl and R$_7$ is furyl, thiophene or phenyl or those radicals substituted independently with one or more C$_{1-4}$ alkyl, haloalkyl, alkoxy, alkoxyalkyl, haloalkoxyalkyl, alkenyl, alkenyloxy, alkynyloxy, alkylsulfinyl, alkylsulfonyl, alkoxycarbonyl, mono- or dialkylamino, amino, or nitro groups.

In the above embodiment of the invention, preferred species include N-(2,6-dichloro-3-methyl-phenyl)- 1-(4-chloro-6-methoxypyrimidinyl-2-yl)-1H- 1,2,4-triazole-3-sulphonamide; N-(2,6-difluorophenyl)-1-(pyrimidin-2-yl)-5-methyl-1,2,4-triazole-3-sulphonamide; N-(2,6-dichloro-3-methylphenyl)-1(pyrimidin-2-yl)-5-methyl-1,2,4-triazole-3-sulphonamide; N-(2-methyl- 6-nitrophenyl)-1-pyrimidin-2-yl)-5-methyl-1,2,4-triazole- 3-sulphonamide; N-(2,6-difluorophenyl)-1-(4,6-dimethylpyrimidin- 2-yl)-5-methyl-1,2,4-triazole-3-sulphonamide; N-(2,6-dichlorophenyl)-1-pyrimidin-2-yl)-5-methyl-1,2,4-triazole-3-sulphonamide; N-(2,6-difluorophenyl)- 1-(4-methylpyrimidin-2-yl)-5-methyl-1,2,4-triazole-3-sulphonamide; N-(2,6-difluorophenyl)-1-(4-methoxy-6-methylpyrimidin-2-yl)-5-methyl-1,2, 4-triazole-3-sulphonamide; N-(2,6-dichlorophenyl)-1-(4,6-dimethoxy-1,3,5-triazin-2-yl)-5-methyl-1,2,4-triazole- 3-sulphonamide; N-(2,6-dichlorophenyl)-1-(4,6-dimethylpyrimidin- 2-yl)-1,2,4-triazole-3-sulphonamide; N-(2,6-dichlorophenyl)-1-(4,6-dimethylpyrimidin-2-yl)-5-methyl-1,2,4-triazole-3-sulphonamide; N-(2-methyl-6-nitrophenyl)- 1-(4,6-dimethylpyrimidin-2-yl)-5-methyl-1,2, 4-triazole-3-sulphonamide; N-(2,6-dichlorophenyl)- 5-(2,5-dimethylpyrrol-1-yl)-1,2,4-triazole-3-sulphonamide; N-(2, 6-difluorophenyl)-5-(2,5-dimethylpyrrol-1-yl)- 1,2,4-triazole-3-sulphonamide; N-(2,6-dichloro-3-methyl-phenyl)- 1-(4,6-dimethylpyrimidin-2-yl)-1,2,4-triazole-3-sulphonamide; N-(2,6-dichloro-3-methylphenyl)-5-amino-1-( 4,6-dimethylpyrimidin-2-yl)-1,2,4-triazole-3-sulphonamide; or N-(2,6-dichloro-3-methylphenyl)-5-amino-1-(4,6-dimethoxy-1,3,5-triazin-2-yl)-1,2,4-triazole- 3-sulphonamide.

In other embodiments of the invention, more preferred herbicidal compounds according to Formula I are those wherein A and B are both nitrogen (N), R is —SO$_2$N(R$_6$)(R$_7$) and R$_1$ and R$_2$ are combined to form one of the following divalent radicals:

(a)

(b)

(c)

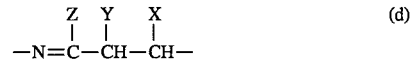

(d)

(e)

(f)

-continued

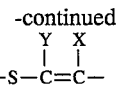

wherein $R_6$ and $R_7$ are as defined above and X, Y and Z are independently an $R_4$ member, $SO_2$, or adjacent X and Y or Y and Z members may be combined to form a saturated, partially unsaturated or unsaturated homocyclic ring or heterocyclic ring containing up to 10 ring members of which up to 4 may be oxygen, sulfur and/or N and D is oxygen or sulfur.

Preferred compounds containing the above divalent structures are those wherein $R_6$ is hydrogen, alkyl, alkenyl, alkoxy, alkoxycarbonyl, alkoxythiocarbonyl, alkylsulfinyl or alkylsulfonyl having up to 6 carbon atoms; amino, mono- or di-$C_{1-4}$ alkylamino or —alkylaminocarbonyl; phenyl, benzyl, benzoyl or an $R_6$ member when not self-inclusive substituted with one or more halogen, nitro, $C_{1-4}$ alkyl, haloalkyl or alkoxy radicals; $R_7$ is unsubstituted phenyl or pyrazolyl or optionally substituted independently with one or more phenyl, halogen, nitro, trifluoromethyl, $C_{1-6}$ alkyl, alkoxy, alkoxyalkyl, alkoxycarbonyl, —$S(O)_n$ alkyl, —$S(O)_nC_m(K)_{2m}H$, —$S(O)_nCK_3$, amino, carbamyl, mono- or di- $C_{1-4}$ alkylamino or -alkyl carbamyl; X, Y and Z are independently hydrogen, halogen, $C_{1-4}$ alkyl, haloalkyl, alkoxy, alkylthio or alkylsulfonyl, preferably substituted in one meta position and one or both ortho positions; m and n are integers from 0–3 inclusive and K is halogen.

Among preferred species of compounds wherein $R_1$ and $R_2$ are combined to form the bivalent radical (a) above, its tetrahydro analogs of bivalent radical (b) or their agriculturally-acceptable salts are the following compounds:

5,7-di-methyl-N-(2,6-dichlorophenyl)-1,2,4-triazolo[ 1,5-a] -pyrimidine-2-sulfonamide;
5-methyl-N-(2,6-dichlorophenyl)-1,2,4-triazolo[1,5-a]-pyrimidine- 2-sulfonamide;
5-methyl-N-(2-bromo-6-chlorophenyl)-1,2,4-triazolo[ 1,5-a]-pyrimidine-2-sulfonamide;
5-methyl-N-(2,6-difluoro-3-methylphenyl)-1,2,4-triazolo-[ 1,5-a]-pyrimidine-2-sulfonamide;
5-methyl-N-(2,6-difluorophenyl)-1,2,4-triazolo[1,5-a]-pyrimidine- 2-sulfonamide;
5,7-dimethoxy-N-(2,6-dichloro-3-methylphenyl)- 1,2,4-triazolo-[1,5-a]-pyrimidine-2-sulfonamide;
5,7-dimethoxy-N-(2-methoxy-6-trifluoromethyl-phenyl)-1,2,4-triazolo-[1,5-a]-pyrimidine-2-sulfonamide;
5-methyl-7-methylthio-N-(2,6-dichlorophenyl)-1,2,4-triazolo-[1,5-a]-pyrimidine-2-sulfonamide;
5-methyl-7-methylthio-N-(2-trifluoromethylphenyl)-1,2,4-triazolo-[1,5-a]-pyrimidine-2-sulfonamide;
7-ethoxy-5-methyl-N-(2,6-dichloro-3-methylphenyl)-1,2,4-triazolo-[1,5-a]pyrimidine-2-sulfonamide;
5,7-dimethoxy-N-(2-chloro-6-phenylphenyl)-1,2,4-triazolo[ 1,5-a]pyrimidine-2-sulfonamide;
5-methyl-N-(2-methyl-6-nitrophenyl)-1,2,4-triazolo[ 1,5-a]-pyrimidine-2-sulfonamide;
5-methyl-N-(2-chloro-6-methylphenyl)-1,2,4-triazolo[ 1,5-a]-pyrimidine-2-sulfonamide;
Methyl-3-methyl-N-(5,7-dimethyl-1,2,4-triazolo-[ 1,5-a]-pyrimidine-2-sulfonyl)anthranilate;
Methyl-3-methyl-N-(5-methyl-7-ethoxy-1,2,4-triazolo-[ 1,5-a]-pyrimidine-2-sulfonyl)anthranilate;
Isopropyl-3-methyl-N-(5-methyl-1,2,4-triazolo-[1,5-a]-pyrimidine- 2-sulfonyl)anthranilate;
6-Methyl-N-(2-bromo-6-methylphenyl)-1,2,4-triazolo-[ 1,5-a]-pyrimidine-2-sulfonamide;
6-Methyl-N-(2-fluoro-6-chlorophenyl)-1,2,4-triazolo-[ 1,5-a]-pyrimidine-2-sulfonamide;
6-Methyl-N-(2-chloro-6-methylphenyl)-1,2,4-triazolo[ 1,5-a]-pyrimidine-2-sulfonamide;
6-Methyl-N-(2-methyl-6-nitrophenyl)-1,2,4-triazolo-[ 1,5-a]-pyrimidine-2-sulfonamide;
7-Ethoxy-5-methyl-N-(2-trifluoromethylphenyl)-1,2,4-triazolo-[1,5-a]-pyrimidine-2-sulfonamide;
7-Methoxy-5-methyl-N-(2,6-dichloro-3-methylphenyl)-1,2, 4-triazolo-[1,5-a]-pyrimidine-2-sulfonamide;
7-Ethoxy-5-methyl-N-(2-bromo-6-chloro-3-methyl-phenyl)- 1,2,4-triazolo-[1,5-a]-pyrimidine-2-sulfonamide;
5,7-Dimethoxy-N-(2,6-dibromo-3-methylphenyl)-1,2,4-triazolo-[ 1,5-a]-pyrimidine-2-sulfonamide;
5,7-Dimethoxy-N-(2,6-dichlorophenyl)-1,2,4-triazolo-[ 1,5-a]-pyrimidine-2-sulfonamide;
7-Methyl-N-(2,6-dichlorophenyl)-1,2,4-triazolo-[ 1,5-a]-pyrimidine-2-sulfonamide;
N-(2,6-Dichlorophenyl)-1,2,4-triazolo-[1,5-a]-pyrimidine-2-sulfonamide;
7-Ethoxy-5-methyl-N-(2,6-dibromo-3-methylphenyl)-1,2, 4-triazolo-[1,5-a]-pyrimidine-2-sulfonamide;
6-Chloro-N-(2,6-difluorophenyl)-1,2,4-triazolo-[ 1,5-a]-pyrimidine-2-sulfonamide;
5-Methyl-7-trifluoromethyl-N-(2-methoxy-6-trifluoromethylphenyl)- 1,2,4-triazolo-[1,5-a]-pyrimidine- 2-sulfonamide;
Methyl-3-fluoro-N-(6-chloro-1,2,4-triazolo-[1,5-a]-pyrimidine- 2-sulfonyl)anthranilate;
5,7-Dimethyl-N-(1,3-dimethyl-5-trifluoromethyl-4-pyrazolyl)- 1,2,4-triazolo-[1,5-a]-pyrimidine-2-sulfonamide;
5-Methyl-N-(1,3-dimethyl-5-trifluoromethyl-4-pyrazolyl)- 1,2,4-triazolo-[1,5-a]-pyrimidine-2-sulfonamide;
5,7-Dimethyl-N-(1-methyl-4-ethoxycarbonyl-5-pyrazolyl)- 1,2,4-triazolo-[1,5-a]-pyrimidine-2-sulfonamide;
5,7-Dimethoxy-N-(2-chloro-1-napthyl)-1,2,4-triazolo-[ 1,5-a]pyrimidine-2-sulfonamide;
5-Methyl-7-methoxy-N-(2-chloro-1-naphthyl)-1,2,4-triazolo-[ 1,5-a]-pyrimidine-2-sulfonamide;
5-Methyl-7-ethoxy-N-(2-chloro-1-naphthyl)-1,2,4-triazolo-[ 1,5-a]-pyrimidine-2-sulfonamide;
5-Methyl-N-(2-methylpropanoyl)-N-(2,6-difluorophenyl)- 1,2,4-triazolo-[1,5-a]-pyrimidine-2-sulfonamide;
5-Methyl-N-acetyl-N-(2,6-dichlorophenyl)-1,2,4-triazolo-[ 1,5-a]-pyrimidine-2-sulfonamide;
5,7-Dimethyl-2-(N-[2-chloro, 6-propargyloxyphenyl]-sulphamoyl)- 1,2,4-triazolo[1,5-a]-pyrimidine;
5,7-Dimethyl-2-(N-[2-chloro-6-(2-ethoxyethoxy)-phenyl]-sulphamoyl)- 1,2,4-triazolo[1,5-a]-pyrimidine;
5,7-Dimethyl-2-(N-[2-benzyloxy-6-chlorophenyl]-sulphamoyl)- 1,2,4-triazolo[1,5-a]-pyrimidine;
5,7-Dimethyl-2-(N-[2-allyloxy-6-fluorophenyl]-sulphamoyl)- 1,2,4-triazolo[1,5-a]-pyrimidine;
5,7-Dimethyl-2-(N-[2-chloro-6-(2-methoxymethoxy)phenyl]-sulphamoyl)- 1,2,4-triazolo[1,5-a]-pyrimidine;
5,7-Dimethyl-2-(N-[2-chloro-6-(2-hydroxyethoxy)phenyl]-sulphamoyl)- 1,2,4-triazolo[1,5-a]-pyrimidine;
5,7-Dimethyl-2-(N-[2-2-ethoxyethoxy)-6-fluorophenyl]-sulphamoyl)- 1,2,4-triazolo[1,5-a]-pyrimidine;
5,7-Dimethyl-2-(N-[2-fluoro-6-(2-methylthioethoxy)-phenyl]-sulphamoyl)- 1,2,4-triazolo-[ 1,5-a]-pyrimidine;
5,7-Dimethyl-2-(N-[2-chloro-6-(2-phenoxyethoxy)phenyl] sulphamoyl)- 1,2,4-triazolo[1,5-a]-pyrimidine;
5,7-Dimethyl-2-(N-[2-chloro-6-(2-methoxyethoxy)phenyl]-sulphamoyl- 1,2,4-triazolo-[1,5-a]-pyrimidine;
5,7-Dimethyl-2-(N-[2-chloro-6-(2-n-propoxyethoxy)phenyl]-sulphamoyl)- 1,2,4-triazolo[1,5-a]-pyrimidine;
5,7-Dimethyl-2-(N-[2-chloro-6-(3-methoxy-n-propoxy)phenyl]-sulphamoyl)- 1,2,4-triazolo-[ 1,5-a]-pyrimidine;

5,7-Dimethyl-2-(N-[2-chloro-6-(2-isopropoxy)ethoxyphenyl]-sulphamoyl)- 1,2,4-triazolo-[ 1,5-a]-pyrimidine;
5,7-Dimethyl-(N-[2-fluoro-6-(2-n-propoxyethoxy)phenyl]-sulphamoyl)- 1,2,4-triazolo-[1,5-a]-pyrimidine;
5,7-Dimethyl-2-(N-[2-(2-ethoxyethoxy)phenyl]-sulphamoyl)- 1,2,4-triazolo-[1,5-a]-pyrimidine;
5,7-Dimethyl-2-(N-[2,6-di(2-ethoxyethoxy)phenyl]-sulphamoyl)- 1,2,4-triazolo-[1,5-a]-pyrimidine;
5,7-Dimethyl-2-(N-[2-2-ethoxyethoxy)-6-methoxy-phenyl]-sulphamoyl)- 1,2,4-triazolo[1,5-a]-pyrimidine;
5,7-Dimethyl)-2-(N-[2-chloro-6-tetrahydrofurfur-2-yl-oxyphenyl]-sulphamoyl)-1,2,4-triazolo-[1,5-a]-pyrimidine;
5,7-Dimethyl-2-(N-[2-(2-emthoxyethylamino)-phenyl]-sulphamoyl)- 1,2,4-triazolo[ 1,5-a]-pyrimidine;
5,7-Dimethyl-2-(N-[2-(2-methoxyethylthio)phenyl]-sulphamoyl)- 1,2,4-triazolo-[1,5-a]-pyrimidine;
5,7-Dimethyl-2-(N-acetyl-N-[2-chloro-6-(2-ethoxyethoxy)phenyl]-sulphamoyl)- 1,2,4-triazolo-[1,5-a]-pyrimidine;
5,7-Dimethyl-2-(N-acetyl-N-[2-chloro-6-(2-methoxyethoxy)phenyl]-sulphamoyl)- 1,2,4-triazolo-[1,5-a]-pyrimidine;
5,7-Dimethyl-2-(N-methyl-N-[2-chloro-6-(2-ethoxyethoxy)phenyl] -sulphamoyl)-1,2,4-triazolo-[1,5-a]-pyrimidine;
5,7-Dimethyl-2-(N-[2-(2-ethoxyethoxy)-6-nitrophenyl]sulphamoyl)- 1,2,4-triazolo-[1,5-a]-pyrimidine; and
5-Methoxymethyl-N-(2-chloro-6-methylphenyl)-1,2,4-triazolo-[ 2,5-a]-pyrimidine-2-sulfonamide.

Other preferred herbicidal compounds for use herein wherein in Formula I $R_1$ and $R_2$ are combined to form divalent radical (a) above, i.e.,

(a)

and R is $-SO_2N(R_6)(R_7)$, are those wherein A is $CR_3$, B is N and $R_6$, $R_7$, X, Y and Z have the above-defined meanings and $R_3$ is H, halogen, $NO_2$, CN, amino, phenyl, phenylthio, phenoxy, $C_{1-4}$ alkyl, mono- or di-$C_{1-4}$ alkylamino or alkoxy; $-S(O)_{0-3}-C_{1-4}$ alkyl; $C(O)C_{1-4}$ alkyl, -alkoxy, -alkylthio, mono- or dialkylamino or -phenyl; or a substitutable $R_3$ member substituted where not self-inclusive with halogen, $NO_2$, CN, $CF_3$ and/or $C_{1-3}$ alkyl, preferably methyl.

Preferred compounds according to the foregoing embodiment are those wherein:

X and Z are independently H, CN, halogen, amino, $C_{1-4}$ alkyl, haloalkyl, alkylthio, alkoxy or mono- or dialkylamino;

Y is H, CN, halogen, $C_{1-4}$ alkyl, haloalkyl or alkoxy;

$R_3$ is halogen, $NO_2$, CN, $C_{1-4}$ alkyl, haloalkyl, C(O)alkyl or C(O)alkoxy;

$R_6$ is H, benzyl, $C(O)C_{1-4}$alkyl or -haloalkyl and agriculturally-acceptable salts thereof when $R_6$ is H and $R_7$ is phenyl substituted in at least one ortho position with halogen, CN, $NO_2$, $C_{1-4}$ alkyl, haloalkyl or $S(O)_{1-3}$alkyl or haloalkyl; amino, mono- or di-$C_{1-4}$alkylamino, optionally substituted phenyl, phenylthio, phenoxy or benzyl, wherein said substituents are from 1 to 4 of halogen, $NO_2$, $CF_3$, CN or $C_{1-3}$ alkyl, preferably methyl; and at least one of the meta positions of the $R_7$ phenyl group is substituted with a $C_{1-3}$ alkyl, preferably methyl.

Representative species of the preceding compounds include the following:
N-(2,6-difluorophenyl)-4,6-dimethylimidazolo[1,2-a] -pyrimidine-2-sulfonamide;
N-(2,6-difluorophenyl)-3-chloro-4,6-dimethylimidazolo[ 1,2-a]-pyrimidine-2-sulfonamide;
N-(2,6-difluorophenyl)-3-bromo-4,6-dimethylimidazolo[ 1,2-a]-pyrimidine-2-sulfonamide;
N-(2,6-difluorophenyl)-3-methylthio-4,6-dimethylimidazolo[ 1,2-a]-pyrimidine-2-sulfonamide;
N-(2,6-dichlorophenyl)-4,6-dimethylimidazolo[1,2-a] -pyrimidine-2-sulfonamide;
N-(2,6-difluorophenyl)-3-cyano-4,6-dimethylimidazolo[ 1,2-a]-pyrimidine-2-sulfonamide;
N-(2,6-difluorophenyl)-N-benzyl-3-chloro-4,6-dimethylimidazolo[ 1,2-a]-pyrimidine-2-sulfonamide;
N-(2-trifluoromethylphenyl)-4,6-dimethylimidazolo[ 1,2-a] -pyrimidine-2-sulfonamide;
N-(2-trifluoromethylphenyl)-3-chloro-4,6-dimethylimidazolo[ 1,2-a]-pyrimidine-2-sulfonamide;
N-(2-carbomethoxy-6-methylphenyl)-3-chloro-4,6-dimethylimidazolo[ 1,2-a]-pyrimidine-2-sulfonamide;
N-(2,6-dichlorophenyl)-3-chloro-4,6-dimethylimidazolo[ 1,2-a]-pyrimidine-2-sulfonamide;
N-(2-chloro-6-methylphenyl)-3-chloro-4,6-dimethylimidazolo[ 1,2-a]-pyrimidine-2-sulfonamide;
N-(2,6-difluorophenyl)-4-chloro-6-methylimidazolo[ 1,2-a] -pyrimidine-2-sulfonamide;
N-(2,6-difluorophenyl)-4-methoxy-6-methylimidazolo[ 1,2-a]-pyrimidine-2-sulfonamide;
N-(2,6-difluorophenyl)-4,6-dichloroimidazolo[ 1,2-a]-pyrimidine-2-sulfonamide;
N-(2,6-difluorophenyl)-4,6-bismethoxyimidazolo[ 1,2-a]-pyrimidine-2-sulfonamide monohydrate;

Preferred and representative herbicidal compounds according to Formula I wherein $R_1$ and $R_2$ are combined to form the bivalent radicals (c) and (d) above include tautomeric forms of the following compounds:
5,7-Dimethyl-N-(2-chloro-6-methylphenyl)-1,2,4-triazolo-[ 1,5-a]-[4H,7H]-dihydropyrimidine-2-sulphonamide,
7-Methyl-N-(2-chloro-6-methylphenyl)-1,2,4-triazolo-[ 1,5-a][4H,7H]-dihydropyrimidine-2-sulphonamide;
5,7-Dimethyl-N-(2-chloro-6-ethoxyphenyl)-1,2,4-triazolo-[ 1,5-a][4H,7H]-dihydropyrimidine-2-sulphonamide or
5,7-Dimethyl-N-(2-chloro-6-isopropoxyphenyl)-1,2,4-triazolo-[ 1,5-a][4H,7H]-dihydropyrimidine-2-sulphonamide.

Another group of preferred herbicidal compounds of Formula I are those wherein $R_1$ and $R_2$ combine to form the divalent radical (e) above, i.e.,

(e)

wherein

X is H, $CF_3$, $C_{1-4}$ alkyl, alkylthio or alkoxy;

Y and Z are independently H, $CF_3$, $CF_3$, halogen or $C_{1-4}$ alkoxy; provided that at least one of X, Y or Z is $C_{1-4}$ alkoxy;

$R_6$ is H or $C(O)C_{1-4}$ alkyl or -haloalkyl and agriculturally-acceptable salts thereof when $R_6$ is H and $R_7$ is phenyl substituted in at least one ortho position with halogen, CN, $NO_2$, $C_{1-4}$ alkyl, haloalkyl or $S(O)_{1-3}$ alkyl or haloalkyl; amino, mono- or di-C $_{1-4}$ alkylamino, optionally-substituted phenyl, phenylthio, phenoxy or benzyl, wherein said substituents are from 1 to 4 of halogen, $NO_2$, $CF_3$, CN or $C_{1-3}$ alkyl, preferably methyl; and at least one of the meta positions of the $R_7$ phenyl group is substituted with a $C_{1-3}$ alkyl, preferably methyl.

One preferred compound according to those defined in the preceding paragraph is 5-fluoro-7-methoxy-N-( 2,6-difluorophenyl)-1,2,4-triazolo[1,5-c]-pyrimidine- 2-sulfonamide.

Still another group of herbicidal sulfonamide compounds useful in combination with antidotal compounds according to this invention are those identified as (6,7)-dihydro-[1,2,4]-triazolo[1,5-a]-[ 1,3,5]-triazine-2-sulfonamides. Such compounds are those according to Formula I wherein A and B are both N, R is $SO_2N(R_6)(R_7)$ and $R_1$ and $R_2$ are combined to form divalent radical (f) above, i.e.,

wherein

D is oxygen or sulfur;

X and Y are independently H, alkyl, alkenyl or alkynyl having up to 6 carbon atoms, phenyl, phenylalkyl, phenylalkenyl, phenylalkynyl or where not self-inclusive an X or Y member other than H substituted with one or more halogen, $C_{1-4}$ acyl, alkoxy, alkoxycarbonyl, alkoxycarbonyl-$C_{1-3}$ alkylene, carbamoyl, mono- or di-$C_{1-6}$ carbamoyl or $S(O)_{0-3}C_{1-6}$ alkyl;

$R_6$ is an X member or alkali metal atom or a single metal equivalent of an alkaline earth, other metal or ammonium anion, optionally substituted with $C_{1-6}$ alkyl and $R_7$ is preferably phenyl, naphthyl, pyridyl or thienyl, optionally substituted with halogen, CN, $NO_2$, $S(O)_{0-3}C_{1-6}$ alkyl, —$C_{2-6}$ alkenyl or alkynyl, amino, carbamoyl, mono- or di-$C_{1-4}$ alkylamino or -alkylcarbamoyl, $C_{1-6}$ alkyl, acyl, alkoxy, alkoxyalkyl, alkoxycarbanoyl-$C_{1-3}$ alkyl; phenyl or phenoxy optionally substituted with one or more $C_{1-4}$ alkyl, alkoxy, alkylthio, halogen, $NO_2$ or amino, which substituents where not self-inclusive and substitutable, substituted with alkyl, alkenyl or alkynyl having up to 6 carbons, which may optionally be substituted with one or more halogen, OH, CN, $NO_2$ or $C_{1-4}$ alkoxy or alkoxycarbonyl.

Exemplary preferred species according to the structure defined in the preceding paragraph include those wherein $R_7$ is phenyl substituted in the ortho positions independently with halogen, $CF_3$, $NO_2$, $C_{1-3}$ alkyl, alkoxy or alkoxycarbonyl and substituted in the meta and para positions with halogen, $CF_3$ or $C_{1-4}$ alkyl;

$R_6$ is H, $C_{1-4}$ acyl or a single equivalent of a metal ion and

X and Y are independently H, phenyl, alkyl, alkenyl or alkynyl having up to 6 carbon atoms.

Preferred species according to the preceding description include the following: N-(2,6-Dichlorophenyl)-6,7-dihydro-N,5,6-trimethyl-7-oxo[1,2,4]triazolo[1,5-a][1,3,5]-triazine-2-sulphonamide;

N-(2,6-Dichlorophenyl)-6,7-dihydro-5,6-dimethyl-7-oxo[ 1,2,4]triazole[1,5-a][1,3,5]-triazine-2-sulphonamide;

N-(2,6-dichlorophenyl)-6,7-dihydro-5,6-dimethyl-7-thioxo-[ 1,2,4]triazolo[1,5-a]-[1,3,5]-triazine- 2-sulphonamide;

N-(2,6-Dichlorophenyl)-6,7-dihydro-5,6-dimethyl-7-thioxo-[ 1,2,4]triazolo[1,5-a][1,3,5]triazine-2-sulphonamide;

N-(2,6-Dichloro-3-methylphenyl)-6,7-dihydro-5,6-dimethyl- 7-thioxo-[1,2,4]triazolo[1,5-a][1,3,5]triazine-2-sulphonamide;

6,7-Dihydro-5,6-dimethyl-N-(2-methyl-6-nitrophenyl)-7-thioxo-[1,2,4]triazolo-[1,5-a][ 1,3,5]-triazine-2-sulphonamide;

N-(2-Chloro-6-fluorophenyl)-6,7-dihydro-5,6-dimethyl-7-thioxo-[1,2,4]triazolo[1,5-a][1,3,5]triazine-2-sulphonamide;

N-(2,6-Difluorophenyl)-6,7-dihydro-5,6-dimethyl-7-thioxo-[ 1,2,4]triazolo[1,5-a]-[1,3,5]-triazine- 2-sulphonamide;

N-(2,6-Dibromophenyl)-6,7-dihydro-5,6-dimethyl-7-thioxo-[ 1,2,4]triazolo[1,5-a]-[1,3,5]-triazine-2-sulphonamide;

6,7-Dihydro-5,6-dimethyl-7-thioxo-N-(2-trifluoromethylphenyl)-[ 1,2,4]triazolo[1,5-a]-[1,3,5]triazine-2-sulphonamide;

6,7-Dihydro-5,6-dimethyl-N-phenyl-7-thioxo-[1,2,4]triazolo[ 1,5-a]-[1,3,5]-triazine-2-sulphonamide;

N-(2-Chlorophenyl)-6,7-dihydro-5,6-dimethyl-7-thioxo-[ 1,2,4]triazolo-[1,5-a]-[1,3,5]-triazine- 2-sulfonamide.

A modification of the preceding 6,7-dihydrotriazolotriazine sulfonamides includes compounds according to Formula I wherein the only change is that B is $CR_3$, rather than N; D, X, Y, R, $R_6$, $R_7$ and $R_1$ combined with $R_2$ to form the divalent radical (f), have the same meanings as defined above and $R_3$ is defined to have the same members as X and Y.

Preferred compounds according to this embodiment of the invention herbicides include those wherein $R_3$ is H, CN, $NO_2$, $C_{1-4}$ acyl or alkoxycarbonyl; carbamoyl, $C_{1-4}$ mono- or dialkyl carbamoyl or $S(O)_{0-3}$ $C_{1-4}$ alkyl;

$R_7$ is phenyl substituted in the ortho positions independently with halogen, $CF_3$, $NO_2$, $C_{1-3}$ alkyl, alkoxy or alkoxycarbonyl and substituted in the meta and para positions with halogen $CF_3$ or $C_{1-4}$ alkyl;

$R_6$ is H, $C_{1-4}$ acyl or a single equivalent of a metal ion and

X and Y are independently H, phenyl, alkyl, alkenyl or alkynyl having up to 6 carbon atoms.

Preferred species according to the preceding description include the following:

N-(2,6-Dichlorophenyl)-6,7-dihydro-5,6-dimethyl-3-methoxycarbonyl- 7-oxopyrazolo[1,5-a][1,3,5]-triazine- 2-sulphonamide;

N-(2,6-Difluorophenyl)-6,7-dihydro-5,6-dimethyl-3-methoxycarbonyl- 7-thioxopyrazolo[1,5-a][1,3,5]-triazine-2-sulphonamide;

N-(2,6-Difluorophenyl)-6,7-dihydro-5,6-dimethyl-3-methoxycarbonyl- 7-oxopyrazolo[1,5-a][1,3,5]-triazine- 2-sulphonamide;

N-(2,6-Dichlorophenyl)-6,7-dihydro-5,6-dimethyl-3-methoxycarbonyl- 7-thioxopyrazolo[1,5-a][1,3,5]-triazine-2-sulphonamide;

N-(2,6-Dichloro-3-methylphenyl)-6,7-dihydro-5,6-dimethyl- 3-methoxycarbonyl-7-oxopyrazolo[1,5-a] -[1,3,5]-triazine-2-sulphonamide;

N-(2,6-Dichloro-3-methylphenyl)-6,7-dihydro-5,6-dimethyl- 3-methoxycarbonyl-7-thioxopyrazolo-[ 1,5-a][1,3,5]-triazine-2-sulphonamide;

N-(2-Chloro-6-fluorophenyl)-6,7-dihydro-5,6-dimethyl-3-methoxycarbonyl-7-oxopyrazolo[ 1,5-a][1,3,5]-triazine-2-sulphonamide;

N-(2-Chloro-6-fluorophenyl)-6,7-dihydro-5,6-dimethyl-3-methoxycarbonyl-7-thioxopyrazolo[ 1,5-a][1,3,5]-triazine-2-sulphonamide;

N-(2-Chloro-6-methylphenyl)-6,7-dihydro-5,6-dimethyl-3-methoxycarbonyl-7-oxopyrazolo-[ 1,5-a][1,3,5]-triazine-2-sulphonamide;

N-(2-Chloro-6-methylphenyl)-6,7-dihydro-5,6-dimethyl-3-methoxycarbonyl-7-thioxopyrazolo-[ 1,5-a][1,3,5]-triazine-2-sulphonamide;

N-(2,6-Dibromophenyl)-6,7-dihydro-5,6-dimethyl- 3-methoxycarbonyl-7-oxopyrazolo[1,5-a][1,3,5]-triazine- 2-sulphonamide;

N-(2,6-Dibromophenyl)-6,7-dihydro-5,6-dimethyl-3-methoxycarbonyl- 7-thioxopyrazolo[1,5-a][1,3,5]-triazine-2-sulfonamide.

Another group of triazolosulfonamides safened according to this invention are those according to Formula I wherein $R_1$ and $R_2$ are combined to form the divalent radical (g) above, i.e.,

 (g)

and are characterized as thiazolotriazole sulfonamides, wherein:

X and Y are independently H, OH, CN, $NO_2$, halogen; alkyl, acyl, alkoxy, alkoxycarbonyl, alkenyl, alkenyloxy, alkynyl or alkynyloxy each having up to 6 carbon atoms; aryl, aralkyl or heterocyclic radical having up to 10 ring members of which up to 4 may be O, S and/or N atoms; or X and Y may be combined to form an alkylene chain of 3 or 4 carbon atoms; or said X and Y substitutable members substituted with another X or Y member when not self-inclusive;

$R_6$ is H, acyl, alkyl, alkenyl or alkoxycarbonyl having up to 6 carbon atoms; aryl, alkaryl or heterocyclyl having up to 10 ring members of which up to 4 may be O, S and/or N atoms; an alkali metal ion, ammonium or $C_{1-4}$ alkylammonium; or a substitutable $R_6$ member when not self inclusive substituted with alkyl, alkoxy, acyl, alkenyl, alkenyloxy, alkynyl, alkynyloxy having up to 6 carbon atoms and $R_7$ is an aromatic or heteroaromatic $R_6$ member.

Preferred members within the above thiazolotriazole sulfonamides are those wherein X and Y are independently H or $C_{1-6}$ alkyl, preferably methyl; $R_6$ is H and $R_7$ is phenyl substituted with one or more halogen, $NO_2$, $C_{1-4}$ alkyl, alkoxy, alkoxycarbonyl or alkylthio groups.

A preferred species according to the preceding group of compounds is N-(2,6-difluorophenyl)thiazole[3,2-b][1,2,4]triazole-2-sulfonamide.

The preceding embodiments of triazolo- and imidazolopyrimidine sulfonamide herbicides according to Formula I used in this invention are characterized by the R moiety $-SO_2N(R_6)(R_7)$. In the following embodiments analogous herbicides used herein are characterized by the R moiety $-N(R_4)SO_2-R_5$. In these embodiments both A and B are N, although it is within the purview of the invention to replace either A or B with the $=CR_3-$ moiety as with the foregoing embodiments.

The first group of compounds according to this embodiment of analogous compounds described in the preceding paragraph are those wherein $R_1$ and $R_2$ are combined to form the above bivalent radical (a), i.e.,

 (a)

or their tetrahydro analogs of bivalent radical (b) above, i.e.,

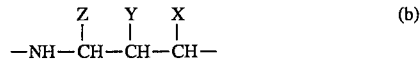 (b)

wherein X, Y, Z, $R_4$ and $R_5$ of Formula I have the same meanings as those described earlier herein.

Preferred compounds within this embodiment of herbicidal compounds are those wherein Y and $R_4$ are H;

X and Z are H or $C_{1-4}$ alkyl or alkoxy and $R_5$ is phenyl substituted in a first ortho position with halogen, $NO_2$, $CF_3$, CN, carboxyl or $C_{1-4}$ alkoxycarbonyl; in the other ortho position in H, halogen or $C_{1-4}$ alkoxycarbonyl and in the meta position adjacent said first ortho position with H, halogen or $C_{1-4}$ alkyl.

Preferred species in the foregoing group of compounds include the following:
N-5,7-dimethyl-4,5,6,7-tetrahydro-1,2,4-triazolo[1,5-a]-pyrimidine-2-yl-2-(2,6-dichlorophenyl)sulfonamide;
N-5-methyl-4,5,6,7-tetrahydro-1,2,4-triazolo[1,5-a] -pyrimidine-2-yl-2-(2,6-difluorophenyl)sulfonamide;
N-(5,7-Dimethyl-1,2,4-triazolo[1,5-a]-pyrimidin-2-yl)-2-thiophene sulfonamide;
N-Acetyl-2,6-dichloro-N-(5,7-dimethyl-1,2,4-triazolo[1,5-a]-pyrimidin-2-yl)-benzenesulfonamide;
N-(5-Amino-1,2,4-triazol-3-yl)-2-nitrobenzenesulfonamide;
N-(5,7-Dimethyl-1,2,4-triazolo[1,5-a]-pyrimidin- 2-yl)-2-nitrobenzenesulfonamide;
N-(5-Amino-1,2,4-triazol-3-yl)-2,5-dichlorobenzene-sulfonamide;
N-(5,7-Dimethyl-1,2,4-triazolo[1,5-a]pyrimidin-2-yl)- 2,5-dichlorobenzene-sulfonamide;
2-Chloro-N-(5-methyl-7-trifluoromethyl-1,2,4-triazolo[1,5-a]pyrimidin-2-yl)benzenesulfonamide
2-Chloro-N-(7-methyl-1,2,4-triazolo[1,5-a]-pyrimidin-2-yl)benzenesulfonamide;
2-Chloro-N-(1,2,4-triazolo[1,5-a]pyrimidin-2-yl)-benzene-sulfonamide;
2-Chloro-N-(6-Chloro-1,2,4-triazolo[1,5-a]-pyrimidin-2-yl)benzenesulfonamide;
2-Chloro-N-(6-methyl-1,2,4-triazolo[1,5-a]-pyrimidin-2-yl)benzenesulfonamide;
N-(5-Amino-1,2,4-triazol-3-yl)-2,6-dichlorobenzene-sulfonamide;

A second group of preferred herbicides in the class of those wherein in Formula I R is $N(R_4)SO_2R_5$ includes compounds wherein $R_1$ and $R_2$ are combined to form the bivalent radical (h), i.e.,

 (h)

wherein X, Y, $R_4$ and $R_5$ have the same general meanings and preferred members as described above in the first group of compounds wherein R is $N(R_4)SO_2(r_5)$.

Exemplary compounds within this group include the following compounds wherein $R_5$ is a substituted phenyl radical:
N-(5,7-dimethyl)-6,7-dihydro-[1,2,4]-triazole[1,5-a][1,3,5] -triazine-2-(2,6-difluorophenyl)sulfonamide;
N-(5-methyl)-6,7-dihydro-[1,2,4]-triazole[1,5-a][1,3,5]-triazine-2-(2,6-difluorophenyl)sulfonamide;
N-(7-methoxy0-6,7-dihydro-[1,2,4]-triazole[1,5-a][ 1,3,5]-triazine-2-(2,6-dichlorophenyl)sulfonamide;
N-(5,7-dimethoxy)-6,7-dihydro-[1,2,4]-triazole[1,5-a][1,3,5]-triazine-2-(2,3,6-trimethylphenyl)sulfonamide;
N-(5-chloro)-6,7-dihydro-[1,2,4]-triazole[1,5-a][1,3,5]-triazine-2-(2-acetyl-6-methylphenyl)sulfonamide and
N-(5-methoxymethyl)-6,7-dihydro[1,2,4]-triazole[1,5-a][1,3,5]-triazine-2-(2,6-difluorophenyl)sulfonamide.

Other preferred compounds are those wherein is a substituted pyrazolyl, furanyl or thiophenyl radical. Representative $R_5$ pyrazolyl members are the pyrazol-4-yl sulfonamide compounds (un) substituted in the 1-position with $C_{1-4}$ alkyl or phenyl and in the 3- and 5-positions with halogen, CN, $NO_2$, $CF_3$, phenyl, benzyl, $C_{1-4}$ alkyl, aminocarbonyl, mono- or dialkylamino carbonyl, alkoxycarbonyl, alkenyloxycarbonyl or alkynyloxycarbonyl, benzyloxycarbonyl or said phenyl and benzyl members substituted with halogen, $C_{1-4}$ alkyl or alkoxy.

Representative $R_5$ furanyl and thiophenyl members are the 2-yl and 3-yl isomers substituted in the substitutable positions of the 2-yl radical with one or more H, halogen or $C_{1-4}$ alkyl and in the 3-yl radical with one or more H, halogen or COO-alkyl, -alkenyl or alkynyl having up to 6 carbon atoms. Examples of such compounds are:

N-(5,7-dimethyl)-6,7-dihydro-[1,2,4]-triazole-[1,5-a][1,3,5]-triazine-2-thiophene sulfonamide;

N-(5-methyl)-6,7-dihydro-[1,2,4]-triazole-[1,5-a][1,3,5]-triazine-2-thiophenesulfonamide;

N-(5,7-dimethoxy)-6,7-dihydro-[1,2,4]-triazole[1,5-a][1,3,5]-triazine-2-furanesulfonamide;

N-(5-methoxymethyl)-6,7-dihydro-[1,2,4]-triazole[1,5-a][1,3,5]-triazine-furane sulfonamide;

N-(5-methyl)-6,7-dihydro-[1,2,4]-triazole[1,3,5]-triazine-2-(3-chloro-1-methyl-5-trifluoromethylpyrazol-4-yl)sulfonamide and N-(5,7-dimethyl)-6,7-dihydro-[1,2,4]-triazole-[1,3,5]-triazine-2-[4-chloro-5-methylsulfonyl)-pyrazol-4-yl]sulfonamide.

Preferred sulfonylurea compounds useful as the herbicidal component herein are those according to Formula II

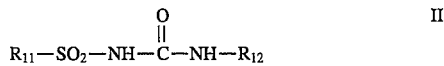

$$R_{11}-SO_2-NH-\overset{\underset{\|}{O}}{C}-NH-R_{12} \qquad II$$

wherein $R_{11}$ and $R_{12}$ are independently phenyl, benzyl, a heterocyclic radical containing up to 10 ring members of which up to 4 may be O, S and/or N atoms or said radicals substituted with halogen, amino, cyano, nitro, carbamoyl, $C_{1-4}$ alkyl, alkoxy, dihaloalkoxy, alkoxycarbonyl, mono- or dialkylamino, mono- or dialkylcarbamoyl or $S(O)_p$-alkyl, -alkenyl or -alkynyl having up to 4 carbon atoms or where not self-inclusive said substitutable radicals substituted with another $R_1$ member and p is 0–4.

In preferred embodiments of sulfonylurea compounds according to Formula II:

$R_{11}$ is a phenyl radical substituted in one position ortho to the —$SO_2$ radical with halogen, preferably chloro, $C_{1-3}$ alkoxycarbonyl, chloroalkoxycarbonyl or alkoxyalkoxy; a 2-($C_{1-4}$ alkoxycarbonyl) thiophen-3-yl radical; a pyridin-2-yl radical substituted in the 3-position with a $C_{1-3}$ alkylsulfonyl or N,N-$C_{1-3}$ dialkyl radical; pyrazol-3-yl, pyrazol-4-yl or pyrazol-5-yl radical or an imidazol-2-yl, imidazol-4-yl or imidazol-5-yl radical, said pyrazolyl- and imidazolyl-radicals being substituted in the 1 (or N)- position with H or a $C_{1-8}$ alkyl, preferably $C_{1-3}$ alkyl radical, and in the substitutable positions with H, halogen, preferably bromo or chloro, $NO_2$, $C_{1-4}$ alkyl, alkoxy, mono- or dialkylamino, or dialkylaminosulfonyl, alkylsulfinyl, alkylsulfonyl, thioalkyl or alkoxycarbonyl radical and $R_{12}$ is a pyrimidin-2-yl or 1,3,5-triazin-2-yl radical independently substituted in the 4- and 6- positions, respectively, with $C_{1-4}$ alkyl, preferably methyl, alkoxy, preferably methoxy, and/or difluoromethoxy radicals.

Preferred herbicidal sulfonylureas according to Formula II include:

Benzenesulfonamide, 2-chloro-N-[[(4-methoxy-6-methyl-1,3,5-triazin-2-yl)amino]carbonyl], (common name "chlorsulfuron");

Benzoic acid, 2-[[[[(4-chloro-6-methoxy-2-pyrimidin-2-yl)amino]carbonyl]amino]sulfonyl]ethyl ester, (common name "chlorimuron ethyl");

2-Thiophenecarboxylic acid, 3-[[[[(4,6-dimethoxy-1,3,5-triazin-2-yl)amino]-carbonyl] amino]sulfonyl]-, methyl ester, (code number DPX-M6316);

Benzoic acid, 2-[[[[(4,6-dimethyl-2-pyrimidin-2-yl) amino] carbonyl]amino]sulfonyl]methyl ester, (common name "sulfometuron methyl");

Benzenesulfonamide, 2-(2-chloroethoxy)-N-[[(4-methoxy-6-methyl-1,3,5-triazin-2-yl)amino]-carbonyl], (common name "triasulfuron");

Benzoic acid, 2-[[[[(4-methoxy-6-methyl-1,3,5-triazin-2-yl)amino]carbonyl]amino]sulfonyl]methyl ester, (common name "metsulfuron methyl");

Benzoic acid, 2-[[[[(4,6-di(difluoromethoxy) 2-pyrimidin-2-yl]amino]carbonyl]amino]sulfonyl] methyl ester, (common name "primisulfuron");

Pyridine-3-[[[[(4,6-dimethyl-2-pyrimidin-2-yl)-amino] carbonyl]amino]sulfonyl]N,N-dimethylcarbamoyl, (common name "nicosulfuron");

Pyridine, 3-[[[[(4,6-dimethoxy-2-pyrimidin-2-yl)amino] carbonyl]amino]sulfonyl]ethylsulfonyl, (code number "DPX E9636);

Benzenesulfonamide, 2-(methoxyethoxy)-N-[[(4,6-dimethoxy-1,3,5-triazin-2-yl) amino]carbonyl], (common name "cinosulfuron");

Methyl 2-[[[[[(4,6-dimethoxy-2-pyrimidin-2-yl)amino] carbonyl]amino]sulfonyl]methyl]benzoate, (common name "bensulfuron methyl"; code number DPX-5384);

N-[(4,6-dimethoxypyrimidin-2-yl)aminocarbonyl] -3-chloro-4-methoxycarbonyl-1-methylpyrazole-5-sulfonamide, (code number "NC-319");

N-[(4,6-dimethoxypyrimidin-2-yl)aminocarbonyl] -4-ethoxycarbonyl-1-methylpyrazole-5-sulfonamide, (common name "pyrazolsulfuron ethyl" code number "NC-311");

Methyl, [[[[N-(4-methoxy-6-methyl-1,3,5-triazin-2-yl)-methylamino]carbonyl]amino]sulfonyl] benzoate, (common name "tribenuron methyl"; Code No. DPX-L5300);

Benzoic acid, 2-[[[[(4-methylamino-6-ethoxy-1,3,5-triazin-2-yl)amino]carbonyl]amino]-sulfonyl] -methylester, (common name "ethametsulfuron methyl"; Code No. DPX-7881);

3-(4,6-dimethoxy-2-pyrimidin-2-yl)-1-(N-methyl-N-methylsulfonylaminosulfonyl) urea, (common name "amidosulfuron");

N-[(4,6-dimethylpyrimidin-2-yl) aminocarbonyl]-1-(1-methylethyl)-1H-imidazole-2-sulfonamide;

N-[(4-methoxy-6-methylpyrimidin-2-yl)aminocarbonyl] -1-(1-methylethyl)-1H-imidazole-2-sulfonamide;

N-[(4,6-dimethoxypyrimidin-2-yl)aminocarbonyl] -1-(1-methylethyl)-1H-imidazole-2-sulfonamide;

N-[(4,6-dimethylpyrimidin-2-yl)aminocarbonyl] -1-ethyl-1H-imidazole-2-sulfonamide;

N-[(4-methoxy-6-methylpyrimidin-2-yl)aminocarbonyl] -1-ethyl-1H-imidazole-2-sulfonamide;

N-[(4,6-dimethoxypyrimidin-2-yl)aminocarbonyl] -1-ethyl-1H-imidazole-2-sulfonamide;

N-[(4,6-dimethoxypyrimidin-2-yl)aminocarbonyl] -5-bromo-1-methyl-1H-imidazole-4-sulfonamide;

N-[[(4,6-dimethoxypyrimidin-2-yl)amino]carbonyl] -2-chloro-imidazo[1,2a]pyridine-3-sulfonamide, (Code No. TH-913).

Another class of preferred compounds useful as the herbicidal component herein are the imidazolinones. The basic groups of relevant imidazolinones comprehended herein are (un)substituted derivatives of (4,5-dihydro-4-oxo-1H-imidazol-2-yl)benzoic acid, (4,5-dihydro-4-oxo-1H-imidazol-2-yl)nicotinic acid and (4,5-dihydro-4-oxo-1H-imidazol-2-yl)quinolinecarboxylic acid. Derivatives of these acids include esters, amides, salts (e.g., alkali metals, especially potassium and sodium, mono- and di-alkyl amine and ammonium salts) and homologs, isomers (positional and optical) and homologs thereof, particularly of the preferred species listed below.

Examples of important imidazolinone herbicides include:
3-Quinolinecarboxylic acid, 2-[4,5-dihydro-4-methyl-4-(1-methylethyl)-5-oxo-1H-imidazol- 2-yl]-;
3-Pyridinecarboxylic acid, 2-[4,5-dihydro-4-methyl- 4-(1-methylethyl)-5-oxo-1H-imidazol-2-yl]-;
Benzoic Acid, 2-[4,5-dihydro-4-methyl-4-(1-methylethyl)-5-oxo-1H-imidazol-2-yl]-4(or 5)-methyl;
3-Pyridinecarboxylic acid, 5-ethyl-2-[4,5-dihydro-4-methyl- 4-(1-methylethyl)-5-oxo-1H-imidazol- 2-yl]-;
3-Pyridinecarboxylic acid, 2-[4,5-dihydro-4-methyl- 4-(1-methylethyl)-5-oxo-1H-imidazol- 2-yl]-5-methyl-, ammonium salt;
2-(5-Methyl-5-trifluoromethyl-1-H-imidazol-4-on-2-yl)-pyridin-3-carboxylic acid;
2-(5-Methyl-5-trifluoromethyl-1-H-imidazol-4-on-2-yl) 5-(m) ethyl isonicotinic acid;
2-[5-(1-Fluoroethyl)-5-(m) ethyl-H-imidazol-4-on-2-yl] isonicotinic acid;
2-(5-(Difluoromethyl-5-(m) ethyl-1-H-imidazol-4-on-2-yl]- 5-(m) ethyl-isonicotinic acid;
2-(5-(1-Fluoroethyl)-5-(m) ethyl)-imidazol -4-on-2-yl] isonicotinic (m) ethyl ester.

Another preferred class of compounds useful as the herbicidal component herein includes α-chloroacetamides according to Formula III

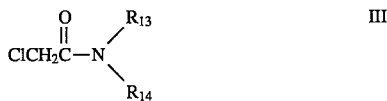 III wherein $R_{13}$ and $R_{14}$ are independently hydrogen; $C_{1-8}$ alkyl, alkoxy, alkoxyalkyl, acylaminomethyl, acyl-lower alkyl-substituted aminomethyl; cycloalkyl, cycloalkylmethyl, mono- or polyunsaturated alkenyl, alkynyl, cycloalkenyl, cycloalkenylmethyl having up to 8 carbon atoms; phenyl; or $C_{4-10}$ heterocyclyl or heterocyclylmethyl containing from 1 to 4 ring hetero atoms selected independently from N, S or O and wherein said $R_{13}$ and $R_{14}$ members may be substituted with alkyl, alkenyl, alkynyl, alkenyloxy, alkynyloxy, alkoxy, alkoxyalkyl, alkoxycarbomethyl or ethyl having up to 8 carbon atoms; nitro; halogen; cyano; amino or $C_{1-4}$ alkyl-substituted amino; and wherein $R_{13}$ and $R_{14}$ may be combined together with the N atom to which attached to form one of said heterocyclyl or substituted-heterocyclyl members.

Preferred herbicidal compounds according to Formula III are those wherein the $R_{13}$ member is an alkoxy- alkyl radical of the structure —(E)—O—L, wherein E and L are linear or branched-chain alkyl residues having a combined total of up to 8 carbon atoms; or a substituted or unsubstituted $C_{4-10}$ heterocyclyl or heterocyclylmethyl radical containing from 1 to 4 ring hetero atoms selected independently from N, S or O atoms and the $R_{14}$ member is also one of said heterocyclyl or heterocyclylmethyl radicals or an optionally-substituted phenyl radical. Preferably the phenyl radical is substituted with alkyl groups, especially in the ortho positions. Similarly, some preferred heterocyclic members are substituted with alkyl or alkoxy radicals.

Among the more important heterocyclic and/or $R_{14}$ members of Formula III are mentioned independently, the furanyl, thienyl, pyrazolyl, pyrrolyl, isoxazolyl, isothiazolyl, triazolyl, imidazolyl, and pyrimidinyl radicals and their analogs having a methylene (—$CH_2$—) moiety connecting the heterocyclic radical to the acetamide nitrogen atom, e.g., pyrazol-1-ylmethyl. When the heterocyclic radical is attached directly to the amide nitrogen (with no intervening methylene moiety), the attachment may be through a ring carbon atom or a ring hetero atom as appropriate.

Other important $R_{13}$ and/or $R_{14}$ members include the following: propynyl, alkoxycarbomethyl or -ethyl, alkoxyiminoalkyl, benzyl, hydroxyalkyl, haloalkoxy and haloalkoxyalkyl, cyanoalkoxy and -alkoxyalkyl, methyl, ethyl, propyl, butyl and their isomers, and the like.

Among preferred species of Formula III are mentioned N-(2,4-dimethylthien-3-yl)-N-(1-methoxyprop-2-yl)-2-chloroacetamide, N-(1H-pyrazol-1-ylmethyl)-N-(2,4-dimethylthien-3-yl)-2-chloroacetamide and N-(1-pyrazol- 1-ylmethyl)-N-(4,6-dimethoxypyrimidin-5-yl)-2-chloroacetamide.

Another important subgenus of preferred α-haloacetamide compounds useful as the herbicidal component herein are the α-chloroacetanilides according to Formula IV

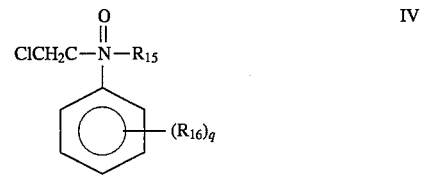 IV wherein
$R_{15}$ is hydrogen, $C_{1-6}$ alkyl, haloalkyl, alkoxy or alkoxyalkyl, alkenyl, haloalkenyl, alkynyl or haloalkynyl having up to 6 carbon atoms, $C_{5-10}$ heterocyclyl or heterocyclylmethyl having O, S and/or N atoms and which may be substituted with halogen, $C_{1-4}$ alkyl, carbonylalkyl or carbonylalkoxyalkyl, nitro, amino or cyano groups;

$R_{16}$ is hydrogen, halogen, nitro, amino, $C_{1-6}$ alkyl, alkoxy or alkoxyalkyl, and q is 0–5.

Examples of important acetamide herbicides according to Formulae III and IV are the following:
2-chloro-N-isopropylacetanilide (common name "propachlor");
2-chloro-1',6'-diethyl-N-(methoxymethyl)-acetanilide (common name "alachlor");
2-chloro-2',6'-diethyl-N-(butoxymethyl)-acetanilide (common name "butachlor");
2-chloro-N-(ethoxymethyl)-6'-ethyl-o-acetotoluidide (common name "acetochlor");
Ethyl ester of N-chloroacetyl-N-(2,6-diethylphenyl)glycine (common name "diethatyl ethyl");
2-chloro-N-(2,6-dimethylphenyl)-N-(2-methoxyethyl) acetamide (common name "dimethachlor");
2-chloro-N-(2-n-propoxyethyl)-2', 6'-diethyl-acetanilide (common name "pretilachlor");
2-chloro-N-(2-methoxy-1-methylethyl)-6'-ethyl-o-acetotoluidide (common name "metolachlor");
2-chloro-2'6'-dimethyl-N-(1-pyrazol-1-yl-methyl) acetanilide (common name "metazachlor");
2-chloro-N-(2,6-dimethyl-1-cyclohexen-1-yl)-N-( 1H-pyrazol-1ylmethyl)acetamide;
2-chloro-N-isopropyl-1-(3,5,5-trimethylcyclohexen-1-yl)acetamide (common name "trimexachlor");
2-Chloro-2'-methyl-6'-methoxy-N-(isopropoxymethyl) acetanilide;
2-Chloro-2'-methyl-6'-trifluoromethyl-N-(ethoxymethyl) acetanilide.
N-(2,4-dimethylthien-3-yl)-N-(1-methoxyprop-2-yl)-2-chloroacetamide;
N-(1H-pyrazol-2-ylmethyl)-N-(2,4dimethylthien- 3-yl)-2-chloroacetamide and
N-(1-pyrazol-1-ylmethyl)-N-(4,6-dimethoxypyrimidin-5-yl)-2-chloroacetamide.

The most preferred species of compounds according to Formula IV are 2-chloro-2'-ethyl-6'-methyl-N-(ethoxymethyl) acetanilide (common name "acetochlor"), 2-chloro-2',6'-diethyl-N-(methoxymethyl) acetanilide (common name "alachlor"), 2-chloro-2',6'-diethyl-N-(butoxymethyl)acetanilide (common name "butachlor"), 2-chloro-2'-ethyl-6'-methyl-N-(1-methyl-2-methoxyethyl)-acetanilide (common name "metolachlor"), 2-chloro-2',6'-diethyl-N-( 2-n-propoxyethyl)-acetanilide (common name "pretilachlor") and 2-chloro-2', 6'-dimethyl-N-(pyrazolylmethyl)acetanilide (common name "metazachlor").

A larger group of preferred α-chloroacetamide and α-haloacetanilide herbicides includes the particular preferred species of Formulae III and IV identified above.

Yet another class of preferred compounds useful as the herbicidal component in the composition/method according to this invention are the thiocarbamates.

Examples of important thiocarbamate herbicides are the following:

cis-/trans-2,3-dichloroallyl-diisopropylthiolcarbamate (common name "diallate");
Ethyl dipropylthiocarbamate (common name "EPTC");
S-ethyl diisobutyl (thiocarbamate) (common name "butylate");
S-propyl dipropyl (thiocarbamate) (common name "vernolate");
2,3,3-trichloroallyl-diisopropylthiocarbamate (common name "triallate").

A second component of the composition and method according to this invention is the biocidal compound. As used herein the terms "biocide(s)", "biocidal" or variations thereof refer to compounds and effects thereof used to eradicate non-plant, non-vegetal pests. Examples of such pests are insects, fungicides, nematodes, mites, etc. Contemplated herein are such non-vegetal pesticides as interact with the herbicidal component in the absence of the antidotal component to effect a negative synergism between the herbicide and biocide.

Particularly problematic biocides giving rise to negative synergism are various insecticides such as the organophosphates ("OPs"), carbamates, pyrethroids, cyclopropanecarboxylic acids and esters, carboxamides, dicarboximides, perchlorocyclohexane, etc. Because of their widespread use in agriculture, the OP insecticides have been particularly troublesome, especially when used in conjunction with sulfonylurea herbicides. Examples of such OP insecticides include terbufos (active ingredient in COUNTER®), chlorpyrifos (active ingredient in LORSBAN®), disulfoton (active ingredient in DISULFOTON® and DI-SYSTON®), phorate (active ingredient in THIMET®), dimethoate (active ingredient in CYGON®), malathion (active ingredient in MALATHION), etc.

Representative insecticidal pesticides include, e.g., the following compounds (by common or trade name): abamectin, aldicarb, acephate, aldrin, aminocarb, azinphos, bendiocarb, carbaryl, carbofuran, fonophos, chlormephos, DDT, dicofol, diflubenzuron, endothion, fenvalerate, FORCE®, heptachlor, methiocarb, methomyl, methyl-and ethyl-parathion, permethrin, pyrethrin, terbufos, etc.

Representative fungicidal pesticides which may be included with the above herbicides and insecticides include the following (by common or trade name); anilazine, benodanil, benomyl, butacarb, captafol, captan, carboxin, chloranil, chlorbromuron, chloroneb, chlorthalnil, chlorquinox, dazomet, dichlofluanid, diclone, dichloroaphen, dichloran, dithianon, dodine, dinocat, edifenphos, DOWSIDE-A®, ferbam, folpet, mancozeb, maneb, pyrazophos, thiabendazole, thiram, zineb, ziram, etc.

Representative nematicides which may serve as a biocidal component herein include, e.g., terbufos, fensulfothion, carbofuran, ethoprop, fenamiphos, dichloropropene, aldecarb and oxamyl.

Representative miticides which may be used as a biocidal component of the present invention include, e.g., formetanate hydrochloride, omite, profenofos, dimethoate, DIKAR®, ethion, dinocap, dicofol, amitraz, oxythioquinox, cyhexatin, fenbutatinoxide, oxamyl and phosalone.

The chemical names of the above insecticides, fungicides, nematicides and miticides are set forth, e.g., in the Farm Chemicals Handbook '88 and other sources of chemical compounds.

The third essential component of the composition/method according to this invention is the antidotal compound. This compound must be present in an amount sufficient to inhibit, nullify, reduce, mitigate or prevent negative synergism from the interaction of the herbicidal and biocidal components of the invention. This is an important and distinguishing feature of the invention herein vis-a-vis prior art and, indeed, current antidote technology and practice, wherein the objective was and is to utilize the minimum amount of antidote required to safen the known or exhibited normal, inherent herbicidal property (phytotoxicity) of a given herbicide or combination of herbicides. In contrast, the antidote technology of this invention has as its purpose the safening of enhanced herbicidal activity beyond that normally or inherently exhibited by a herbicide(s), i.e., negative synergy, generated by the interaction of a herbicide and a biocide, commonly an insecticide, especially an OP insecticide.

Thus, in prior and current practice, a herbicide product may normally cause a commercially-unacceptable amount of injury to a crop at a given application rate in the absence of an antidote. However, that crop injury at the same herbicide application rate may be readily prevented by using the necessary amount of an effective antidote.

Further, agrichemical practice has been and is to discover and use herbicidal products which can be safely used in crops without an antidote, and numerous such products have been introduced to the market. Still, a serious technical and economic problem involving many of these important unsafened herbicides is that upon contact of some herbicides with loci previously, concurrently or subsequently treated with various biocides, e.g., insecticides, fungicides, nematicides, etc., the natural, expected and known phytotoxicity of the herbicide unexpectedly increases markedly to a commercially-unacceptable degree. Multiple examples illustrating this problem and unsuccessful efforts of many workers in the art to solve the problem are set forth in the Background section of this application.

In order to concretely illustrate both the problem of negative synergy and failure of others to solve the problem, reference is again made to the article in the Canadian Journal of Plant Science cited supra, wherein corn injury resulting from the interaction of Eradicane (EPTC+dichlormid safener) and fonofos (an OP insecticide) was repeatedly reported in the field. The amount of safener present in Eradicane is, of course, sufficient to inhibit the normal phytotoxicity of the EPTC herbicide in corn. However, after multiple-year tests to confirm the fact and cause of the injury to corn by safened EPTC (Eradicane) in the presence of an OP insecticide (fonofos), the authors merely concluded that the phenomenon of negative synergy was inconsistent from year to year and possibly due to edaphic and climatic conditions. The authors, specifically studying the problem of negative synergy advanced no solution for the problem and, most conspicuously, failed to note any relationship and/or value to solving the problem by use of an appropriate antidote and adequate concentration thereof to overcome the negative synergy.

It is then highly surprising and unexpected that the above-described problem of negative synergy is subject to solution by the simple expedient (never discovered or recognized by other workers in this art) of using an effective amount of an antidote (beyond that normally sufficient to safen the normal, inherent herbicidal property of a compound) to prevent or mitigate the negative synergy.

The requisite amount of antidote is determinable by routine experimentation well within the skill of the art. There is no critical range of concentrations of herbicide:biocide:antidote, as the ratios of these components will vary considerably over wide ranges depending upon a plurality of factors, such as the particular herbicide, biocide and antidote system involved. The biological properties of each of these components is known to vary considerably, both inherently and under the specific edaphic and climatic conditions of use, e.g., soil, moisture, light, as well as susceptibility to injury of crop and weed species by the herbicide and other parameters. The critical feature of the invention is that whatever the properties of the herbicide/biocide/antidote system involved, inherent and/or environmental-use related, the amount of antidote employed will be such as to negate in part or full the negative synergy induced by the particular herbicide/biocide interaction.

It is understood and appreciated that various combinations of said components, amounts thereof and application modes, e.g., in tank-mix form, PPI, preemergence, in-furrow, postemergence, etc. will have varying degrees of efficacy in reducing negative synergism, hence some experimentation may be necessary in order to reach optimum results, but this will be within the skill of the art.

The antidotal compounds encompassed herein are:

(a) those according to Formula V

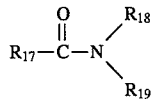

wherein $R_{17}$ can be selected from the group consisting of haloalkyl; polyhaloalkyl; haloalkenyl; alkyl; alkenyl; cycloalkyl; cycloalkylalkyl; halogen; hydrogen; carboalkoxy; N-alkenylcarbamylalkyl; N-alkenylcarbamyl; N-alkyl-N-alkynylcarbamyl; N-alkyl-N-alkynylcarbamylalkyl; N-alkenylcarbamylalkoxyalkyl; N-alkyl-N-alkynylcarbamylalkoxyalkyl; alkynoxy; haloalkoxy; thiocyanatoalkyl; alkenylaminoalkyl; alkylcarboalkyl; cyanoalkyl; cyanatoalkyl; alkenylaminosulfonalkyl; alkylthioalkyl; haloalkylcarbonyloxyalkyl, alkoxycarboalkyl; haloalkenylcarbonyloxyalkyl; hydroxyhaloalkyloxyalkyl; hydroxyalkylcarboalkoxyalkyl; hydroxyalkyl; alkoxysulfonoalkyl; furyl, thienyl; alkyldithiolenyl; thienalkyl; phenyl and substituted phenyl wherein said substituents can be selected from halogen, alkyl, haloalkyl, alkoxy, carbamyl, nitro, carboxylic acids and their salts, haloalkylcarbamyl; phenylalkyl; phenylhaloalkyl; phenylalkenyl; substituted phenylalkenyl wherein said substituents can be selected from halogen, alkyl, alkoxy, halophenoxy, phenylalkoxy; phenylalkylcarboxyalkyl; phenylcycloalkyl; halophenylalkenoxy; halothiophenylalkyl; halophenoxyalkyl; bicycloalkyl; alkenylcarbamylpyridinyl; alkynylcarbamylpyridinyl; dialkenylcarbamylbicycloalkenyl; alkynylcarbamylbicycloalkenyl;

$R_{18}$ and $R_{19}$ can be the same or different and can be selected from the group consisting of alkenyl; haloalkenyl; hydrogen; alkyl; haloalkyl; alkynyl; cyanoalkyl; hydroxyalkyl; hydroxyhaloalkyl; haloalkylcarboxyalkyl; alkylcarboxyalkyl; alkoxycarboxyalkyl; thioalkylcarboxyalkyl; alkoxycarboalkyl; alkylcarbamyloxyalkyl; amino; formyl; haloalkyl-N-alkylamido; haloalkylamido; haloalkylamidoalkyl; haloalkyl-N-alkylamidoalkyl; haloalkylamidoalkenyl; alkylimino; cycloalkyl; alkylcycloalkyl; alkoxyalkyl; alkylsulfonyloxyalkyl; mercaptoalkyl; alkylaminoalkyl; alkoxycarboalkenyl; haloalkylcarbonyl; alkylcarbonyl; alkenylcarbamyloxyalkyl; cycloalkylcarbamyloxyalkyl; alkoxycarbonyl; haloalkoxycarbonyl; halophenylcarbamyloxyalkyl; cycloalkenyl; phenyl; substituted phenyl wherein said substituents can be selected from alkyl, halogen, haloalkyl, alkoxy, haloalkylamido, phthalamido, hydroxy, alkylcarbamyloxy, alkenylcarbamyloxy, alkylamido, haloalkylamido or alkylcarboalkenyl; phenylsulfonyl; substituted phenylalkyl wherein said substituents can be selected from halogen or alkyl; dioxyalkylene, halophenoxyalkylamidoalkyl; alkylthiodiazolyl; piperidyl; piperidylalkyl; dioxolanylalkyl, thiazolyl; alkylthiazolyl; benzothiazolyl; halobenzothiazolyl; furyl; alkyl-substituted furyl; furylalkyl; pyridyl; alkylpyridyl; alkyloxazolyl; tetrahydrofurylalkyl; 3-cyano, thienyl; alkyl-substituted thienyl; 4,5-polyalkylenethienyl; α-haloalkylacetamidophenylalkyl; α-haloalkylacetamidonitrophenylalkyl; α-haloalkylacetamidohalophenylalkyl; cyanoalkenyl;

$R_{18}$ and $R_{19}$ when taken together can form a structure consisting of piperidinyl; alkylpiperidinyl; pyridyl; di- or tetrahydropyridinyl; alkyltetrahydropyridyl; morpholyl; alkylmorpholyl; azabicyclononyl; diazacycloalkanyl; benzoalkylpyrrolidinyl; oxazolidinyl; perhydrooxazolidinyl; alkyloxazolidyl; furyloxazolidinyl; thienyloxazolidinyl; pyridyloxazolidinyl; pyrimidinyloxazolidinyl; benzooxazolidinyl; $C_{3-7}$ spirocycloalkyloxazolidinyl; alkylaminoalkenyl; alkylideneimino; pyrrolidinyl; piperidonyl; perhydroazepinyl; perhydroazocinyl; pyrazolyl; dihydropyrazolyl; piperazinyl; perhydro-1,4-diazepinyl; quinolinyl; isoquinolinyl; dihydro-, tetrahydro- and perhydroquinolyl- or -isoquinolyl; indolyl and di- and perhydroindolyl and said combined $R_{17}$ and $R_{18}$ members substituted with those independent $R_{17}$ and $R_{18}$ radicals enumerated above;

(b) one of the following compounds

α-[(Cyanomethoxy)imino]benzeneacetonitrile (common name "cyometrinil"),

α-[(1,3-Dioxolan-2-yl-methoxy)imino]benzeneacetonitrile (common name "oxabetrinil"), O-[1,3-Dioxolan-2-ylmethyl]-2,2,2-trifluoromethyl-4'-chloroacetophenone oxime, Benzenemethamine, N-[4-(dichloromethylene)-1,3-dithiolan-2-ylidene]-α-methyl, hydrochloride, Diphenylmethoxy acetic acid, methyl ester, 1,8-Naphthalic anhydride, 4,6-Dichloro-2-phenyl-pyrimidine, 2-Chloro-N-[1-(2,4,6-trimethylphenyl)ethenyl] acetamide, Ethylene glycol acetal of 1,1-dichloroacetone, 1,3-Dioxolane, 2-(dichloromethyl)-2-methyl-, 5-Thiazolecarboxylic acid, 2-chloro-4-(trifluoromethyl)-, (phenylmethyl)-ester (common name "flurazole"), Phosphorothioic acid, O,O-diethyl O-(3-methylphenyl)ester,
4-Pentenenitrile, 2-methyl-2-[(4-methylphenyl)thio]-,
5-Chloro-8-(cyanomethoxy)quinoline,
1-Methylhexyl-2-(5-chloro-8-quinolinoxy)acetate or
O-(Methoxycarbonyl)-2-(8-quinolinoxy)acetamide oxime
or (c) Any of the compounds identified hereinafter as Antidote Nos. 11, 29–33 or 42–80.

One group of preferred antidotal compounds includes those according to Formula V wherein $R_{17}$ is $C_{1-3}$ haloalkyl, $R_{18}$ and $R_{19}$ are independently $C_{2-4}$ alkenyl or haloalkenyl or 2,3-dioxolan-2-yl-methyl and $R_{18}$ and $R_{19}$ when combined form a $C_{4-10}$ saturated or unsaturated heterocyclic ring containing O, S and/or N atoms and which may be substituted with $C_{1-5}$ alkyl, haloalkyl, alkoxy, or alkoxyalkyl or haloacyl groups. The preferred haloalkyl $R_{17}$ member in Formula V is dichloromethyl. Preferred species in this group of antidotal compounds are N,N-diallyl-dichloroacetamide and N-(2-propenyl)-N-(1,3-dioxolanylmethyl)dichloroacetamide (Code No. PPG-1292).

Still more preferred antidotal compounds according to Formula V is a sub-group of substituted 1,3-oxazolidinyl dichloroacetamide having the formula

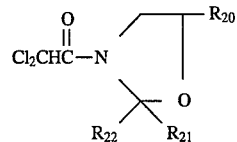

VI wherein $R_{20}$ is hydrogen, $C_{1-4}$ alkyl, alkylol, haloalkyl or alkoxy, $C_{2-6}$ alkoxyalkyl, a bicyclic hydrocarbon radical having up to 10 carbon atoms, phenyl or a saturated or unsaturated heterocyclyl (or heterocyclylmethyl) radicals having $C_{4-10}$ ring atoms and containing O, S and/or N atoms, or said phenyl, heterocyclyl, and heterocyclylmethyl radicals substituted with one or more $C_{1-4}$ alkyl, haloalkyl, alkoxy, alkoxyalkyl, halogen or nitro radicals, and $R_{21}$ and $R_{22}$ are independently hydrogen, $C_{1-4}$ alkyl or haloalkyl, phenyl or a heterocyclyl $R_{20}$ member or together with the carbon atom to which they are attached may form a $C_3$–$C_7$ spirocycloalkyl group.

Preferred members according to Formula VI are those wherein $R_{20}$ is hydrogen or one of said heterocyclylmethyl members and $R_{21}$ and $R_{22}$ are independently methyl, trifluoromethyl or when combined with the carbon atom to which attached form a $C_5$ or $C_6$ cycloalkyl radical.

Preferred antidotal compounds according to Formula VI are the following compounds:

Oxazolidine, 3-(dichloroacetyl)-2,2,5-tri-methyl-, (code number R-29148),
Oxazolidine, 3-(dichloroacetyl)-2,2-dimethyl- 5-phenyl-,
Oxazolidine, 3-(dichloroacetyl)-2,2-dimethyl- 5-(2-furanyl)-,
Oxazolidine, 3-(dichloroacetyl)-2,2-dimethyl- 5-(2-thienyl)-,
Pyridine, 3-[3-(dichloroacetyl)-2,2-dimethyl- 5-oxazolidinyl]-,
4-(dichloroacetyl)-1-oxa-4-azaspiro-(4,5)-decane (common name "AD-67").

Another group of dichloroacetamide antidotal compounds according to Formula V are the following compounds:
4-(Dichloroacetyl)-3,4-dihydro-3-methyl-2H- 2,4-benzoxazine,
Ethanone, 2,2-dichloro-1-(1,2,3,4-tetrahydro- 1-methyl-2-isoquinolinyl)-,
N-(Dichloroacetyl)-1,2,3,4-tetrahydroquinaldine,
1-(Dichloroacetyl)-1,2,3,4-tetrahydroquinoline,
Cis/trans-piperazine, 1,4-bis(dichloro 1,4-acetyl)- 2,5-dimethyl-,
1,5-Diazacyclononane, 1,5-bis-(dichloroacetyl,
1-Azaspiro[4,4]nonane, 1-(dichloroacetyl),
Pyrrolo[1,2-a]-pyrimidine-[6(2H)]-one, 1-(dichloroacetyl-)hexahydro- 3,3,8a-trimethyl,
2,2-Dimethyl-3-(dichloroacetyl)-1,3-oxazole 2,2-Dimethyl-5-methoxy-3-(dichloroacetyl)-1,3-oxazole and
(N-(2-propenyl)-N-(1,3-dioxolan-2-ylmethyl)-dichloroacetamide (Code number PPG-1292).

Still another preferred group of antidotal compounds are the following which have a structure not according to Formula V, i.e., those in Paragraph (b) above:
α-[(Cyanomethoxy) imino]benzeneacetonitrile,
α-[(1,3-Dioxolan-2-yl-methoxy)imino]benzeneacetonitrile,
O-[1,3-Dioxolan-2-ylmethyl]-2,2,2-trifluoromethyl-4'-chloroacetophenone oxime,
Benzenemethamine, N-[4-(dichloromethylene)- 1,3-dithiolan-2-ylidene]-α-methyl, hydrochloride,
Diphenylmethoxy acetic acid, methyl ester,
1,8-Naphthalic anhydride,
4,6-Dichloro-2-phenyl-pyrimidine,
2-Chloro-N-[1-(2,4,6-trimethylphenyl)ethenyl] acetamide,
Ethylene glycol acetal of 1,1-dichloroacetone,
1,3-Dioxolane, 2-(dichloromethyl)-2-methyl-,
5-Thiazolecarboxylic Acid, 2-chloro-4-(trifluoromethyl)-, (phenylmethyl)ester,
Phosphorothioic acid, O,O-diethyl O-(3-methylphenyl)ester,
4-Pentenenitrile, 2-methyl-2-[(4-methylphenyl)thio]-,
5-Chloro-8-(cyanomethoxy)quinoline,
1-Methylhexyl-2-(5-chloro-8-quinolinoxy)acetate or
O-(Methoxycarbonyl)-2-(8-quinolinoxy)-acetamide oxime.

The herbicidal and antidotal compounds of Formulae I-VI are known in the art.

Compositions of particular and preferred interest herein include combinations of the herbicidal components: nicosulfuron, primisulfuron, DPX-E9636, NC-311, NC-319 acetochlor and XRD-498 (N-(2,6-difluoro-phenyl)- 5-methyl(1,2,4)-triazolo[1,5-a]pyrimidine-2-sulfonamide); the biocidal components terbufos, chlorpyrifos, disulfoton and phorate and the antidotal components: dichlormid (R-25788), PPG-1292 (N-(2-propenyl)-N-( 1,3-dioxolan-2-ylmethyl)dichloroacetamide), AD-67 and MON-13900 (oxazolidine, 3-(dichloroacetyl)-2,2-dimethyl-5-(2-furanyl)—) and other compounds according to Formulae V and VI.

Of further particular interest are compositions comprised of nicosulfuron, primisulfuron, DPX-E 9636, NC-311, NC-319 or acetochlor as the herbicidal component; phorate, terbufos or chlorpyrifos as the insecticidal component and AD-67 or MON-13900 as the antidotal component.

The components of the composition may comprise individual members of each class, i.e., herbicidal, biocidal and antidotal components, or combinations of members of each class, particularly the herbicidal and biocidal classes. Illustrative herbicidal compounds which may be particularly suitable as co-herbicides with the preferred ALS inhibitor classes of herbicides, i.e., sulfonylureas, imidazolinones and azolopyrimidine sulfonamides, are further exemplified below.

It is emphasized that the compositions of this invention are not limited to those the herbicidal component of which operates via the ALS inhibition or similar mode of action in a weed plant. More broadly this invention contemplates the inhibition or reduction of negative synergy arising from any combination of herbicidal and biocidal components, regardless of the mode of action in the plant's system, by means of a sufficient quantity of antidotal compound to effect weed control and crop safety.

As disclosed in more detail below, above compositions may be formed in a variety of ways, including tank mixing the said separate components for either bulk dispersal or for pre-packaging for storage, transportation, sale and use. Said compositions are also formed when the individual components are separately applied to the locus of use and there combine in contact with each other simultaneously or sequentially in any order. For example, the biocidal components may be first applied to the soil alone or together with the antidotal component, followed by application of the herbicidal component or the antidotal component may be applied to the seeds of the crop plant prior to planting in soil previously or subsequently treated with the biocidal component. The only caveat in forming said composition is that the antidotal component always be present to combat negative synergy.

The term "haloalkyl" embraces radicals wherein any one or more of the carbon atoms, preferably from 1 to 4 in number, is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. Examples of a polyhaloalkyl are perhaloalkyl groups such as trifluoromethyl and perfluoroethyl groups.

Where in Formulae III, IV and VI the halogen attached to the acetyl radical is the chlorine ion, it is contemplated that the other halogens, i.e., bromo, iodo or fluoro may be substituted for the chloro.

Preferred haloalkyl $R_{17}$ members of Formula V are dihalomethyl, particularly dichloromethyl, while the preferred haloalkyl $R_{18}$ a member is a tri-halogenated methyl radical, preferably trifluoromethyl.

Where the term "alkyl" is used either alone or in compound form (as in "haloalkyl"), it is intended to embrace linear or branched radicals having up to four carbon atoms, the preferred members being methyl and ethyl.

By "agriculturally-acceptable salts" of the compounds defined by the above formula is meant a salt or salts which readily ionize in aqueous media to form a cation or anion of said compounds and the corresponding salt anion or cation, which salts have no deleterious effect on the antidotal properties of said compounds or of the herbicidal properties of a given herbicide and which permit formulation of the herbicide-antidote composition without undue problems of mixing, suspension, stability, applicator equipment use, packaging, etc.

By "antidotally-effective" is meant the amount of antidote required to reduce the phytotoxicity level or effect of a herbicide, preferably by at least 10% or 15%, but naturally the greater the reduction in herbicidal injury the better.

By "herbicidally-effective" is meant the amount of the herbicide component (individual or plural) required to effect a meaningful injury or destruction to a significant portion of affected undesirable plants or weeds. Although of no hard and fast rule, it is desirable from a commercial viewpoint that 80–85% or more of the weeds be destroyed, although commercially significant suppression of weed growth can occur at much lower levels, particularly with some very noxious, herbicide-resistant plants.

The terms "antidote" "safening agent", "safener", "antagonistic agent", "interferant", "crop protectant" and "crop protective", are often-used terms denoting a compound capable of reducing the phytotoxicity of a herbicide to a crop plant or crop seed. The terms "crop protectant" and "crop protective" are sometimes used to denote a composition containing as the active ingredients, a herbicide-antidote combination which provides protection from competitive weed growth by reducing herbicidal injury to a valuable crop plant while at the same time controlling or suppressing weed growth occurring in the presence of the crop plant. Antidotes protect crop plants by interfering with the herbicidal action of a herbicide on the crop plants so as to render the herbicide selective to weed plants emerging or growing in the presence of crop plants.

Herbicides which may be used as co-herbicides with the azolopyrimidine sulfonamides of Formula I, the sulfonylureas of Formula II, α-haloacetamides of Formulae III or IV, the imidazolinones and thiocarbamate components of the invention composition and method with benefit in combination with an antidotes as described herein include, heterocyclyl phenyl ethers (especially phenoxypyrazoles) and pyridines and many others. It is within the purview of this invention that many other classes of herbicides, e.g., triazines, ureas, diphenyl ethers, benzoic acid derivatives, nitroanilines, thiazoles, isoxazoles, pyrrolidinones, aromatic and heterocyclic di- and triketones, etc., the individual members of which classes may be derivatives having one or more substituents selected from a wide variety of radicals may suitably be used as co-herbicides. Such combinations can be used to obtain selective weed control with low crop injury in several varieties of monocotyledonous crop plants such as corn, grain sorghum (milo), and cereals such as wheat, rice, barley, oats, and rye, as well as several varieties of dicotyledonous crop plants including oil-seed crops such as soybeans and cotton. Particular utility for the antidotal compounds of this invention has been experienced with various herbicides in corn, sorghum and soybeans.

Examples of important pyridine herbicides include:

3-pyridinecarboxylic acid,-2(difluoromethyl)- 5-4,5-dihydro-2-thiazolyl-4-(2-methylpropyl)-6-(trifluoromethyl)-, methyl ester;

3-pyridinecarboxylic acid, 2-(difluoromethyl)- 4-(2-methylpropyl)-5-(1H-pyrazol- 1-ylcarbonyl)-6-(trifluoromethyl)-, methyl ester;

3,5-pyridinedicarboxylic acid, 2-(difluoromethyl)- 4-(2-methylpropyl)-6-trifluoromethyl, dimethyl ester.

3,5-pyridine dicarbothioic acid, 2-(difluoromethyl)- 4-(2-methylpropyl)-6-(trifluoromethyl)-, S,S-dimethyl ester.

Examples of important heterocyclyl phenyl ethers include:

5-(trifluoromethyl)-4-chloro-3-(3'-[1-ethoxycarbonyl] -ethoxy-4'-nitrophenoxy)-1-methylpyrazole;

5-(trifluoromethyl)-4-chloro-3-(3'-methoxy- 4'-nitrophenoxy)-1-methylpyrazole;

5-(trifluoromethyl)-4-chloro-3-(3'-[1-butoxycarbonyl] -ethoxy-4'-nitrophenoxy)- 4-methylpyrazole;

5-(trifluoromethyl)-4-chloro-3-(3'-methylsulfamoylcarbonyl propoxy-4'-nitrophenoxy)-4-methylpyrazole;

5-(trifluoromethyl)-4-chloro-3-(3'-propoxy-carbonylmethyloxime- 4'-nitrophenoxy)-1-methylpyrazole;

(±)-2-[4-[[5-(trifluoromethyl)-2-pyridinyl]oxy] phenoxy] propanoic acid.

Examples of important benzoic acid derivative herbicides include:

3,6-Dichloro-2-methoxybenzoic acid (common name "dicamba"), 2,5-Dichloro-3-aminobenzoic acid (common name "amiben" and "chloramiben"), 5-(2'-Chloro-4'-trifluoromethylphenoxy)-2-nitrobenzoic acid (common name "acifluorfen"), 2,6-Dichlorobenzonitrile (common name "dichlobenil"), 3,5,6-Trichloro-2-methoxybenzoic acid (common name "Tricamba"), 2,3,6-Trichlorobenzoic acid, and 2,3,5,6-Tetrachlorobenzoic acid, and salts, esters and amides of the above acids.

Examples of other important herbicides include:

2-Chloro-4-(ethylamino)-6-(isopropylamino)-s-triazine;

4-Amino-6-tertbutyl-3-(methylthio)as-triazine- 5(4H)one;

Trifluoro-2,6-dinitro-N,N-dipropyl-p-toluidine;

Benzeneamine, N-(1-ethylpropyl)-3,4-dimethyl- 2,6-dinitro-;

2-Pyrrolidinone, 3-chloro-4-(chloromethyl)- 1-[3-(trifluoromethyl)phenyl], trans-;

3-Isoxazolidinone, 2-[(2-chlorophenyl)-methyl] -4,4-dimethyl-;

2-Imidazolidinone, 3-[5-(1,1-dimethylethyl)- 3-isoxazolyl]-4-hydroxy-1-methyl-;

2-Chloro-4-(1-cyano-1-methylethylamino)-6-ethylamino-1,3,5-triazine;

Methyl 5-(2,4-dichlorophenoxy)-2-nitrobenzoate;

1'-(Carboethoxy)ethyl-5-[2-chloro-4-(trifluoromethyl)phenoxy] -2-nitrobenzoate;

Ammonium-DL-homoalanin-4-yl(methyl)phosphinate;

1-[(2-Fluoro-4-chloro-5-(2,3-dimethyl-butoxyphenyl]tetrahydrophthalimide and 2-(3,4-Dichlorophenyl)-4-methyl-1,2,4-oxadiazolidine- 3,5-dione.

The herbicides of particular and preferred interest as co-herbicides with the azolopyrimidine sulfonamides, imidazolinones and sulfonylurea in compositions with antidotes according to this invention include each of the above-mentioned species from different chemical classes of compounds exemplified as important herbicides, particularly those of current commercial interest and use and those which may be determined of commercial utility.

Co-herbicidal compounds of preference include the following:

alachlor, acetochlor, butachlor, metolachlor, pretilachlor metazachlor, 2-chloro-2',6'-dimethyl-N-(2-methoxyethyl)acetanilide, butylate and combinations thereof with the commercial antidotes R-29148 or PPG-1292 and EPTC and combinations thereof with the commercial antidotes R-25788, R-29148 or PPG-1292 any of which may further contain an extender, e.g., dietholate.

All of the above specifically-named antidotes and herbicides are known in the art.

As further detailed infra, while not necessary, the composition containing the herbicide/-biocide/antidote combination may also contain other additaments, e.g., fertilizers, inert formulation aids, e.g., surfactants, emulsifiers, defoamers, dyes, extenders, etc.

It will be recognized by those skilled in the art that all herbicides have varying degrees of phytotoxicity to various plants because of the sensitivity of the plant to the herbicide. Thus, e.g., although certain crops such as corn and soybeans have a high level of tolerance (i.e., low sensitivity) to the phytotoxic effect of alachlor, other crops, e.g., milo (grain sorghum), rice and wheat, have a low level of tolerance (i.e., high sensitivity) to the phytotoxic effects of alachlor. The same type of sensitivity to herbicides as shown by crop plants is also exhibited by weeds, some of which are very sensitive, others very resistant to the phytotoxic effects of the herbicide.

When the sensitivity of a crop plant to a herbicide is low, whereas the sensitivity of a weed to that herbicide is high, the "selectivity factor" of the herbicide for preferentially injuring the weed while not injuring the crop is high.

In an analogous, but more complex, manner, an antidotal compound may, and commonly does, have varying degrees of crop protective effect against different herbicides in different crops. Accordingly, as will be appreciated by those skilled in the art, the various antidotes of this invention, as with all classes of antidotal compounds, will have greater or lesser crop safening effects against various herbicides and herbicide combinations in various crops than in others. Thus, while a given antidotal compound may have no crop protective ability against a given herbicide in a given crop, that same antidotal compound may have a very high crop protective ability against the same given herbicide in a different crop or against a different herbicide in the same crop at the same or different rate of application or in a different application mode, i.e., PPI, PRE, seed dressing, etc. This is an expected phenomenon.

Biological Evaluation

Effective weed and non-plant pest control coupled with low crop injury is a result of treatment of a plant locus with a combination of herbicide, biocide, e.g., insecticide compounds and antidote compounds. By application to the "plant locus" is meant application to the plant growing medium, such as soil, as well as to the seeds, emerging seedlings, roots, stems, leaves, or other plant parts.

The phrase "combination of herbicide and/or insecticide compound and antidote compound" embraces various methods of treatment. For example, the soil of a plant locus may be treated with a "tank-mix" composition containing a mixture of the herbicide, insecticide and the antidote which is "in combination". Or, the soil may be treated with the herbicide, insecticide and antidote compounds separately so that the "combination" is made on, or in, the soil. After such treat-treatments of the soil with a mixture of herbicide, insecticide and antidote or by separate or sequential application of the herbicide, insecticide and antidote to the soil, the herbicide, insecticide and antidote may be mixed into or incorporated into the soil either by mechanical mixing of the soil with implements or by "watering in" by rainfall or irrigation. The soil of a plant locus may also be treated with antidote by application of the antidote in a dispersible-concentrate form such as a granule. The granule may be applied to a furrow which is prepared for receipt of the crop seed and the herbicide and insecticide may be applied to the plant locus either before or after in-furrow placement of the antidote-containing granule so that the herbicide, insecticide and antidote form a "combination". Crop seed may be treated or coated with the antidote compound either while the crop seed is in-furrow just after seeding or, more commonly, the crop seed may be treated or coated with antidote prior to seeding into a furrow. The herbicide and insecticide may be applied to the soil plant locus before or after seeding and a "combination" is made when both herbicide, insecticide and antidote-coated seed are in the soil. Also contemplated as a "combination" is a commercially-convenient association or presentation of herbicide, insecticide and antidote. For example, the herbicide, insecticide and antidote components in concentrated form may be contained in separate containers, but such containers may be presented for sale or sold together as a "combination" (composition). Or, the herbicide, insecticide and antidote components in concentrated form may be in a mixture in a single container as a "combination". Either such "combination" may be diluted or mixed with adjuvants suitable for soil applications. Another example of a commercially-presented combination is a container of antidote-coated crop seed sold, or presented for sale, along with a container of herbicide or insecticide material. These containers may, or may not, be physically attached to each other, but nonetheless constitute a "combination of herbicide, insecticide and antidote" when intended for use ultimately in the same plant locus.

In the foregoing description of various modes of application of the herbicide/insecticide/antidote combinations, it is inherent that each form of application requires that in some manner, sufficient antidote be present to combat negative synergism induced by interaction of the herbicide and insecticide.

The amount of antidote employed in the methods and compositions of the invention will vary depending upon the particular herbicide and herbicide/insecticide combination with which the antidote is employed, the rate of application of the herbicide, the particular crop to be protected, and the manner of application to the plant locus. In each instance the amount of antidote employed is a safening-effective amount, that is, the amount which reduces, or protects against, crop injury and negative synergism that otherwise would result from the presence of the herbicide and insecticide. The amount of antidote employed will be less than an amount that will substantially injure the crop plant.

The antidote can be applied to the crop plant locus in a mixture with the selected herbicide and/or insecticide. For example, where the crop seed is first planted, a suitable mixture of antidote and herbicide and/or insecticide, whether in a homogeneous liquid, emulsion, suspension or solid form, can be applied to the surface of, or incorporated in, the soil in which the seed has been planted. Or, the herbicide/insecticide/antidote mixture may be applied to the soil, and then the seed thereafter "drilled" into the soil below the soil layer containing the herbicide/insecticide/antidote mixture. The herbicide will reduce or eliminate the presence of undesirable weed plants. Where the herbicide would by itself injure the crop seedlings, the presence of the antidote will reduce or eliminate the injury to the crop seed caused by the herbicide often exacerbated by an insecticide. It is not essential that the application of herbicide, insecticide and the antidote to the plant locus be made using the selected herbicide, insecticide and antidote in the form of a mixture or composition. The herbicide and the antidote or the insecticide and antidote may be applied to the plant locus in a sequential manner. For example, the insecticide and/or antidote may be first applied to the plant locus and thereafter the herbicide is applied. Or, the herbicide may be first applied to the plant locus and thereafter the antidote with or preceding application of the insecticide is applied.

The ratio of herbicide to antidote may vary depending upon the crop to be protected, weed to be inhibited, herbicide used, etc., but normally a herbicide-to-antidote ratio ranging from 1:25-to-60:1 (preferably 1:5-to-30:1) parts by weight may be employed, although much higher rates of antidote may be used, e.g., 1:100–1:300 parts by weight of herbicide-to-antidote. As indicated above, the antidote may be applied to the plant locus in a mixture, i.e., a mixture of a herbicidally-effective amount of herbicide and a safening-effective amount of an antidote, or sequentially, i.e., the plant locus may be treated with an effective amount of the herbicide followed by a treatment with the antidote or vice versa. In general, effective herbicidal amounts are in the range of about 0.03 to about 12 kilograms/hectare, but rates as low as 0.004 kg/ha may be used effectively. The preferred range of rate of application is from about 0.1 to about 10 kg/ha. Preferably, antidote application rates range from about 8–10 kg/ha down to about 0.05 kg/ha. It will be appreciated that at times amounts either below or above these ranges will be necessary to obtain the best results. The selection of the herbicide to inhibit the emergence and growth of weeds depends upon the species of weeds to be controlled and the crop to be protected.

The biocide will be applied at rates recommended by the supplier/manufacturer.

The application of the antidote can be made directly to the seed before planting. In this practice, a quantity of crop seed is first coated with the antidote. The coated seed is thereafter planted. The herbicide may be applied to the soil before or after the coated seed is planted.

In field applications, the herbicide, insecticide, antidote, or a mixture thereof, may be applied to the plant locus without any adjuvants other than a solvent. Usually, the herbicide, insecticide, antidote, or a mixture thereof, is applied in conjunction with one or more adjuvants in liquid or solid form. Compositions or formulations containing mixtures of an appropriate herbicide, insecticide and antidote usually are prepared by admixing the herbicide, insecticide and antidote with one or more adjuvants such as diluents, solvents, extenders, carriers, conditioning agents, water, wetting agents, dispersing agents, or emulsifying agents, or any suitable combination of these adjuvants. These mixtures may be in the form of particulate solids, granules, pellets, wettable powders, dusts, solutions, aqueous dispersions, or emulsions.

Application of the herbicide, insecticide, antidote, or mixture thereof, can be carried out by conventional techniques utilizing, for example, hand-carried or tractor-mounted spreaders, power dusters, boom and hand sprayers, spray dusters, and granular applicators. If desired, application of the compositions of the invention to plants can be accomplished by incorporating the compositions in the soil or other media.

The sequence of addition of chemicals is optional, but in common applications, the insecticide may be applied to the soil followed by application of the antidote alone or in admixture with the herbicide. Various sequential modifications of application of the chemicals is contemplated. In general, the herbicide, biocide and/or antidote may be applied preemergence by preplant incorporation surface application or postemergence. The only condition being that the insecticide and herbicide not be active in the plant in the absence of the antidote in order to prevent or reduce negative synergism induced by interaction of the herbicide and insecticide.

Evaluations of safening activity of representative antidote compounds of this invention were carried out using the specific procedures described below in greenhouse and field testing. Measurements of biological response as reported in the tables were made by visual observation and the degree of plant injury recorded in terms of percent injury.

Listed below are the names of various insecticidal compounds tested herein and representative ones for which data are reported in the tables.

| Biocide No. | Nomenclature |
|---|---|
| 1 | S-[[(1,1-dimethyl-ethyl)thio]-methyl]O,O-diethylphosphorodithioate; (common name "terbufos", active ingredient in COUNTER ®) |
| 2 | O,O-Diethyl O-(3,5,6-trichloro-2-pyridyl)-phosphorothioate; (common name "chlorpyrifos", active ingredient in LORSBAN ®); |
| 3 | 2,3,5,6-tetrafluoro-4-methylbenzyl-(Z(-(1 RS, 3RS)-3-(2-Chloro-3,3,3-trifluoroprop-1-ethyl)-2, 2-dimethyl-cyclopropane carboxylate (common name "tefluthin", active ingredient in FORCE ®); |
| 4 | 2,3-Dihydro-2,2-dimethyl-7-benzofuranyl methylcarbamate; (common name "carbofuran"), active ingredient in FURADAN ®); |
| 5 | O,O-Diethyl (-(2-isopropyl-4-methyl-6-pyrimidinyl phosphorothioate (common name "diazinon"); |
| 6 | O,O-Diethyl-O-1,2,2,2-tetrachloroethyl phosphorothioate, (code No. DPX-43898); |
| 7 | O,O-Dimethyl phosphorothioate of diethyl mercaptosuccinate or diethyl mercaptosuccinate, S-3ster with O,O-dimethyl phosphorothioate (common name "malathion"); |
| 8 | O-Ethyl-S,S-dipropyl phosphorothioate (common name "ethoprop"); |
| 9 | O-Ethyl-S-phenylethylphosphonodithioate, (common name "fonofos") and |
| 10 | O,O-Diethyl S-[(ethylthio)methyl]phosphorodithioate (common names "phorate" and "thimet"). |

Listed below are exemplary herbicidal and co-herbicidal compounds tested herein.

| Herbicide No. | Nomenclature |
|---|---|
| 1 | N-[(4,6-dimethoxypyrimidin-2-yl)aminocarbonyl]-3-chloro-4-methoxycarbonyl-5-sulfonamide; (Code No. NC-319); |
| 2 | 2-Chloro-2'-ethyl-6'-methyl-N-(ethoxymethyl)acetanilide (common name "acetochlor") |
| 3 | 2-Chloro-2',6'-diethyl-N-(methoxymethyl)acetanilide (common name "alachlor"); |
| 4 | 2-Thiophenecarboxylic acid, 3-[[[[(4,6-dimethoxy-1,3,5-triazin-2-yl)amino]-carbonyl]amino]sulfonyl]-, methyl ester, (Code No. DPX-M6316); |
| 5 | Benzoic acid, 2-[[[[(4-chloro-6-methoxy-2-pyrimidin-2-yl)amino]-carbonyl]amino]sulfonyl]ethyl ester, (common name "chlorimuron ethyl"); |
| 6 | 3-Pyridinecarboxylic acid, 2-[4,5-dihydro-4-methyl-4-(1-methylethyl)-5-oxo-1H-imidazol-2-yl]5-ethyl (common name "imazathapyr") |
| 7 | Pyridine-3-[[[[(4,6-dimethyl-2-pyrimidin-2-yl)amino]carbonyl]amino]-sulfonyl) N,N-dimethylcarbamoyl (common name "nicosulfuron"); |
| 8 | Benzoic acid, 2-[[[[[4,6-di(difluoro-methoxy)-2-pyrimidin-2-yl]amino]carbonyl]amino]sulfonyl]methyl ester, (common name "primisulfuron"); |
| 9 | 2-Chloro-4-(ethylamino)-6-(isopropyl-amino)-S-triazine (common name "atrazine"). |
| 10 | Benzoic acid, 2-[[[[(4-methoxy-6-methyl-1,3,5-triazin-w-YL)amino]carbonyl]amino]sulfonyl]-, methyl ester (common name "metsulfuron/methyl"); |
| 11 | Benzenesulfonamide, 2-(2-chloroethoxy)-N-[[(4-methoxy-6-methyl-1,3,5-triazin-2-yl)amino]carbonyl]- (common name "triasulfuron"); |
| 12 | Benzenesulfonamide, 2-chloro-N-[[(4-methoxy-6-methyl-1,3,5-triazin-2-yl)amino]carbonyl]- (common name "chlorsulfuron" |
| 13 | Benzoic acid, 2-[[[[(4,6-dimethyl-2-pyrimidinyl)amino]carbonyl]amino]-sulfonyl]-, methyl ester (common name "sulfometuron methyl"); |
| 14 | Benzoic acid, 2-[[[[(4,6-dimethoxy-2-pyrimidinyl)amino]carbonyl]amino]sul-fonyl]methyl]-, methyl ester (common name "bensulfuron methyl"); |
| 15 | Methyl, [[[[N-(4-methoxy-6-methyl-1,3,5-triazin-2-yl)-methylamino]carbonyl]amino]sulfonyl]benzoate (common name "tribenuron methyl", Code No. DPX-L5300); |
| 16 | 3-Quinolinecarboxylic acid, 2-[4,5-dihydro-4-methyl-4-(1-methylethyl)-5-oxo-1H-imidazol-2-yl]- (common name "imazaquin"); |
| 17 | 3-Pyridinecarboxylic acid, 2-[4,5-dihydro-4-methyl-4-(1-methylethyl)-5-oxo-1H-imidazol-2-yl]-5-methyl-, ammonium salt (Code No. AC 263,222); |
| 18 | 3-Pyridinecarboxylic acid, 2-[4,5-dihydro-4-methyl-4-(1-methylethyl)-5-oxo-1H-imidazol-2-yl]- (common name "imazapyr"); |
| 19 | Benzoic acid, 2-[4,5-dihydro-4-methyl-4-(1-methylethyl)-5-oxo-1H-imidazol-2-yl]-4(or 5)-methyl- (Code No. AC 222,293); |
| 20 | 5,5-Dimethyl-N-(2,6-dichloro-3-methyl-phenyl)-1,2,4-triazolo[1,5-a]pyrimidine-2-sulfonamide; |
| 21 | 5-Methyl-N-(2,6-difluorophenyl)-1,2,4-triazolo[1,5-a]pyrimidine-2-sulfonamide (Code No. XRD-498); |
| 22 | 5,7-Dimethyl-N-(2-nitrophenyl)-1,2,4-triazolo[1,5-a]pyrimidine-2-sulfonamide; |
| 23 | 5,7-Dimethyl-N-[2-methoxy-6-(trifluoro-methyl)phenyl]-1,2,4-triazolo[1,5-a]-pyrimidine-2-sulfonamide; |
| 24 | 5-Methyl-7-ethoxy-N-(2,6-dichloro-3-methylphenyl)-1,2,4-triazolo[1,5-a]-pyrimidine-2-sulfonamide; |
| 25 | N-(2,6-Difluorophenyl)-3-chloro-4,6-dimethylimidazolo[1,2-a]pyrimidine-2-sulfonamide; |
| 26 | N-(5,7-Dimethyl-1,2,4-triazolo[1,5-a]-pyrimidin-2-yl)-2,6-dichlorophenyl sulfonamide; |
| 27 | 5-Fluoromethyl-7-methoxy-N-(2,6-dichlorophenyl)-1,2,4-triazolo[1,5-a]-pyrimidine-2-sulfonamide and |
| 28 | 5-Methoxy-7-fluoro-N-(2,6-difluoro-phenyl)-1,2,4-triazolo-'1,5-c]-pyrimidine-2-sulfonamide. |

In the list of co-herbicides below, it will be noted that certain of the compounds are also listed in the preceding list of herbicides. This is merely for convenience in designating which compounds in the tables which follow are treated as "herbicides" (numbered compounds) and which are used as "co-herbicides" (lettered compounds), although it will be appreciated, these are all herbicides, as distinct from the biocidal and antidotal components of the test compositions. It is to be noted that EPTC (Co-Herbicide D herein) is a well-known herbicide by itself or as a mixture with an antidote, dichlormid, (ERADICANE®) or in combination with another antidote, R-29148, and a soil-life extender, dietholate, (ERADICANE® EXTRA). For purposes of this invention, when ERADICANE is used as the herbicide/ antidote composition, it is to be provided that the biocidal component is an organophosphorus compound other than fonofos.

| Co-Herbicide | Nomenclature |
| --- | --- |
| A | 2-Chloro-N-(ethoxymethyl)-6'-ethyl-o-acetotoluidide ("acetochlor"); |
| B | 2-Chloro-1',6'-diethyl-N-(methoxy methyl)acetanilide (common name "alachlor"); |
| C | 2-Chloro-N-(2-methoxy-1-methylethyl)-6'-ethyl-o-acetotoluidide ("metolachlor"); |
| D | S-Ethyl dipropylcarbamothioate (common name "EPTC"); |
| E | S-Ethyl-bis(2-methylpropyl)carbamothioate ("butylate"); |
| F | Dimethylamine salt of 2-methoxy-3,6-dichlorobenzoic acid (common name "dimethylamine salt of dicamba"); |
| G | 2-([4-Chloro-6-(ethylamino)-1,3,5-triazin-2-yl]amino]-2-methylpropionitrile (common name "calcium cyanamide" or "cyanazine"); |
| H | 2,4-Dichlorophenoxyacetic acid (common name "2,4-D"); |
| I | N-[(4,6-Dimethoxypyrimidin-2-yl)amino-carbonyl]-3-chloro-4-methoxycarbonyl-5-sulfonamide (Code No. NC-319); |
| J | 5-Methyl-N-(2,6-difluorophenyl)-1,2,4-triazolo[1,5-a]pyrimidine-2-sulfon-amide (Code No. XRD-498) and |
| K | 3-Pyridinecarboxylic acid, 2-[4,5-dihydro-4-methyl-4-(1-methylethyl)-5-oxo-1H-imidazol-2-yl]-5-ethyl (common name "imazethapyr"). |

Listed below are the preferred compounds used as antidotes in various herbicide/biocide/antidote compositions/ methods according to this invention.

| Antidote No. | Nomenclature |
| --- | --- |
| 1 | Oxazolidine, 3-(dichloroacetyl)-2,2-dimethyl-5-(2-furanyl)- (Code No. MON-13900), |
| 2 | Acetamide, N,N-Bis(2-propenyl)-alpha,alpha-dichloro- (common name "dichlormid"), |
| 3 | Piperazine, 1,4-Bis(Dichloroacetyl)-, |
| 4 | Benzenemethanamine, N-<4-(dichloromethylene)-1,3-dithiolan-2-ylidene,-alpha-methyl-, hydrochloride, |
| 5 | 1H,3H-Naphtho<1,8-cd>pyran-1,3-dione, |
| 6 | Cis/trans-piperazine, 1,4-bis(dichloroacetyl)-2,5-dimethyl-, |
| 7 | 5-Thiazolecarboxylic acid, 2-chloro-4-(trifluoromethyl)-, (phenylmethyl) ester, |
| 8 | Oxazolidine, 3-(dichloroacetyl)-2,2,5-trimethyl-, |
| 9 | Benzeneacetonitrile, alpha-<(cyanomethoxy)imino>-, |
| 10 | Oxazolidine, 3-(dichloroacetyl)-2,2-di-methyl-5-phenyl)-, |
| 11 | 5-Oxazolecarboxylic acid, 2-<(2,2-dimethylethyl)amino>-4-(trifluoromethyl)-, ethyl ester, |
| 12 | Acetic acid, (diphenylmethoxy)-, methyl ester (Code No. MON-7400), |
| 13 | Quinoline, 1-(dichloroacetyl)-1,2,3,4-tetrahydro-2-methyl-, |
| 14 | Isoquinoline, 2-(dichloroacetyl)-1,2,3,4-tetrahydro-, |
| 15 | Benzeneacetonitrile, alpha-{<(1,3-dioxolan-2-yl)methoxy>imino}-, (available only as Concep II ™ sorghum seed), |
| 16 | 1-Oxa-4-azaspiro<4.5>decane, 4-(dichloroacetyl)-, |
| 17 | 1,5-Diazacyclononane, 1,5-bis(dichloroacetyl)-, |
| 18 | Acetamide, N-<1,1'-biphenyl>-3-yl-2,2-dichloro-, |
| 19 | 1-Azaspiro<4.4>nonane, 1-(dichloroacetyl)-, |
| 20 | Acetamide, 2,2-dichloro-N-(1,3-dioxolan-1-ylmethyl)-N-2-propenyl-, |
| 21 | 1-Azaspiro<4.5>decane, 1-bromo-chloroacetyl-, |
| 22 | Oxazolidine, 3-(dichloroacetyl)-2,2-dimethyl-5-(2-thienyl)-, |
| 23 | Ethanone, 2,2-dichloro-1-(1,2,3,4-tetrahydro-1-methyl-2-isoquinolinyl)-, |
| 24 | 1,3-Dioxolane, 2-(dichloromethyl)-2-methyl-, |
| 25 | Acetamide, 2-chloro-N-<1-(2,4,6-tri-methylphenyl)ethenyl>-, |
| 26 | Isoquinoline, 2-(dichloroacetyl)-1,2,3,4-tetrahydro-1,3-dimethyl-, |
| 27 | Pyridine, 3-<3-(dichloroacetyl)-1,2-dimethyl-5-oxazolidinyl>-, |
| 28 | 4-(Dichloroacetyl)-3,4-dihydro-3-methyl-2H-1,4-benzoxazine, |
| 29 | Allyl-N-methyldithiocarbanilate, |
| 30 | 4-Isoxazolecarboxylic acid, 5-(2,4-dichlorophenyl)-, ethyl ester, |
| 31 | Pyrimidine, 4,6-dichloro-2-phenyl-, |
| 32 | 4-Pentenenitrile, 2-methyl-2-[(4-methylphenyl)thio]-, |
| 33 | Acetonitrile, [(5-chloro-8-quinolinyl)oxy]-, |
| 34 | Oxazolidine, 3-(dichloroacetyl)-2,2-dimethyl-5-(phenylmethyl)-, |
| 35 | Oxazolidine, 3-(dichloroacetyl)-2,2-dimethyl-5-(1-methyl-1H-pyrrol-2-yl)-, |
| 36 | Oxazolidine, 3-(dichloroacetyl)-5-(2-furanyl)-2-phenyl-, |
| 37 | Pyridinium, 3-(3-dichloroacetyl-2,2-dimethyl-5-oxazolidinyl)-1-methyl-, salt with trifluoromethanesulfonic acid (1:1), |
| 38 | Oxazolidine, 5-(2-benzofuranyl)-3-(dichloroacetyl)-2,2-dimethyl-, |
| 39 | Isoquinoline, 2-(dichloroacetyl)-1-ethyl-1,2,3,4-tetrahydro-, |
| 40 | Isoquinoline, 2-(dichloroacetyl)-1,2,3,4-tetrahydro-1-phenyl-, |
| 41 | Isoquinoline, 2-(dichloroacetyl)-1,2,3,4-tetrahydro-1-(2-methylpropyl)-, |
| 42 | Acetamide 2-(diphenylmethoxy)-N-methyl-, |
| 43 | Glycine, N-[bis(4-methoxyphenyl)-methyl]-, ethyl ester, |
| 44 | Glycine, N-[bis(4-chlorophenyl)-methyl]-, ethyl ester, |
| 45 | Acetic acid, [(10,11-dihydro-5H-dibenzo[a,d]cyclohepten-5-yl)oxy]-, 1,1-dimethylethyl ester, |
| 46 | Ethanethioamide, 2-(diphenylmethoxy)-, |
| 47 | Acetic acid, (diphenylmethoxy)-, propyl |

| Antidote No. | Nomenclature |
|---|---|
| | ester, |
| 48 | Acetic acid, (diphenylmethoxy)-, 2,2,2-trifluoroethyl ester, |
| 49 | Acetic acid, {phenyl[3-(trifluoromethyl)phenyl]methoxy}-, 2-methyl-2-propanamine salt, |
| 50 | Acetic acid, (diphenylmethoxy)-, phenyl ester, |
| 51 | Ethanethioic acid, 2-(diphenylmethoxy)-, S-ethyl ester, |
| 52 | Acetic acid, (diphenylmethoxy-, 2-cyanoethyl ester, |
| 53 | Acetic acid, {phenyl[3-(trifluoromethyl)phenyl]methoxy}-, 2,2,2-trifluoroethyl ester, |
| 54 | Acetic acid, (diphenylmethoxy)-, 2-propynyl ester, |
| 55 | Acetic acid, (diphenylmethoxy)-, 3-furanylmethyl ester, |
| 56 | Acetic acid, ([bis(2,6-dimethylphenyl)-methoxy]-, |
| 57 | Acetic acid, (diphenylmethoxy)-, 3-nitrophenyl ester, |
| 58 | Acetic acid, {(bis(2,6-dimethylphenyl)]methoxyl-, ethyl ester, |
| 59 | Acetic acid, (diphenylmethoxy)-, 1-cyano-1-methylethyl ester, |
| 60 | 5-Thiazolecarboxylic acid, 2-chloro-4-(trifluoromethyl)-, ethyl ester, |
| 61 | 5-Thiazolecarboxylic acid, butyl ester, 2-chloro-, 4-(trifluoromethyl)-, |
| 62 | 5-Thiazolecarboxylic acid, 2-chloro-, hexyl ester, 4-(trifluoromethyl)-, |
| 63 | 5-Thiazolecarboxylic acid, 2-chloro-4-(trifluoromethyl)-, octyl ester, |
| 64 | 5-Thiazolecarboxylic acid, 2-chloro-4-(trifluoromethyl)-, phenyl ester, |
| 65 | 5-Thiazolecarboxylic acid, 2-chloro-4-(trifluoromethyl)-, |
| 66 | 5-Thiazolecarboxylic acid, 2-[bromo-4-(trifluoromethyl)]-, ethyl ester, |
| 67 | 5-Thiazolecarboxylic acid, 2-iodo-4-(trifluoromethyl)-, ethyl ester, |
| 68 | 5-Thiazolecarboxylic acid, 2-chloro-4-(trifluoromethyl)-, 1-methylethanamine salt, |
| 69 | Benzylamine-, (alpha-methyl-, N-4-(methyl)-1,3-dithiol-2-ylidene) hydrochloride, |
| 70 | Pyridine, N-oxide, 2-(3,4,5,6-tetrachloro-2-pyridylthio)-, |
| 71 | Acetic acid, [3,5-bis(trifluoromethyl)-phenoxy]-, |
| 72 | Propanamide, 2-chloro-N-[5-iodo-4-(trifluoromethyl)-2-thiazolyl]-, |
| 73 | Cyclopropanecarbonitrile, 1-[(3,4-dimethylphenyl)thio]-, |
| 74 | Propanenitrile, 3-[[(2-(1,1-dimethylethyl)phenyl]thio]-, |
| 75 | 4-Pentenenitrile, 2-methyl-2-[[(4-(1-methylethyl)phenyl)thio]-, |
| 76 | Ethanimidamide, N'-[(methoxycarbonyl)-oxo]-2-(8-quinolinyloxy)-, |
| 77 | 1(3H)-Isobenzofuranone, 3-[2-(2,5-dimethoxyphenyl)-2-oxoethyl]-, |
| 78 | Acetic acid, 2-(diphenylmethoxy) sodium salt hemihydrate, |
| 79 | Acetic acid, 2-(diphenylmethoxy)- and |
| 80 | Acetic acid, (diphenylmethoxy)-, 2-propanamine salt. |

Greenhouse tests with the above compounds were conducted according to general Procedures I–VIII described below, with modifications noted in the relevant examples.

Procedure I

The following procedure shows interaction between herbicide and antidote when both are incorporated in a soil cover layer before emergence of crop and weed species. Containers were filled and compacted with a fumigated silt loam top soil to a depth of about 1.3 cm from the top of the container. A first container was designated as an untreated control, a second container was designated as a herbicide control, and a third container was designated as a herbicide+antidote test container. Each of the containers was seeded with a crop species. A measured amount of herbicide dispersed or dissolved in acetone was applied to a measured quantity of soil. To this same quantity of soil treated with herbicide, there was added a measured amount of antidote dispersed or dissolved in acetone. The quantity of soil treated with the herbicide and antidote was thoroughly mixed to incorporate the herbicide and antidote in the soil uniformly. The seed bed in the third container of soil was covered with the soil treated with the herbicide and antidote and the container was leveled. For each test series, the seed beds of the first and second containers were likewise covered by soil layers. the cover layer of the first container was not treated with herbicide or antidote. The cover layer of the second container had a measured quantity of herbicide alone incorporated therein.

Insecticide application was made as described in the tests in the examples below. The containers were then placed on a bench in a greenhouse and sub-irrigated as required for the duration of the test. Plant response was observed at various times, but usually about three weeks after initial treatment; variations will be noted in the examples.

Procedure II.

This procedure is the same as Procedure I, but modified in the manner that after incorporation of the chemicals (herbicide, antidote and insecticide), the containers with the covered seedbed were treated with an initial overhead irrigation equivalent to 0.6 cm rainfall, then subsequently sub-irrigated as required on greenhouse benches.

Procedure III.

The following procedure shows interaction between a herbicide and antidote when the antidote is applied in a soil furrow containing crop seed and the herbicide is incorporated in a soil cover layer. Containers were filled and compacted with fumigated silt loam soil to a depth of about 1.3 cm from the top of the container. A first container was designated as an untreated control, a second container was designated as a herbicide control, and a third container was designated as a herbicide+antidote test container. Each container was seeded with crop seed in marked furrows. Antidote compound, dissolved in acetone, was applied directly to the seeded furrows of the third container. Antidote application rate was 0.55 mg active compound per inch of furrow (0.22 mg/cm). This rate was comparable to a plot application rate of 0.28 kilogram per hectare (kg/ha), based on 76 cm (30") spaced-apart furrows. Then, each of the second and third containers was filled and leveled with a cover layer of soil having incorporated therein the selected herbicide at a predetermined concentration. The first container was filled and leveled with soil containing no herbicide. Insecticides were applied in the manner described in the examples below. Pots were overhead irrigated with 0.6 cm (¼"), then placed on a bench in a greenhouse and sub-irrigated as required for the duration of the test. Plant response was observed about three weeks after initial treatment, unless otherwise indicated.

Procedure IV

The following procedure describes interaction among herbicide, biocide and antidote when they are incorporated in a soil cover layer before emergence of crop and weed species. Containers were filled and compacted with a steam sterilized silt loam soil to a depth of about 1.3 cm from the top of the container. A first container was designated as an untreated control, a second container was designated as a herbicide control, a third container was designated as a biocide control, a fourth container as a herbicide+biocide control and a fifth container as a herbicide+biocide+antidote test container. Each of the containers was seeded with a crop species and weed species. A measured amount of herbicide dispersed or dissolved in acetone was applied to a measured quantity of soil. The quantity of soil treated with the herbicide was thoroughly mixed to incorporate the herbicide. A sample of this soil was taken and used to cover the seed bed of the second container. A measured amount of the biocide formulated as granules or an acetone slurry of granules was applied to the soil previously treated with herbicide and this soil was thoroughly mixed to incorporate the biocide. A sample of this soil was taken and used to cover the seed bed of the fourth container. A sample of the remaining soil was taken and a measured amount of antidote dissolved or dispersed in acetone was applied to the soil previously treated with the herbicide and biocide and this soil was thoroughly mixed to incorporate the antidote. This sample of soil was used to cover the seed bed of the fifth container. For each test series, the seed beds of the first and third containers were likewise covered by soil layers. The cover layer of the first container was not treated with herbicide, biocide or antidote. The cover layer of the third container had a measured quantity of biocide alone incorporated therein.

The containers were then placed on a bench in a greenhouse and subirrigated as required for the duration of the test. All treatments were run in duplicate. Plant response was observed at various times, but usually about two weeks after initial treatment. Variations in this procedure will be noted in the examples.

Procedure V

This procedure describes interaction among herbicide, biocide and antidote when the biocide and antidote are incorporated in a soil cover layer before emergence of crop and weed species and the herbicide subsequently applied after emergence of the crop and weeds. The soil, planting method and containers were described in Procedure IV. A measured amount of the biocide formulated as granules or an acetone slurry of granules was applied to a measured quantity of soil. The quantity of soil treated with the biocide was thoroughly mixed to incorporate the biocide. Samples of soil were withdrawn and used to cover the seed beds of the third (biocide control) and fourth (herbicide+biocide control) containers. A sample of the remaining soil was taken and a measured amount of antidote dissolved or dispersed in acetone was applied to the soil previously treated with the biocide and the soil was thoroughly mixed to incorporate the antidote. This sample of soil was used to cover the seed bed of the fifth container (herbicide+biocide+ antidote). For each test series, the seed beds of the first container (untreated control) and second container (herbicide control) were likewise covered by soil layers not treated with biocide or antidote. The containers were then placed on a bench in a greenhouse and subirrigated as required for the duration of the test. The herbicide, dispersed in water containing 0.25% nonionic surfactant (e.g., X-77) was applied by a track sprayer at a rate of approximately 187 L/ha to the emerged plants of the second, third and fourth containers about five days after planting ("DAP" in tables below). All treatments were run in duplicate. Plant response was observed according to Procedure V. Variations in this procedure will be noted in the examples.

Procedure VI

This procedure describes interaction among herbicide, biocide and antidote when the herbicide is incorporated in a soil cover layer and the biocide and the antidote are applied in a soil furrow containing crop seed before emergence of the crop. The soil and seeding depth were described in Procedure IV. A first container was designated as an untreated control, a second container was designated as a herbicide control, a third container was designated as a herbicide+biocide control and a fourth container as a herbicide+biocide+antidote test container. The biocide and antidote were formulated as granules. The biocide was applied to the soil furrows of the third and fourth containers at an application rate of 1.1 mg of active compound per cm of row. The antidote was applied to the soil furrow of the fourth container at an application rate of 0.37 mg of active compound per cm of row. A measured amount of the herbicide dispersed or dissolved in acetone was applied to a measured quantity of soil. The quantity of soil treated with the herbicide was thoroughly mixed to incorporate the herbicide. Samples of this soil were used to cover the seed beds of the second, third and fourth containers. For each test series, the seed bed of the first container was likewise covered by a soil layer not treated with herbicide and without biocide or antidote in the soil furrow.

The containers were then placed on a bench in a greenhouse. Watering was by subirrigation plus overhead irrigation after the plants emerged. All treatments were run in duplicate. Plant response was observed according to Procedure IV. Variations in this procedure will be noted in the examples.

Procedure VII

This procedure describes interaction among herbicide, biocide and antidote when the biocide and the antidote is applied to a soil furrow containing crop seed before emergence of the crop and the herbicide is applied after emergence of the crop and weeds. The soil and planting depth was described in Procedure IV. The containers for comparison, the biocide and antidote applications to soil furrows were described in Procedure VI. In this procedure, the seed beds of the first, second, third and fourth containers are covered by soil layers not treated with herbicide. The containers were then placed on a bench in a greenhouse and subirrigated as required for the duration of the test. The herbicide, dispersed or dissolved in water containing 0.25% v/v nonionic surfactant (X-77) was applied by a track sprayer (187 L/ha) to the emerged plants of the second, third and fourth containers about five days after planting. All treatments were run in duplicate. Plant response was observed according to Procedure IV. Variations in this procedure will be noted in the examples.

Procedure VIII

This procedure describes interaction among herbicide, biocide and antidote when the biocide is applied to a soil furrow containing crop seed before emergence of the crop and the herbicide and antidote are applied after emergence of the crop and weeds. The soil and seeding depth was described in Procedure IV. A first container was designated as an untreated control, a second container was designated as a herbicide control, a third container was designated as a biocide control, a fourth container as herbicide+biocide control and a fifth container as a herbicide+biocide+antidote container. The biocide was formulated as a granule. The biocide was applied to the soil furrows of the third, fourth and fifth containers at an application rate of 1.1 mg of active compound per cm of row. The seed beds of the first through fifth containers were covered by a soil layer of untreated soil. The containers were then placed on a bench in a greenhouse and subirrigated as required for the duration of the test. The antidote, formulated in acetone:water (1:1) containing 0.25% v/v nonionic surfactant (X-77) was applied to the emerged plants of container five by a track sprayer (187 L/ha). Likewise the emerged plants of the second and third containers were sprayed with acetone:water (1:1) containing 0.25% nonionic surfactant (X-77). Similarly, the herbicide dispersed in water containing 0.25% nonionic surfactant (X-77) was applied to emerged plants of the second, fourth and fifth containers. The antidote and herbicide were applied six days after planting. All treatments were run in duplicate. Plant response was observed according to Procedure IV.

In the following examples, the observations for the various tests were made at the indicated times; unless otherwise indicated, all postemergence ("POE") treatments for crops, e.g., corn and weeds were made at the same approximate leaf-stage of development, i.e., at the 1–2 leaf-stage (plants about 7.6 cm to 10.2 cm high) of growth for corn; at the one-half to 2 leaf stage (from 1.3 cm to 5.1 cm high) for the narrow-leaf weed shattercane and for the broadleaf weed velvetleaf, at the cotyledon stage (about 2.5 cm in height) and all test data were the average of duplicate replications.

Where no data is shown in tables for plant response to a given biocidal and/or safener treatment, the reason is that these materials, with few exceptions (not relevant here) are generally safe for use on plants without injury thereto and commercially used as such. For example, terbufos is commercially used without injury to labeled crops.

In the tables of data herein the heading "Biocide" is used in a generic sense to embrace the various utilities, a product is known to have, i.e., as an insecticide, fungicide, nematicide, miticide, etc. For example, without limitation, the compounds terbufos and ethoprop have commercial utility both as an insecticide and as a nematicide. And dimethoate has utility both as a miticide and as an insecticide. These are merely illustrations of the various biological utilities a chemical compound may have. In the more common utility herein included, the biological property of the tested compounds is as an insecticide. However, the particular utility of the compound is of no relevance to the invention herein, which is directed to the prevention, reduction or mitigation of the hyperphytotoxicity (negative synergism) frequently induced in plants by the interaction of a herbicidal compound and a biocidal compound, whatever its intended utility.

In the tables below, the test plants have the following abbreviations:

| | |
|---|---|
| Shattercane | SHCA |
| Giant foxtail | GIFT |
| Velvetleaf | VELE |

EXAMPLE 1

This example was designed to investigate the degree of corn injury by Herbicide No. 1 in contact with Insecticide Nos. 1 and 2 with and without the presence of Antidote No. 1.

The procedures used here involved a combination of Procedures II and III. Granulated Insecticide No. 1 (terbufos) was suspended in water and pipetted in-furrow over corn seeds. Insecticide No. 2 (chlorpyrifos) was sprayed onto cover layers and incorporated therein. Technical grade herbicide and antidote also were pipetted onto the cover layers and incorporated. After spreading the cover layers over the seedbeds, the containers were placed on greenhouse benches to receive 0.6 cm overhead irrigation and subsequent subirrigation as needed. Plant response was evaluated seven (7) weeks after test initiation. Percent injury shown is the mean of three (3) replicates. Results are shown in Table 1. The weed velvetleaf (Abutilon theophrasti) used in this and subsequent tests is abbreviated as "VELE".

TABLE 1

| Treatment | | | | |
|---|---|---|---|---|
| Insecticide No. (Rate) | Antidote No. 1 (Kg/Ha) | Herbicide No. 1 (Kg/Ha) | Percent Injury | |
| | | | Corn | VELE |
| — | — | 0.14 | 18 | 90 |
| — | — | 0.56 | 58 | 95 |
| — | — | 2.24 | 85 | 92 |
| — | 0.14 | 0.14 | 2 | 88 |
| — | 0.56 | 0.56 | 5 | 92 |
| — | 2.24 | 2.24 | 15 | 93 |
| — | 2.24 | — | 0 | 0 |
| 1 (0.23 kg/305 m) | — | 0.14 | 85 | 90 |
| " | — | 0.56 | 97 | 92 |
| " | — | 2.24 | 95 | 95 |
| " | 0.14 | 0.14 | 8 | 87 |
| " | 0.56 | 0.56 | 25 | 90 |
| " | 2.24 | 2.24 | 77 | 92 |
| " | 0.14 | — | 0 | 0 |
| " | 0.56 | — | 0 | 0 |
| " | 2.24 | — | 0 | 0 |
| " | — | — | 0 | 0 |
| 2 (3.36 kg/ha) | — | 0.14 | 60 | 78 |
| " | — | 0.56 | 90 | 92 |
| " | — | 2.24 | 95 | 92 |
| " | 0.14 | 0.14 | 75 | 83 |
| " | 0.56 | 0.56 | 70 | 92 |
| " | 2.24 | 2.24 | 92 | 95 |
| " | 0.14 | — | 0 | 78 |
| " | 0.56 | — | 0 | 33 |
| " | 2.24 | — | 0 | 0 |
| " | — | — | 0 | 0 |
| 1 (H$_2$O) (crystals scattered in-furrow) | — | — | 0 | 0 |
| 1 (H$_2$O) (crystals scattered in-furrow) | 2 | — | 13 | 0 |
| 1 (H$_2$O) (crystals scattered in-furrow) | 2 | 2 | 78 | 95 |

In the data in Table 1, Herbicide No. 1 and Insecticide No. 1 interacted to increase herbicidal injury to corn at 0.14 kg/ha from 18% to 85%, while Insecticide No. 2 increased corn injury to 60%. However, Antidote No. 1 at 0.14 kg/ha reduced the enhanced injury to corn due to Insecticide No. 1 to 8%, although the enhanced injury due to Insecticide No. 2 was not reduced under the test conditions in this example.

EXAMPLE 2

This example describes slight variations and rates of application of the procedures described in Example 1, again using the same herbicidal, insecticidal and antidotal components. In addition Herbicide Nos. 2 and 9 were included.

Insecticide No. 1 was suspended in water as the carrier, and pipetted in-furrow over corn seeds. A 3.36 kg/ha emulsified concentration (EC) of Insecticide No. 2 was applied by broadcasting over cover layers via track sprayer. Formulations of Herbicides No. 2 and 9 were applied via track sprayer; technical grade Herbicide No. 1 and Antidote No. 1 were applied by pipet. The cover layer treatments were applied sequentially and incorporated over the seed beds. Overhead irrigation was applied at a rate of 0.6 cm. Observations were made three (3) weeks after treatment. Results are shown in Table 2.

TABLE 2

| Insecticide No. (Rate) | Antidote No. 1 (Kg/Ha) | Herbicide No. (Kg/Ha) | | | % Injury | |
|---|---|---|---|---|---|---|
| | | 1 | 2 | 9 | Corn | VELE |
| — | — | 0.14 | — | — | 4 | 89 |
| — | — | 0.56 | — | — | 58 | 93 |
| — | 0.14 | 0.14 | — | — | 0 | 86 |
| — | 0.42 | 0.14 | — | — | 8 | 93 |
| — | 0.56 | 0.56 | — | — | 3 | 90 |
| — | 1.68 | 0.56 | — | — | 5 | 95 |
| 1 (0.23 Kg/305 m) | — | 0.14 | — | — | 83 | 83 |
| " | — | 0.56 | — | — | 96 | 95 |
| " | 0.14 | 0.14 | — | — | 18 | 83 |
| " | 0.42 | 0.14 | — | — | 6 | 90 |
| " | 0.56 | 0.56 | — | — | 33 | 95 |
| " | 1.68 | 0.56 | — | — | 34 | 93 |
| 1 (0.11 kg/305 m) | — | 0.14 | — | — | 83 | 93 |
| " | — | 0.56 | — | — | 93 | 94 |
| " | 0.14 | 0.14 | — | — | 26 | 78 |
| " | 0.42 | 0.14 | — | — | 6 | 84 |
| " | 0.56 | 0.56 | — | — | 30 | 93 |
| " | 1.68 | 0.56 | — | — | 18 | 95 |
| 2 (3.36 Kg/Ha) | 0.14 | 0.14 | — | — | 65 | 81 |
| " | 0.56 | 0.56 | — | — | 93 | 95 |
| " | 0.14 | 0.14 | — | — | 24 | 79 |
| " | 0.14 | 0.14 | — | — | 24 | 89 |
| " | 0.56 | 0.56 | — | — | 49 | 95 |
| " | 0.56 | 0.56 | — | — | 30 | 95 |
| 2 (1.68 kg/Ha) | 0.14 | 0.14 | — | — | 70 | 79 |
| " | 0.56 | 0.56 | — | — | 91 | 91 |
| " | 0.14 | 0.14 | — | — | 8 | 91 |
| " | 0.14 | 0.14 | — | — | 5 | 84 |
| " | 0.56 | 0.56 | — | — | 34 | 90 |
| " | 0.56 | 0.56 | — | — | 21 | 89 |
| 2 (3.36 kg/Ha) | — | — | — | — | 8 | 3 |
| 1 (0.23 Kg/305 m) | — | — | — | — | 3 | 0 |
| " | — | — | 4.48 | — | 66 | 0 |
| " | 0.22 | — | 4.48 | — | 5 | 36 |
| " | — | — | 4.48 | — | 93 | 33 |
| " | 0.22 | — | 4.48 | — | 75 | 38 |
| " | — | 0.14 | 4.48 | — | 90 | 95 |
| " | 0.22 | 0.14 | 4.48 | — | 20 | 98 |
| 2 (3.36 Kg/Ha) | — | — | 4.48 | — | 76 | 35 |
| " | 0.22 | — | 4.48 | — | 19 | 11 |
| " | — | 0.14 | 4.48 | — | 83 | 88 |
| " | 0.22 | 0.14 | 4.48 | — | 29 | 83 |
| 1 (0.23 Kg/Ha) | — | — | — | 2.24 | 3 | 88 |
| 2 (3.36 Kg/Ha) | — | — | — | 2.24 | 0 | 30 |

Referring to the data in Table 2, it is noted that the two insecticides both increased herbicidal injury to corn by Herbicide No. 1 at 0.14 kg/ha from 4% to 83% and 65%, respectively. Antidote No. 1 reduced that injury to less than 10% when applied at 3× the herbicide rate. The addition of Herbicide No. 2 at 4.48 kg/ha further increased injury and made safening even more difficult at the applied rate of the antidote. There did not appear to be any significant injury to corn by the combination of the insecticides with atrazine (Herbicide No. 9).

EXAMPLE 3

Using the same general procedures described in Examples 1 and 2, Insecticide Nos. 3 and 4 were formulated in water at a rate of 2.0 ml/75 mg and pipetted in-furrow over the seeds as in Procedure III. Technical grade Herbicide No. 1 and Antidote No. 1 were dissolved in acetone and sequentially pipetted onto cover layers and Herbicide No. 2 in water as an EC was applied via track sprayer. The herbicides and antidote were incorporated into the soil and spread over the insecticide-treated seedbeds. Overhead irrigation was immediately provided to give 0.6 cm simulated rainfall. Observations of plant injury were made three (3) weeks later. Results are shown in Table 3.

TABLE 3

| Insecticide No. (Rate) | Antidote No.1 (Kg/Ha) | Herbicide No. (Kg/Ha) | | | % Injury |
|---|---|---|---|---|---|
| | | 1 | 2 | 9 | Corn |
| — | — | 0.14 | — | — | 10 |
| — | — | 0.56 | — | — | 63 |
| — | 0.14 | 0.14 | — | — | 3 |
| — | 0.42 | 0.14 | — | — | 3 |
| — | 0.56 | 0.56 | — | — | 8 |
| — | 1.68 | 0.56 | — | — | 3 |
| 3 (227 g) | — | 0.14 | — | — | 45 |
| " | — | 0.56 | — | — | 93 |
| " | 0.14 | 0.14 | — | — | 0 |
| " | 0.42 | 0.14 | — | — | 20 |
| " | 1.68 | 0.56 | — | — | 8 |
| 4 (227 g) | — | 0.14 | — | — | 55 |
| " | — | 0.56 | — | — | 45 |
| " | 0.14 | 0.14 | — | — | 3 |
| " | 0.42 | 0.14 | — | — | 5 |
| " | 0.56 | 0.56 | — | — | 28 |
| " | 1.68 | 0.56 | — | — | 5 |
| 3 (227 g) | — | — | — | — | 3 |
| — | — | — | 4.48 | — | 78 |
| — | 0.22 | — | 4.48 | — | 13 |
| 4 (227 g) | — | — | — | — | 5 |
| 3 (227 g) | — | — | 4.48 | — | 83 |
| " | 0.22 | — | 4.48 | — | 25 |
| " | — | 0.14 | 4.48 | — | 73 |
| " | 0.22 | 0.14 | 4.48 | — | 18 |
| 4 (227 g) | — | — | 4.48 | — | 95 |
| " | 0.22 | — | 4.48 | — | 45 |
| " | — | 0.14 | 4.48 | — | 88 |
| " | 0.22 | 0.14 | 4.48 | — | 48 |
| 3 (227 g) | — | — | — | 2.24 | 0 |
| 4 (227 g) | — | — | — | 2.24 | 0 |
| — | — | — | — | 2.24 | 0 |

It will be noted that both Insecticides No. 3 (tefluthrin, a pyrethroid compound) and No. 4 (carbofuran, a carbamate compound), increased corn injury by Herbicide No. 1. At the 0.14 kg/ha rate for Herbicide No. 1, the corn injury was increased from 10% to 45% by Insecticide No. 3 and to 55% by Insecticide No. 4. This negative synergism induced by the interaction of herbicide and insecticide was reduced by Antidote No. 1 at 1:1 ratio to less than 5% in all cases. Moreover, the interaction between Herbicide No. 2 and Insecticide No. 3 resulting in 83% corn injury was reduced to 25% with a 0.22 kg/ha of Antidote No. 1, while the interaction of Herbicide No. 2 with Insecticide No. 4 caused 95% injury. Antidote No. 1 reduced that injury to 45% using only a 0.22 kg/ha rate.

EXAMPLE 4

This example illustrates the interaction between the Insecticide No. 2 (chlorpyrifos) and three sulfonylureas, Herbicide No. 4 (DPX-M6316), No. 5 (chlorimuron ethyl), No. 1 (NC-319) and an imidazolinone compound. Herbicide No. 6 (imazethapyr). Again, Antidote No. 1 was used to evaluate its effect on any negative synergy induced by interaction of herbicide and insecticide.

The procedure used in this test was Procedure No. 2 above. Formulations of herbicide, insecticide and antidote were applied via track sprayer sequentially onto cover layers, incorporated into the soil which was spread over seedbeds, then irrigated from above with 0.6 cm water. Observations were made three (3) weeks after treatment. Results are shown in Table 4.

TABLE 4

| Treatment (kg/Ha) | | | % Injury | |
|---|---|---|---|---|
| Insecticide No. 2 | Antidote No. 1 | Herbicide No. | Corn | VELE |
| — | — | 4 (0.07) | 15 | 10 |
| — | — | 4 (0.14) | 38 | 52 |
| — | 0.07 | 4 (0.07 | 0 | 0 |
| — | 0.14 | 4 (0.14) | 8 | 30 |
| 3.36 | — | 4 (0.07) | 83 | 55 |
| " | 0.07 | 4 (0.07) | 25 | 0 |
| " | — | 4 (0.14) | 80 | 5 |
| " | 0.14 | 4 (0.14) | 88 | 78 |
| — | — | 5 (0.07) | 88 | 57 |
| — | — | 5 (0.14) | 92 | 77 |
| — | 0.07 | 5 (0.07) | 20 | 68 |
| — | 0.14 | 5 (0.14) | 55 | 68 |
| 3.36 | — | 5 (0.07) | 95 | 83 |
| " | 0.07 | 5 (0.07) | 95 | 55 |
| " | — | 5 (0.14) | 98 | 70 |
| " | 0.14 | 5 (0.14) | 95 | 83 |
| — | — | 6 (0.07) | 2 | 33 |
| — | — | 6 (0.14) | 23 | 32 |
| — | 0.07 | 6 (0.07) | 0 | 5 |
| — | 0.14 | 6 (0.14) | 3 | 28 |
| 3.36 | — | 6 (0.07) | 65 | 30 |
| " | 0.07 | 6 (0.07) | 5 | 15 |
| " | — | 6 (0.14) | 43 | 20 |
| " | 0.14 | 6 (0.14) | 63 | 40 |
| — | — | 1 (0.07) | 2 | 20 |
| — | — | 1 (0.14) | 13 | 67 |
| — | 0.07 | 1 (0.07) | 0 | 8 |
| — | 0.14 | 1 (0.14) | 10 | 43 |
| 3.36 | — | 1 (0.07) | 0 | 10 |
| " | 0.07 | 1 (0.07) | 0 | 23 |
| " | — | 1 (0.14) | 38 | 20 |
| " | 0.014 | 1 (0.14) | 0 | 53 |
| " | — | — | 0 | 0 |

The data in Table 4 show that Insecticide No. 2 interacted with each of Herbicide Nos. 4, 5 and 6 to greatly enhance injury to corn. At 3.36 kg/ha corn injury was increased from 15% to 83% with Herbicide No. 4; from 88% to 95% with Herbicide No. 5 and from 2% to 65% with Herbicide No. 6. At the 0.07 kg/ha rate for both Antidote No. 1 and Herbicide 6, corn injury was reduced, respectively, from 83% to 25% and from 65% to 5%. In this test, Antidote No. 1 (0.07 kg/ha) reduced corn injury by Herbicide No. 5 from 88% to 20%, but did not reduce the slightly enhanced injury due to Insecticide No. 2. The effect of both insecticide and antidote on Herbicide No. 1 was negligible in this test.

EXAMPLE 5

In this example tests were conducted to investigate the interaction of Herbicide No. 1 and Insecticide No. 2 with and without Antidote No. 1 in post emergence ("POE") and pre-plant incorporation (PPI) of chemicals.

Said herbicide and antidote were sequentially pipetted onto cover layers, which were spread over the seed beds and subirrigated as in Procedure I and allowed to grow to a height of about 10 cm over a period of 11 days. Herbicide No. 1 and Insecticide No. were then sequentially sprayed on the plant foliage. Observations were made three (3) weeks after initial treatment, 10 days after foliar treatment). Results are shown in Table 5.

TABLE 5

| Treatment (Kg/Ha) | | | | % Injury | |
|---|---|---|---|---|---|
| Insecticide No. 2 | Antidote No. 1 | Herbicide No. 1 | Application Mode | Corn | VELE |
| — | — | 0.14 | PPI | 5 | 78 |
| — | — | 0.56 | " | 28 | 93 |
| — | — | 2.24 | " | 58 | 95 |
| 1.68 | — | 0.14 | " | 18 | 90 |
| " | — | 0.56 | " | 10 | 90 |
| " | — | 2.24 | " | 87 | 98 |
| — | 0.14 | 0.14 | " | 0 | 85 |
| — | 0.56 | 0.56 | " | 5 | 80 |
| — | 2.24 | 2.24 | " | 0 | 93 |
| 1.68 | 0.14 | 0.14 | " | 0 | 90 |
| " | 0.56 | 0.56 | " |  | 93 |
| " | 2.24 | 2.24 | " | 0 | 93 |
| " | 2.24 | — | " | 0 | 0 |
| — | — | 0.07 | POE | 0 | 30 |
| — | — | 0.28 | " | 15 | 30 |
| — | — | 1.12 | " | 7 | 20 |
| 1.68 | — | 0.07 | " | 10 | 23 |
| " | — | 0.28 | " | 10 | 42 |
| " | — | — | " | 35 | 60 |
| 1.68 | — | — | — | 0 | 0 |

The above data indicate that post emergence applications of Insecticide No. 2 increased herbicide injury from both PPI and POE applications of Herbicide No. 1, but not as dramatically as when soil applied. Antidote No. 1 safened PPI herbicide treatments with or without Insecticide No. 2.

EXAMPLE 6

The tests described in this example were to determine the response to Herbicide No. 1 plus insecticides (No. 1 and No. 2) in sensitive (PN3320) and tolerant (PP3377) genotypes of corn.

The procedures in this example were the same as those described in Examples 1–3. The insecticides were formulated in water and pipetted in-furrow over the seeds. Technical grade herbicide and antidote were sequentially pipetted onto cover layers, incorporated and spread over the insecticide-treated pot seedbeds. An overhead irrigation of 0.6 cm was applied immediately after chemical application and the pots subsequently subirrigated on greenhouse benches as needed. Observations of plant response in two replications were taken three (3) weeks after treatment. Results are shown in Table 6; values for corn injury are the mean of duplicate replications.

TABLE 6

| Insecticide No. (Rate) | Antidote No. 1 (Kg/Ha) | Herbicide No. 1 (Kg/Ha) | % Corn Injury | |
|---|---|---|---|---|
| | | | PN 3377 | PN 3320 |
| — | — | — | — | — |
| — | — | 0.14 | 12 | 85 |
| — | — | 0.56 | 23 | 88 |
| — | 0.14 | 0.14 | 15 | 15 |
| — | 0.42 | 0.14 | 0 | 10 |
| — | 0.56 | 0.56 | 0 | 68 |
| — | 1.68 | 0.56 | 0 | 43 |
| 1 (0.23 Kg/305 m) | — | — | 0 | 0 |
| " | — | 0.14 | 78 | 95 |
| " | — | 0.56 | 90 | 95 |
| " | 0.14 | 0.14 | 18 | 40 |
| " | 0.42 | 0.14 | 3 | 25 |
| " | 0.56 | 0.56 | 35 | 40 |
| " | 1.68 | 0.56 | 35 | 35 |
| 2 (0.23 Kg/305 m) | — | — | 0 | 0 |

TABLE 6-continued

| Insecticide No. (Rate) | Antidote No. 1 (Kg/Ha) | Herbicide No. 1 (Kg/Ha) | % Corn Injury | |
|---|---|---|---|---|
| | | | PN 3377 | PN 3320 |
| " | — | 0.14 | 48 | 85 |
| " | — | 0.56 | 90 | 88 |
| " | 0.14 | 0.14 | 0 | 15 |
| " | 0.42 | 0.14 | 13 | 10 |
| " | 0.56 | 0.56 | 10 | 68 |
| " | 1.68 | 0.56 | 28 | 43 |

From the data in Table 6, it is indicated that corn genotype appears to not only affect tolerance to Herbicide No. 1, but also appears to be an important gauge of the extent of interaction with the insecticides. Injury from 0.14 kg/ha herbicide plus Insecticide No. 1 to sensitive corn genotype PN 3320 was safened 74% whereas tolerant genotype PN 3377 corn was safened 96% by Antidote No. 1 at 0.42 kg/ha.

Other greenhouse tests were conducted involving the same chemicals and procedures used in Example 6, to determine any effects from microbial breakdown relative to interactions between the herbicide and insecticides in sterile vs. unsterile soils. It was found that interactions from Insecticide Nos. 1 and 2 did not appear to be reduced in unsterile vs. sterile soil, indicating little insecticide breakdown due to microbes. However, herbicide injury in general was slightly decreased in unsterile soil. This finding comports with reports in the trade that organophosphates are known to suffer microbial breakdown due to soil microbes.

EXAMPLE 7

This example summarizes the results of one series of field trials from a plurality of locations and soil types wherein test chemicals were applied in various modes including pre-plant incorporated (PPI), post emergence (POE) and preemergence (PRE) with and without a safener (antidote). Test Chemicals were Herbicide Nos 1, 2, 3 and 7-9; Insecticide No. 1 and Antidote No. 1.

In these trials Insecticide No. 1 (terbufos) was T-banded or furrow applied at labeled rates prior to planting corn. PPI herbicide treatments were applied prior to insecticide applications; PRE treatments were applied after the insecticide application either prior to or after seeding the corn. POE herbicide applications were made at 2 corn-growth stages, i.e., early post (EP) at the 2-3 leaf stage and late post (LP) at the 4-7 leaf stage. Plots were small plot with 3 replications in a randomized complete block design. In the PRE and PPI herbicide treatments, Antidote No. 1 was applied as a tankmix in both treatments. In the POE herbicide treatments, that antidote was applied as a tank mix with the herbicide at the EP and LP stages.

In summary, as a mean of results from nine disparate locations, in both PRE and PPI application tests, Insecticide No. 1 increased herbicidal injury to corn from combinations of Herbicide No. 1 with Herbicide Nos. 2, 3 and from combinations of Herbicide Nos. 2 and 9. Increased injury expressed itself in terms of malformed plants, stand reduction and growth reduction. At a 1:1 ratio, Herbicide No. 1:Antidote No. 1 and at a 30:1 ratio of Herbicide No. 2:Antidote No. 1, crop injury was reduced from non-commercially-acceptable to commercially-acceptable levels in both PRE and PPI applications. Higher antidote rates of 1:3 (herbicide:antidote) improved corn tolerance even further. Antidote No. 1 provided safening of all crop injury expressions.

In the POE tests, data representing the mean of data from five different locations indicated insignificant interaction between Herbicide No. 1 and Insecticide No. 1 following POE applications of the herbicide following soil applications of the insecticide prior to planting the corn seed. Significant increased growth reduction of corn treated with Insecticide No. 1 occurred following late POE applications of Herbicide No. 8 and early and late POE applications of Herbicide No. 7. In addition, late POE applications of combinations of Herbicide Nos. 1 and 8 resulted in significant interactions with the insecticide.

Antidote No. 1 applied as a tankmix in POE applications, effectively safened insecticide interactions with POE applications of Herbicide No. 7.

The above field trials demonstrated significant negative synergy induced in representative sulfonylurea herbicides with a representative organophosphate insecticide. Also, the field trial data demonstrated that Antidote No. 1, a representative dichloroacetamide antidote, provides effective safening of that negative synergism from POE, PRE and PPI herbicide applications. Antidote No. 1 also effective safened negative synergism in PRE and PPI applications of Herbicide No. 2 (acetochlor) and the OP insecticide. The corn injury/safening described in these field trials refers to commercially-unacceptable to commercial-acceptable performance. The criteria for commercially-acceptable corn injury is equal to or less than about 10% malformed plants or stand reduction and no greater than about 15% growth reduction.

As will be apparent, the data in the above tables reflect the fact that interactions between insecticides and herbicides are susceptible of having their phytotoxicity to crops reduced by antidotal (safener) compounds, while still providing control or suppression of weeds. The data also reflect the common occurrence that the safening effect on various herbicides by safeners will have different degrees of effect depending upon a variety of factors, including, relative concentrations of herbicides and/or co-herbicides and/or antidotes, weather and soil conditions, water content, etc., as well appreciated in the art.

The examples which follow will describe a variety of modes of application of various herbicide, biocide and antidotal compounds to plant loci. Examples 8–20 describe preplant incorporation of the antidote and biocide followed by postemergence application of the herbicide according to Procedure V.

EXAMPLE 8

In this example a variety of antidotal compounds were evaluated for their efficacy against negative synergy induced by the interaction of primisulfuron (Herbicide No. 8), active ingredient in BEACON® herbicide, and terbufos (Biocide No. 1) as the Counter® 15G granule. The safeners and terbufos (in granular form) were applied preplant incorporated ("PPI"), (band) and the herbicide applied postemergence ("POE") in corn in the presence of the weeds shattercane, giant foxtail and velvetleaf according to the description in Procedure V. In this test, five (5) days after PPI application of terbufos and safener, observations of plant response were made to determine the effects of the terbufos and safener, after which the herbicide was applied and observations made eight (8) days later. Plant response is thus reported in Table 7 below for five (5) and thirteen (13) days after planting (DAP) the seeds.

In this test the herbicide was applied at the rate of 0.07 kg/ha of active ingredient and the terbufos was applied at the rate of 8.96 kg/ha active ingredient; the safener rate was either 4.48 kg/ha or 8.96 kg/ha of active ingredient as shown in Table 7.

TABLE 7

| Herb. No. 8 (Kg/Ha) | Biocide No. 1 (Kg/Ha) | Antidote No. | Rate (Kg/Ha) | % Inhibition | | | | | |
|---|---|---|---|---|---|---|---|---|---|
| | | | | 5 DAP | | | 13 DAP | | |
| | | | | Corn | SHCA | VELE | Corn | SHCA | VELE |
| 0.07 | — | — | — | 0 | 0 | 0 | 0 | 80 | 90 |
| " | 8.96 | — | — | 10 | 20 | 0 | 75 | 85 | 95 |
| " | " | 29 | 4.48 | 0 | 40 | 0 | 65 | 80 | 95 |
| " | " | 4 | 8.96 | 10 | 10 | 0 | 60 | 85 | 90 |
| " | " | 5 | " | 15 | 25 | 0 | 40 | 85 | 85 |
| " | " | 77 | " | 0 | 10 | 0 | 75 | 85 | 90 |
| " | " | 30 | 4.48 | 10 | 50 | 75 | 50 | 75 | 95 |
| " | " | 7 | 8.96 | 0 | 0 | 0 | 20 | 80 | 90 |
| " | " | 12 | 4.48 | 20 | 0 | 25 | 15 | 80 | 90 |
| " | " | 15 | 8.96 | 25 | 40 | 50 | 25 | 85 | 85 |
| " | " | 24 | 4.48 | 0 | 0 | 0 | 65 | 85 | 90 |
| " | " | 31 | " | 10 | 0 | 0 | 75 | 80 | 85 |
| " | " | 32 | " | 0 | 30 | 0 | 75 | 85 | 90 |
| " | " | 33 | " | 25 | 20 | 50 | 20 | 90 | 95 |
| " | " | 2 | " | 10 | 0 | 0 | 50 | 85 | 95 |
| " | " | 6 | " | 15 | 20 | 0 | 40 | 90 | 95 |
| " | " | 8 | " | 20 | 0 | 10 | 35 | 90 | 85 |
| " | " | 10 | " | 0 | 0 | 0 | 25 | 75 | 90 |
| " | " | 16 | " | 0 | 0 | 0 | 45 | 90 | 95 |
| " | " | 20 | " | 15 | 0 | 0 | 30 | 75 | 95 |
| " | " | 23 | " | 20 | 0 | 0 | 30 | 85 | 95 |
| " | " | 1 | " | 10 | 0 | 0 | 25 | 80 | 90 |

EXAMPLE 9

This example was a duplicate of the procedure described in Example 8, the only difference being the substitution of the biocide fonofos (No. 9) for terbufos. Fonofos is the active ingredient in DYFONATE® insecticide, used as the 10G granular formulation in this example. Test results are shown in Table 8.

EXAMPLE 10

In another duplication of the procedure described in Examples 8 and 9, the biocide chorpyrifos (Biocide No. 2; active ingredient in LORSBAN® 15G) was used. Test results are shown in Table 9. The only difference in those tests were the dates of application of the chemicals and the dates of making observations.

TABLE 8

| Herb. No. 8 (Kg/Ha) | Biocide No. 9 (Kg/Ha) | Antidote No. | Rate (Kg/Ha) | % Inhibition | | | | | |
|---|---|---|---|---|---|---|---|---|---|
| | | | | 5 DAP | | | 13 DAP | | |
| | | | | Corn | SHCA | VELE | Corn | SHCA | VELE |
| 0.07 | — | — | — | 0 | 0 | 0 | 0 | 75 | 85 |
| " | 8.96 | — | — | 20 | 30 | 0 | 65 | 80 | 90 |
| " | " | 29 | 4.48 | 35 | 40 | 20 | 65 | 85 | 95 |
| " | " | 4 | 8.96 | 15 | 30 | 0 | 30 | 65 | 90 |
| " | " | 5 | " | 20 | 70 | 0 | 35 | 85 | 90 |
| " | " | 77 | " | 15 | 60 | 20 | 65 | 90 | 95 |
| " | " | 30 | 4.48 | 10 | 25 | 80 | 56 | 95 | 95 |
| " | " | 7 | 8.96 | 20 | 20 | 0 | 15 | 75 | 90 |
| " | " | 12 | 4.48 | 20 | 15 | 20 | 20 | 75 | 85 |
| " | " | 15 | 8.96 | 30 | 40 | 60 | 35 | 85 | 90 |
| " | " | 24 | 4.48 | 10 | 20 | 0 | 55 | 80 | 95 |
| " | " | 31 | " | 15 | 20 | 0 | 65 | 80 | 85 |
| " | " | 32 | " | 20 | 30 | 0 | 70 | 80 | 85 |
| " | " | 33 | " | 30 | 70 | 60 | 20 | 90 | 90 |
| " | " | 2 | " | 20 | 20 | 0 | 45 | 85 | 85 |
| " | " | 6 | " | 10 | 30 | 0 | 35 | 80 | 90 |
| " | " | 8 | " | 20 | 30 | 0 | 30 | 80 | 90 |
| " | " | 10 | " | 20 | 30 | 0 | 30 | 70 | 90 |
| " | " | 16 | " | 30 | 30 | 10 | 45 | 80 | 95 |
| " | " | 20 | " | 10 | 0 | 0 | 30 | 85 | 95 |
| " | " | 23 | " | 20 | 30 | 0 | 35 | 75 | 90 |
| " | " | 1 | " | 30 | 20 | 10 | 20 | 75 | 90 |

TABLE 9

| Herb. No. 8 (Kg/Ha) | Biocide No. 2 (Kg/Ha) | Antidote No. | Rate (Kg/Ha) | % Inhibition | | | | | |
|---|---|---|---|---|---|---|---|---|---|
| | | | | 5 DAP | | | 13 DAP | | |
| | | | | Corn | SHCA | VELE | Corn | SHCA | VELE |
| 0.07 | — | — | — | 0 | 0 | 0 | 0 | 80 | 85 |
| " | 8.96 | — | — | 0 | 20 | 0 | 60 | 85 | 90 |
| " | " | 29 | 4.48 | 0 | 10 | 0 | 45 | 90 | 90 |
| " | " | 4 | 8.96 | 0 | 0 | 0 | 40 | 90 | 90 |
| " | " | 5 | " | 0 | 30 | 0 | 25 | 80 | 90 |
| " | " | 77 | " | 0 | 20 | 0 | 70 | 95 | 85 |
| " | " | 30 | 4.48 | 0 | 0 | 90 | 36 | 95 | 95 |
| " | " | 7 | 8.96 | 0 | 0 | 20 | 15 | 90 | 90 |
| " | " | 12 | 4.48 | 0 | 20 | 0 | 10 | 85 | 90 |
| " | " | 15 | 8.96 | 0 | 25 | 50 | 20 | 95 | 95 |
| " | " | 24 | 4.48 | 0 | 0 | 0 | 40 | 85 | 90 |
| " | " | 31 | " | 0 | 0 | 0 | 50 | 90 | 95 |
| " | " | 32 | " | 0 | 30 | 0 | 55 | 85 | 85 |
| " | " | 33 | " | 0 | 30 | 30 | 10 | 95 | 85 |
| " | " | 2 | " | 0 | 0 | 0 | 35 | 85 | 90 |
| " | " | 6 | " | 0 | 20 | 0 | 25 | 85 | 90 |
| " | " | 8 | " | 0 | 30 | 0 | 20 | 90 | 85 |
| " | " | 10 | " | 0 | 40 | 0 | 15 | 90 | 85 |
| " | " | 16 | " | 0 | 0 | 0 | 30 | 85 | 90 |
| " | " | 20 | " | 0 | 0 | 0 | 25 | 80 | 85 |
| " | " | 23 | " | 0 | 0 | 0 | 5 | 80 | 85 |
| " | " | 1 | " | 0 | 10 | 0 | 15 | 80 | 80 |

EXAMPLE 11

The test conducted in this example was similar to that conducted in Example 10, including the dates of application of chemicals and taking observations. The sole difference was that thimet was used instead of chlorpyrifos and the herbicide rate was increased to 0.14 kg/ha. Thimet® 10G (also known as "phorate") is Biocide No. 10 in the above list of biocides. Test results are shown in Table 10.

TABLE 10

| Herb. No. 8 (Kg/Ha) | Biocide No. 10 (Kg/Ha) | Antidote No. | Rate (Kg/Ha) | % Inhibition | | | | | |
|---|---|---|---|---|---|---|---|---|---|
| | | | | 5 DAP | | | 13 DAP | | |
| | | | | Corn | SHCA | VELE | Corn | SHCA | VELE |
| 0.14 | 8.96 | — | — | 0 | 0 | 0 | 0 | 90 | 95 |
| " | 8.96 | — | — | 0 | 30 | 0 | 30 | 90 | 95 |
| " | " | 29 | 4.48 | 0 | 10 | 0 | 25 | 95 | 95 |
| " | " | 4 | 8.96 | 0 | 0 | 0 | 20 | 90 | 95 |
| " | " | 5 | " | 0 | 0 | 0 | 15 | 85 | 95 |
| " | " | 77 | " | 0 | 0 | 0 | 35 | 90 | 95 |
| " | " | 30 | 4.48 | 0 | 20 | 90 | 25 | 95 | 95 |
| " | " | 7 | 8.96 | 0 | 0 | 0 | 10 | 85 | 90 |
| " | " | 12 | 4.48 | 0 | 0 | 0 | 0 | 85 | 90 |
| " | " | 15 | 8.96 | 20 | 20 | 50 | 15 | 90 | 95 |
| " | " | 24 | 4.48 | 0 | 0 | 0 | 20 | 85 | 95 |
| " | " | 31 | " | 0 | 0 | 0 | 25 | 80 | 95 |
| " | " | 32 | " | 0 | 20 | 0 | 35 | 90 | 95 |
| " | " | 33 | " | 0 | 20 | 30 | 5 | 90 | 95 |
| " | " | 2 | " | 0 | 0 | 0 | 20 | 90 | 95 |
| " | " | 6 | " | 0 | 0 | 0 | 10 | 85 | 95 |
| " | " | 8 | " | 0 | 0 | 0 | 15 | 80 | 90 |
| " | " | 10 | " | 0 | 0 | 0 | 15 | 80 | 95 |
| " | " | 16 | " | 0 | 40 | 0 | 15 | 95 | 95 |
| " | " | 20 | " | 0 | 0 | 0 | 10 | 95 | 90 |
| " | " | 23 | " | 0 | 30 | 0 | 5 | 85 | 95 |
| " | " | 1 | " | 0 | 0 | 0 | 10 | 85 | 95 |

Referring to the test data in Tables 8–10, most of the antidotes were active in reducing corn injury arising from the interaction of the biocide and the later-applied herbicide. The most active antidotes were Nos. 1, 12 and 33. Other more active antidotes were Nos. 6–8, 10, 20 and 23. In these tests Antidote Nos. 31, 32 and 77 were either inactive or weakly active. Fifteen of the antidotes provided significant activity (i.e., >20%) at least 75% of the time. Control of the test weeds with primisulfuron with or without the biocides and antidotes was at expected levels.

Evaluations of plant response to the biocides and safeners before application of the herbicide did not show significant harmful effect on the corn. For example, COUNTER and DYFONATE caused slight early stunting and leaf malformation to corn. Some injury was noted with combinations including Antidote Nos. 15, 30 and 33.

In a set of experiments parallel to those described in Examples 8–11, the same Procedure V was conducted, but using different herbicidal components and dates of PPI planting of biocide and antidote, POE application of herbicide and observation as described in Examples 12–15 below.

EXAMPLE 12

In this example Herbicide No. 7, viz. ACCENT®, was used; active ingredient is nicosulfuron. The biocide was No. 1 (COUNTER 15G). The herbicide was applied POE at the above-mentioned leaf-stage of growth of the plants five (5) days after planting the seed and observations were made eight (8) days later, i.e., thirteen (13) days after planting. Test results are shown in Table 11.

TABLE 11

| Herbicide No. 7 | Biocide No. 1 | Antidote | Rate | % Inhibition | | |
|---|---|---|---|---|---|---|
| (Kg/Ha) | (Kg/Ha) | No. | (Kg/Ha) | Corn | SHCA | VELE |
| 0.28 | — | — | — | 0 | 70 | 60 |
| " | 8.96 | — | — | 60 | 75 | 65 |
| " | " | 29 | 4.48 | 60 | 70 | 70 |
| " | " | 4 | 8.96 | 50 | 75 | 70 |
| " | " | 5 | " | 30 | 75 | 75 |
| " | " | 77 | " | 25 | 70 | 65 |
| " | " | 30 | 4.48 | 55 | 85 | 95 |
| " | " | 7 | 8.96 | 30 | 80 | 75 |
| " | " | 12 | 4.48 | 20 | 75 | 65 |
| " | " | 15 | 8.96 | 40 | 85 | 80 |
| " | " | 24 | 4.48 | 45 | 70 | 60 |
| " | " | 31 | " | 65 | 75 | 65 |
| " | " | 32 | " | 55 | 70 | 65 |
| " | " | 33 | " | 15 | 70 | 70 |
| " | " | 2 | " | 30 | 75 | 65 |
| " | " | 6 | " | 35 | 65 | 65 |
| " | " | 8 | " | 35 | 60 | 65 |
| " | " | 10 | " | 30 | 80 | 75 |
| " | " | 16 | " | 40 | 70 | 65 |
| " | " | 20 | " | 30 | 75 | 70 |
| " | " | 23 | " | 35 | 65 | 65 |
| " | " | 1 | " | 20 | 75 | 70 |
| — | " | — | — | 5 | 25 | 0 |

EXAMPLE 13

The same procedure described for Example 12 was conducted using the same herbicide and antidotes but using 0.56 kg/ha of ACCENT herbicide and a different biocide, viz. Biocide No. 9 (DYFONATE 10G). Chemicals were applied as in Example 12. Test data are reported in Table 12.

TABLE 12

| Herbicide No. 7 | Biocide No. 9 | Antidote | Rate | % Inhibition | | |
|---|---|---|---|---|---|---|
| (Kg/Ha) | (Kg/Ha) | No. | (Kg/Ha) | Corn | SHCA | VELE |
| 0.56 | — | — | — | 0 | 75 | 60 |
| " | 8.96 | — | — | 55 | 80 | 70 |
| " | " | 29 | 4.48 | 50 | 80 | 70 |
| " | " | 4 | 8.96 | 30 | 70 | 65 |
| " | " | 5 | " | 30 | 75 | 65 |
| " | " | 77 | " | 35 | 85 | 75 |
| " | " | 30 | 4.48 | 50 | 90 | 100 |
| " | " | 7 | 8.96 | 40 | 85 | 65 |
| " | " | 12 | 4.48 | 10 | 65 | 70 |
| " | " | 15 | 8.96 | 40 | 95 | 85 |
| " | " | 24 | 4.48 | 30 | 70 | 65 |
| " | " | 31 | " | 40 | 85 | 75 |
| " | " | 32 | " | 65 | 85 | 70 |
| " | " | 33 | " | 20 | 75 | 70 |
| " | " | 2 | " | 35 | 80 | 70 |
| " | " | 6 | " | 30 | 75 | 60 |

TABLE 12-continued

| Herbicide No. 7 | Biocide No. 9 | Antidote | Rate | % Inhibition | | |
|---|---|---|---|---|---|---|
| (Kg/Ha) | (Kg/Ha) | No. | (Kg/Ha) | Corn | SHCA | VELE |
| " | " | 8 | " | 30 | 85 | 70 |
| " | " | 10 | " | 40 | 80 | 70 |
| " | " | 16 | " | 25 | 75 | 65 |
| " | " | 20 | " | 35 | 75 | 70 |
| " | " | 23 | " | 30 | 85 | 70 |
| " | " | 1 | " | 25 | 80 | 75 |
| — | " | — | — | 5 | 20 | 10 |

EXAMPLE 14

The procedure in the preceding examples was repeated using, however, Biocide No. 2 (LORSBAN® 15G). Planting of seeds and application of chemicals were at a different time than in Example 13, but the intervals between planting, application of herbicide and observation times were the same. In this example the ACCENT application rate was again 0.02 kg/ha as in Example 12. Test data are reported in Table 13.

TABLE 13

| Herbicide No. 7 | Biocide No. 2 | Antidote | Rate | % Inhibition | | |
|---|---|---|---|---|---|---|
| (Kg/Ha) | (Kg/Ha) | No. | (Kg/Ha) | Corn | SHCA | VELE |
| 0.28 | — | — | — | 0 | 75 | 60 |
| " | 8.96 | — | — | 45 | 90 | 70 |
| " | " | 29 | 4.48 | 35 | 85 | 65 |
| " | " | 4 | 8.96 | 25 | 90 | 70 |
| " | " | 5 | " | 15 | 90 | 60 |
| " | " | 77 | " | 15 | 95 | 70 |
| " | " | 30 | 4.48 | 25 | 90 | 100 |
| " | " | 7 | 8.96 | 20 | 90 | 65 |
| " | " | 12 | 4.48 | 0 | 90 | 75 |
| " | " | 15 | 8.96 | 20 | 90 | 80 |
| " | " | 24 | 4.48 | 30 | 90 | 65 |
| " | " | 31 | " | 30 | 85 | 65 |
| " | " | 32 | " | 25 | 95 | 70 |
| " | " | 33 | " | 10 | 90 | 70 |
| " | " | 2 | " | 15 | 90 | 60 |
| " | " | 6 | " | 15 | 90 | 70 |
| " | " | 8 | " | 20 | 90 | 70 |
| " | " | 10 | " | 10 | 90 | 60 |
| " | " | 16 | " | 30 | 90 | 65 |
| " | " | 20 | " | 10 | 90 | 65 |
| " | " | 23 | " | 15 | 85 | 70 |
| " | " | 1 | " | 5 | 90 | 70 |
| — | " | — | — | 0 | 25 | 0 |

EXAMPLE 15

Another test conducted as in Example 14 was repeated but modified only to use Biocide No. 10 (THIMET 20G) and increase the herbicide rate to 0.84 kg/ha. Test results are shown in Table 14.

TABLE 14

| Herbicide No. 7 | Biocide No. 2 | Antidote | Rate | % Inhibition | | |
|---|---|---|---|---|---|---|
| (Kg/Ha) | (Kg/Ha) | No. | (Kg/Ha) | Corn | SHCA | VELE |
| 0.84 | — | — | — | 0 | 75 | 65 |
| " | 8.96 | — | — | 40 | 70 | 65 |
| " | " | 29 | 4.48 | 35 | 80 | 70 |
| " | " | 4 | 8.96 | 15 | 70 | 65 |
| " | " | 5 | " | 10 | 70 | 70 |
| " | " | 77 | " | 25 | 85 | 70 |

TABLE 14-continued

| Herbicide No. 7 (Kg/Ha) | Biocide No. 2 (Kg/Ha) | Anti-dote No. | Rate (Kg/Ha) | % Inhibition Corn | SHCA | VELE |
|---|---|---|---|---|---|---|
| " | " | 30 | 4.48 | 30 | 90 | 100 |
| " | " | 7 | 8.96 | 25 | 75 | 70 |
| " | " | 12 | 4.48 | 0 | 75 | 70 |
| " | " | 15 | 8.96 | 25 | 95 | 80 |
| " | " | 24 | 4.48 | 20 | 80 | 65 |
| " | " | 31 | " | 45 | 75 | 65 |
| " | " | 32 | " | 35 | 70 | 60 |
| " | " | 33 | " | 0 | 75 | 75 |
| " | " | 2 | " | 20 | 75 | 70 |
| " | " | 6 | " | 15 | 75 | 75 |
| " | " | 8 | " | 20 | 85 | 70 |
| " | " | 10 | " | 20 | 70 | 65 |
| " | " | 16 | " | 20 | 70 | 65 |
| " | " | 20 | " | 25 | 70 | 70 |
| " | " | 23 | " | 10 | 60 | 65 |
| " | " | 1 | " | 5 | 70 | 65 |
| — | " | — | — | 0 | 0 | 0 |

From the data in Tables 11–14, it is seen that substantial corn injury (40 to 60%) resulted from treatments with 8.96 kg/ha of biocides (OP insecticides) followed by POE applications of ACCENT herbicide, resulting in enhanced herbicidal activity. By itself, with no insecticide present ACCENT, at rates within the range of 0.28 to 0.84 kg/ha was completely safe to corn.

Significant reduction in corn injury was seen with many of the test safeners. The most active safeners in these tests were Antidote Nos. 1, 12 and 33. Antidote Nos. 11 and 7, both milo seed protectants, had similar activity.

In most cases, control of the weeds shattercane and velvetleaf with safened combinations was at expected or slightly elevated levels.

In another set of experiments, using Procedure V, another herbicide, i.e., PURSUIT® (No. 18) was used to evaluate any interaction resulting from contact thereof with the same biocides used in Examples 8–15 and the safening effect of the same antidotes used in those examples. These experiments are described in Examples 16–19 below. In those experiments, the only changes in Examples 18 and 19 were different dates for planting, herbicide application and observation of plant response.

EXAMPLE 16

In this test, the insecticide COUNTER® 15G was, together with the test antidotes planted by PPI, then five (5) days later, the herbicide, PURSUIT® 15G (active ingredient imazapyr), was applied POE and ten (10) days thereafter, plant response was observed and recorded. Because of its inherent high unit activity, the rate of application of PURSUIT was reduced to 0.0175 kg/ha. Test data are reported in Table 15.

TABLE 15

| Herbicide No. 18 (Kg/Ha) | Biocide No. 1 (Kg/Ha) | Anti-dote No. | Rate (Kg/Ha) | % Inhibition Corn | SHCA | VELE |
|---|---|---|---|---|---|---|
| 0.0175 | — | — | — | 10 | 60 | 80 |
| " | 8.96 | — | — | 75 | 65 | 80 |
| " | " | 29 | 4.48 | 75 | 60 | 75 |

TABLE 15-continued

| Herbicide No. 18 (Kg/Ha) | Biocide No. 1 (Kg/Ha) | Anti-dote No. | Rate (Kg/Ha) | % Inhibition Corn | SHCA | VELE |
|---|---|---|---|---|---|---|
| " | " | 4 | 8.96 | 65 | 65 | 80 |
| " | " | 5 | " | 55 | 55 | 80 |
| " | " | 77 | " | 20 | 60 | 80 |
| " | " | 30 | 4.48 | 70 | 70 | 95 |
| " | " | 7 | 8.96 | 65 | 55 | 80 |
| " | " | 12 | 4.48 | 60 | 60 | 90 |
| " | " | 15 | 8.96 | 45 | 60 | 80 |
| " | " | 24 | 4.48 | 70 | 65 | 85 |
| " | " | 31 | " | 70 | 65 | 80 |
| " | " | 32 | " | 70 | 50 | 80 |
| " | " | 33 | " | 40 | 55 | 85 |
| " | " | 2 | " | 60 | 65 | 80 |
| " | " | 6 | " | 60 | 65 | 85 |
| " | " | 8 | " | 45 | 60 | 75 |
| " | " | 10 | " | 60 | 55 | 85 |
| " | " | 16 | " | 65 | 65 | 90 |
| " | " | 20 | " | 60 | 60 | 85 |
| " | " | 23 | " | 65 | 65 | 85 |
| " | " | 1 | " | 55 | 55 | 80 |
| — | " | — | — | 0 | 20 | 15 |

EXAMPLE 17

In this example, the biocide was DYFONATE 10G. All other test conditions were the same as in Example 16. Test results are shown in Table 16.

TABLE 16

| Herbicide No. 18 (Kg/Ha) | Biocide No. 9 (Kg/Ha) | Anti-dote No. | Rate (Kg/Ha) | % Inhibition Corn | SHCA | VELE |
|---|---|---|---|---|---|---|
| 0.0175 | — | — | — | 5 | 40 | 65 |
| " | 8.96 | — | — | 45 | 60 | 70 |
| " | " | 29 | 4.48 | 35 | 75 | 75 |
| " | " | 4 | 8.96 | 35 | 55 | 70 |
| " | " | 5 | " | 25 | 40 | 65 |
| " | " | 77 | " | 15 | 55 | 70 |
| " | " | 30 | 4.48 | 35 | 60 | 100 |
| " | " | 7 | 8.96 | 30 | 50 | 75 |
| " | " | 12 | 4.48 | 20 | 55 | 65 |
| " | " | 15 | 8.96 | 15 | 50 | 75 |
| " | " | 24 | 4.48 | 30 | 55 | 65 |
| " | " | 31 | " | 45 | 50 | 70 |
| " | " | 32 | " | 55 | 55 | 70 |
| " | " | 33 | " | 10 | 60 | 80 |
| " | " | 2 | " | 25 | 45 | 70 |
| " | " | 6 | " | 25 | 50 | 70 |
| " | " | 8 | " | 30 | 45 | 75 |
| " | " | 10 | " | 20 | 60 | 70 |
| " | " | 16 | " | 35 | 40 | 75 |
| " | " | 20 | " | 25 | 50 | 65 |
| " | " | 23 | " | 30 | 60 | 75 |
| " | " | 1 | " | 40 | 55 | 65 |
| — | " | — | — | 10 | 25 | 0 |

EXAMPLE 18

The procedure in the preceding example was followed except the insecticide was LORSBAN® 15G (Antidote No. 2), and, as noted above, the dates for planting, herbicide application and plant observation were different in this example; observation was nine (9) days after herbicide application. Results are show in Table 17.

TABLE 17

| Herbicide No. 18 | Biocide No. 2 | Antidote No. | Rate | % Inhibition | | |
|---|---|---|---|---|---|---|
| (Kg/Ha) | (Kg/Ha) | | (Kg/Ha) | Corn | SHCA | VELE |
| 0.0175 | — | — | — | 15 | 65 | 80 |
| " | 8.96 | — | — | 65 | 65 | 80 |
| " | " | 29 | 4.48 | 65 | 65 | 75 |
| " | " | 4 | 8.96 | 60 | 60 | 80 |
| " | " | 5 | " | 30 | 65 | 80 |
| " | " | 77 | " | 30 | 65 | 85 |
| " | " | 30 | 4.48 | 35 | 70 | 95 |
| " | " | 7 | 8.96 | 60 | 65 | 80 |
| " | " | 12 | 4.48 | 35 | 80 | 75 |
| " | " | 15 | 8.96 | 20 | 75 | 85 |
| " | " | 24 | 4.48 | 55 | 70 | 80 |
| " | " | 31 | " | 60 | 60 | 75 |
| " | " | 32 | " | 65 | 65 | 75 |
| " | " | 33 | " | 25 | 75 | 80 |
| " | " | 2 | " | 55 | 50 | 85 |
| " | " | 6 | " | 50 | 65 | 80 |
| " | " | 8 | " | 55 | 55 | 90 |
| " | " | 10 | " | 45 | 65 | 80 |
| " | " | 16 | " | 60 | 65 | 85 |
| " | " | 20 | " | 55 | 60 | 80 |
| " | " | 23 | " | 50 | 65 | 85 |
| " | " | 1 | " | 45 | 60 | 80 |
| — | " | — | — | 0 | 30 | 0 |

EXAMPLE 19

The identical procedure described in Example 18 was conducted, except for use of the insecticide THIMET 20G (Antidote No. 10) here. Results are shown in Table 18.

TABLE 18

| Herbicide No. 18 | Biocide No. 10 | Antidote No. | Rate | % Inhibition | | |
|---|---|---|---|---|---|---|
| (Kg/Ha) | (Kg/Ha) | | (Kg/Ha) | Corn | SHCA | VELE |
| 0.0175 | — | — | — | 10 | 45 | 85 |
| " | 8.96 | — | — | 55 | 40 | 80 |
| " | " | 29 | 4.48 | 45 | 45 | 80 |
| " | " | 4 | 8.96 | 40 | 45 | 85 |
| " | " | 5 | " | 10 | 40 | 75 |
| " | " | 77 | " | 15 | 45 | 85 |
| " | " | 30 | 4.48 | 40 | 70 | 100 |
| " | " | 7 | 8.96 | 40 | 50 | 85 |
| " | " | 12 | 4.48 | 25 | 50 | 85 |
| " | " | 15 | 8.96 | 15 | 65 | 85 |
| " | " | 24 | 4.48 | 35 | 55 | 80 |
| " | " | 31 | " | 55 | 45 | 80 |
| " | " | 32 | " | 45 | 40 | 80 |
| " | " | 33 | " | 0 | 35 | 85 |
| " | " | 2 | " | 30 | 30 | 85 |
| " | " | 6 | " | 35 | 50 | 80 |
| " | " | 8 | " | 30 | 35 | 80 |
| " | " | 10 | " | 20 | 45 | 85 |
| " | " | 16 | " | 40 | 40 | 85 |
| " | " | 20 | " | 30 | 35 | 85 |
| " | " | 23 | " | 40 | 55 | 80 |
| " | " | 1 | " | 20 | 35 | 80 |
| — | " | — | — | 0 | 25 | 20 |

From the above series of tests to evaluate the safening effect of various antidotes on the negative synergy induced by the interaction of commercial insecticide applied PPI, followed by POE application of PURSUIT® herbicide, it is noted that severe corn injury did, in fact, result from said negative synergy. On the order of magnitude from 10% to 75% corn injury following interaction between PURSUIT and COUNTER.

Lesser, but increased corn injury (45% up to 65%) also resulted from the interaction of PURSUIT with DYFONATE, LORSBAN and THIMET.

The most active safeners in these tests were Nos. 11, 15 and 33. Of note, Antidote No. 11, was substantially more effective than No. 11 (flurazole, a commercial seed protectant for milo against acetanilide herbicide injury).

Control of the weeds was generally at expected levels for safened combinations of antidotes with PURSUIT.

In the preceding sets of tests, the herbicide application mode was postemergence according to Procedure V. Other sets of tests were conducted using the PPI method of herbicide application according to Procedure IV described above. In these tests, described in Examples 20–27 below, Herbicide Nos. 1 (NC-319; also, MON-12000) and 21 (XRD-498) were similarly contacted with COUNTER, DYFONATE, LORSBAN and THIMET insecticides and the same group of antidotes used in Examples 8–19. The only procedural difference in these examples is the dates on which the tests were initiated and plant response observations were made; intervals between those events were the same (11 or 12 days). In all of these tests the herbicide application rate was 0.14 kg/ha; the biocide rate was 8.96 kg/ha and the antidote rate was 4.48 kg/ha or 8.96 kg/ha.

EXAMPLE 20

Following the procedure described in Procedure IV above, the antidotes used in the preceding POE herbicide application tests were evaluated for the efficacy against negative synergy induced by the in-soil contact between Herbicide No. 1 (MON-12000) and COUNTER 15G (Antidote No. 1). In this and the following examples the test plant spectrum included corn, giant foxtail (GIFT) and velvetleaf (VELE). Test results are shown in Table 19.

TABLE 19

| Herbicide No. 1 | Biocide No. 1 | Antidote No. | Rate | % Inhibition | | |
|---|---|---|---|---|---|---|
| (Kg/Ha) | (Kg/Ha) | | (Kg/Ha) | Corn | GIFT | VELE |
| 0.0175 | — | — | — | 5 | 15 | 85 |
| " | 8.96 | — | — | 50 | 60 | 95 |
| " | " | 29 | 4.48 | 40 | 55 | 90 |
| " | " | 4 | 8.96 | 30 | 50 | 90 |
| " | " | 5 | " | 15 | 30 | 85 |
| " | " | 77 | " | 50 | 60 | 95 |
| " | " | 30 | 4.48 | 30 | 65 | 90 |
| " | " | 7 | 8.96 | 15 | 55 | 80 |
| " | " | 12 | 4.48 | 5 | 45 | 90 |
| " | " | 15 | 8.96 | 20 | 50 | 85 |
| " | " | 24 | 4.48 | 25 | 45 | 90 |
| " | " | 31 | " | 35 | 55 | 85 |
| " | " | 32 | " | 15 | 30 | 75 |
| " | " | 33 | " | 20 | 40 | 85 |
| " | " | 2 | " | 30 | 50 | 90 |
| " | " | 6 | " | 10 | 50 | 95 |
| " | " | 8 | " | 20 | 45 | 90 |
| " | " | 10 | " | 5 | 40 | 85 |
| " | " | 16 | " | 20 | 40 | 85 |
| " | " | 20 | " | 15 | 40 | 90 |
| " | " | 23 | " | 10 | 50 | 95 |
| " | " | 1 | " | 20 | 45 | 90 |
| — | " | — | — | 5 | 10 | 0 |

EXAMPLE 21

The test reported in this example was a duplicate of that in the preceding example, but for substitution of DYFONATE 10G as the biocidal component. The test data for this example is shown in Table 20.

TABLE 20

| Herbicide No. 1 (Kg/Ha) | Biocide No. 9 (Kg/Ha) | Antidote No. | Rate (Kg/Ha) | % Inhibition Corn | % Inhibition GIFT | % Inhibition VELE |
|---|---|---|---|---|---|---|
| 0.0175 | — | — | — | 0 | 0 | 80 |
| " | 8.96 | — | — | 45 | 65 | 90 |
| " | " | 29 | 4.48 | 35 | 75 | 90 |
| " | " | 4 | 8.96 | 25 | 65 | 95 |
| " | " | 5 | " | 35 | 70 | 95 |
| " | " | 77 | " | 55 | 95 | 95 |
| " | " | 30 | 4.48 | 30 | 80 | 95 |
| " | " | 7 | 8.96 | 30 | 60 | 85 |
| " | " | 12 | 4.48 | 5 | 65 | 80 |
| " | " | 15 | 8.96 | 45 | 85 | 90 |
| " | " | 24 | 4.48 | 40 | 70 | 85 |
| " | " | 31 | " | 25 | 80 | 85 |
| " | " | 32 | " | 40 | 60 | 95 |
| " | " | 33 | " | 25 | 75 | 85 |
| " | " | 2 | " | 20 | 55 | 90 |
| " | " | 6 | " | 15 | 55 | 90 |
| " | " | 8 | " | 25 | 50 | 85 |
| " | " | 10 | " | 15 | 55 | 85 |
| " | " | 16 | " | 15 | 60 | 90 |
| " | " | 20 | " | 25 | 60 | 90 |
| " | " | 23 | " | 20 | 60 | 95 |
| " | " | 1 | " | 25 | 60 | 90 |
| — | " | — | — | 5 | 35 | 25 |

EXAMPLE 22

This example was conducted according to the procedure of the preceding two examples, except for a one-day difference on the test initiation and plant observation dates. The biocide used in this test was LORSBAN 15G. Data are shown in Table 21.

TABLE 21

| Herbicide No. 1 (Kg/Ha) | Biocide No. 2 (Kg/Ha) | Antidote No. | Rate (Kg/Ha) | % Inhibition Corn | % Inhibition Gift | % Inhibition VELE |
|---|---|---|---|---|---|---|
| 0.0175 | — | — | — | 0 | 0 | 80 |
| " | 8.96 | — | — | 45 | 80 | 80 |
| " | " | 29 | 4.48 | 40 | 75 | 85 |
| " | " | 4 | 8.96 | 10 | 65 | 70 |
| " | " | 5 | " | 20 | 70 | 80 |
| " | " | 77 | " | 55 | 85 | 60 |
| " | " | 30 | 4.48 | 10 | 90 | 95 |
| " | " | 7 | 8.96 | 30 | 80 | 85 |
| " | " | 12 | 4.48 | 5 | 75 | 70 |
| " | " | 15 | 8.96 | 15 | 85 | 85 |
| " | " | 24 | 4.48 | 50 | 85 | 85 |
| " | " | 31 | " | 40 | 85 | 80 |
| " | " | 32 | " | 50 | 80 | 90 |
| " | " | 33 | " | 15 | 75 | 80 |
| " | " | 2 | " | 25 | 80 | 80 |
| " | " | 6 | " | 30 | 80 | 85 |
| " | " | 8 | " | 20 | 85 | 80 |
| " | " | 10 | " | 20 | 75 | 90 |
| 0.0175 | 8.96 | 16 | 4.48 | 10 | 80 | 70 |
| " | " | 20 | " | 30 | 80 | 80 |
| " | " | 23 | " | 5 | 80 | 80 |
| " | " | 1 | " | 10 | 85 | 80 |
| — | " | — | — | 0 | 45 | 0 |

EXAMPLE 23

This test was conducted simultaneously with that in Example 22, except using THIMET 20G as the biocidal component. Test results are shown in Table 22.

TABLE 22

| Herbicide No. 1 (Kg/Ha) | Biocide No. 10 (Kg/Ha) | Antidote No. | Rate (Kg/Ha) | % Inhibition Corn | % Inhibition Gift | % Inhibition VELE |
|---|---|---|---|---|---|---|
| 0.0175 | — | — | — | 0 | 0 | 85 |
| " | 8.96 | — | — | 50 | 65 | 90 |
| " | " | 29 | 4.48 | 40 | 75 | 90 |
| " | " | 4 | 8.96 | 20 | 60 | 90 |
| " | " | 5 | " | 10 | 45 | 90 |
| " | " | 77 | " | 45 | 80 | 95 |
| " | " | 30 | 4.48 | 30 | 75 | 90 |
| " | " | 7 | 8.96 | 20 | 70 | 90 |
| " | " | 12 | 4.48 | 15 | 50 | 95 |
| " | " | 15 | 8.96 | 35 | 70 | 95 |
| " | " | 24 | 4.48 | 35 | 55 | 90 |
| " | " | 31 | " | 50 | 75 | 85 |
| " | " | 32 | " | 35 | 65 | 85 |
| " | " | 33 | " | 15 | 60 | 85 |
| " | " | 2 | " | 20 | 60 | 90 |
| " | " | 6 | " | 15 | 55 | 90 |
| " | " | 8 | " | 20 | 65 | 90 |
| " | " | 10 | " | 15 | 60 | 95 |
| 0.0175 | 8.96 | 16 | 4.48 | 25 | 55 | 85 |
| " | " | 20 | " | 10 | 75 | 90 |
| " | " | 23 | " | 5 | 60 | 90 |
| " | " | 1 | " | 15 | 65 | 95 |
| — | " | — | — | 5 | 30 | 15 |

In the above series of tests conducted in Examples 20–23, wherein the safening effect of the indicated antidotes was evaluated against negative synergy induced by the interaction of commercial biocides (OP insecticides) with Herbicide No. 1 (MON-12000), it was noted that combinations of MON-12000 at 0.14 kg/ha with the OP insecticides at 8.96 kg/ha increased corn injury from 0–5% up to 45–50%. Safening activity was observed with many of the antidotes, notably Antidote Nos. 12 (MON-7400), 23 and 33. In these tests the safening activity of No. 77 was low or nil.

The insecticides applied alone caused some stunting of giant foxtail; this response was substantially increased by the addition of MON-12000. With few exceptions, the antidotes did not reduce control of giant foxtail or velvetleaf with combinations of MON-12000+insecticides.

Another series of tests was conducted to evaluate the safening effect of the same biocides/insecticides and antidotes used in preceding examples, except substituting Herbicide No. 21 (XRD-498); as the herbicidal component. Procedure IV was also used in the series of tests described in Examples 24–27 below. PPI initiation and plant observation dates in Examples 26 and 27 were one day later than those in Examples 24 and 25, otherwise, the tests were identical.

EXAMPLE 24

In this test, the herbicidal component was XRD-498, the biocidal component COUNTER 15G and the antidotes were those used in the preceding examples. Test data is shown in Table 23.

TABLE 23

| Herbicide No. 21 (Kg/Ha) | Biocide No. 1 (Kg/Ha) | Antidote No. | Rate (Kg/Ha) | % Inhibition Corn | % Inhibition Gift | % Inhibition VELE |
|---|---|---|---|---|---|---|
| 0.0175 | — | — | — | 0 | 0 | 60 |
| " | 8.96 | — | — | 50 | 60 | 70 |
| " | " | 29 | 4.48 | 40 | 65 | 65 |
| " | " | 4 | 8.96 | 35 | 60 | 70 |

TABLE 23-continued

| Herbicide No. 21 (Kg/Ha) | Biocide No. 1 (Kg/Ha) | Antidote No. | Rate (Kg/Ha) | % Inhibition Corn | Gift | VELE |
|---|---|---|---|---|---|---|
| " | " | 5 | " | 5 | 20 | 50 |
| " | " | 77 | " | 15 | 70 | 70 |
| " | " | 30 | 4.48 | 55 | 80 | 90 |
| " | " | 7 | 8.96 | 30 | 70 | 75 |
| " | " | 12 | 4.48 | 0 | 55 | 60 |
| " | " | 15 | 8.96 | 15 | 70 | 75 |
| " | " | 24 | 4.48 | 45 | 70 | 60 |
| " | " | 31 | " | 50 | 75 | 70 |
| " | " | 32 | " | 40 | 60 | 65 |
| " | " | 33 | " | 10 | 50 | 65 |
| " | " | 2 | " | 40 | 70 | 75 |
| " | " | 6 | " | 30 | 55 | 60 |
| " | " | 8 | " | 25 | 50 | 55 |
| " | " | 10 | " | 20 | 60 | 80 |
| 0.0175 | 8.96 | 16 | 4.48 | 25 | 65 | 70 |
| " | " | 20 | " | 20 | 65 | 60 |
| " | " | 23 | " | 30 | 70 | 75 |
| " | " | 1 | " | 5 | 45 | 55 |
| — | " | — | — | 0 | 20 | 0 |

EXAMPLE 25

The test reported in this example was a duplicate of that in the preceding example, but for substitution of DYFONATE 10G as the biocidal component. The test data for this example is shown in Table 24.

TABLE 24

| Herbicide No. 21 (Kg/Ha) | Biocide No. 9 (Kg/Ha) | Antidote No. | Rate (Kg/Ha) | % Inhibition Corn | Gift | VELE |
|---|---|---|---|---|---|---|
| 0.0175 | — | — | — | 0 | 0 | 45 |
| " | 8.96 | — | — | 30 | 75 | 70 |
| " | " | 29 | 4.48 | 25 | 65 | 50 |
| " | " | 4 | 8.96 | 20 | 65 | 75 |
| " | " | 5 | " | 15 | 70 | 65 |
| " | " | 77 | " | ND[1] | ND[1] | ND[1] |
| " | " | 30 | 4.48 | 25 | 75 | 95 |
| " | " | 7 | 8.96 | 20 | 80 | 70 |
| " | " | 12 | 4.48 | 0 | 70 | 60 |
| " | " | 15 | 8.96 | 25 | 70 | 75 |
| " | " | 24 | 4.48 | 10 | 65 | 65 |
| " | " | 31 | " | 25 | 80 | 75 |
| " | " | 32 | " | 35 | 80 | 70 |
| " | " | 33 | " | 15 | 90 | 75 |
| " | " | 2 | " | 20 | 80 | 80 |
| " | " | 6 | " | 5 | 70 | 75 |
| " | " | 8 | " | 20 | 70 | 60 |
| " | " | 10 | " | 25 | 85 | 85 |
| 0.0175 | 8.96 | 16 | 4.48 | 15 | 75 | 80 |
| " | " | 20 | " | 20 | 75 | 75 |
| " | " | 23 | " | 5 | 65 | 70 |
| " | " | 1 | " | 20 | 60 | 65 |
| — | " | — | — | 0 | 30 | 0 |

[1]"ND" indicates test yielded no meaningful data for one reason or another.

EXAMPLE 26

This example was conducted according to the procedure of the preceding two examples except for a one-day difference in the test initiation and plant observation dates. The biocide used in this test was LORSBAN 15G. Data are shown in Table 25.

TABLE 25

| Herbicide No. 21 (Kg/Ha) | Biocide No. 2 (Kg/Ha) | Antidote No. | Rate (Kg/Ha) | % Inhibition Corn | Gift | VELE |
|---|---|---|---|---|---|---|
| 0.0175 | — | — | — | 0 | 0 | 60 |
| " | 8.96 | — | — | 55 | 90 | 70 |
| " | " | 29 | 4.48 | 60 | 95 | 95 |
| " | " | 4 | 8.96 | 45 | 90 | 75 |
| " | " | 5 | " | 40 | 90 | 70 |
| " | " | 77 | " | 35 | 95 | 80 |
| " | " | 30 | 4.48 | 60 | 95 | 100 |
| " | " | 7 | 8.96 | 45 | 95 | 80 |
| " | " | 12 | 4.48 | 25 | 90 | 70 |
| " | " | 15 | 8.96 | 20 | 95 | 90 |
| " | " | 24 | 4.48 | 55 | 90 | 70 |
| " | " | 31 | " | 60 | 95 | 70 |
| " | " | 32 | " | 60 | 90 | 60 |
| " | " | 33 | " | 15 | 95 | 70 |
| " | " | 2 | " | 45 | 90 | 75 |
| " | " | 6 | " | 40 | 90 | 80 |
| " | " | 8 | " | 45 | 90 | 80 |
| " | " | 10 | " | 50 | 95 | 75 |
| 0.0175 | 8.96 | 16 | 4.48 | 50 | 95 | 70 |
| " | " | 20 | " | 40 | 90 | 80 |
| " | " | 23 | " | 35 | 80 | 75 |
| " | " | 1 | " | 15 | 90 | 60 |
| — | " | — | — | 0 | 70 | 20 |

EXAMPLE 27

This test was conducted simultaneously with that in Example 22, except using THIMET 20G as the biocidal component. Test results are shown in Table 26.

TABLE 26

| Herbicide No. 21 (Kg/Ha) | Biocide No. 10 (Kg/Ha) | Antidote No. | Rate (Kg/Ha) | % Inhibition Corn | Gift | VELE |
|---|---|---|---|---|---|---|
| 0.0175 | — | — | — | 5 | 0 | 50 |
| " | 8.96 | — | — | 55 | 60 | 75 |
| " | " | 29 | 4.48 | 45 | 65 | 75 |
| " | " | 4 | 8.96 | 25 | 55 | 75 |
| " | " | 5 | " | 0 | 40 | 65 |
| " | " | 77 | " | 10 | 60 | 70 |
| " | " | 30 | 4.48 | 45 | 75 | 95 |
| " | " | 7 | 8.96 | 10 | 75 | 75 |
| " | " | 12 | 4.48 | 5 | 55 | 70 |
| " | " | 15 | 8.96 | 15 | 65 | 75 |
| " | " | 24 | 4.48 | 25 | 50 | 80 |
| " | " | 31 | " | 55 | 60 | 70 |
| " | " | 32 | " | 45 | 55 | 75 |
| " | " | 33 | " | 10 | 60 | 75 |
| " | " | 2 | " | 10 | 50 | 65 |
| " | " | 6 | " | 10 | 55 | 70 |
| " | " | 8 | " | 20 | 60 | 75 |
| " | " | 10 | " | 10 | 50 | 45 |
| 0.0175 | 8.96 | 16 | 4.48 | 20 | 60 | 70 |
| " | " | 20 | " | 10 | 60 | 70 |
| " | " | 23 | " | 5 | 55 | 70 |
| " | " | 1 | " | 0 | 55 | 75 |
| — | " | — | — | 0 | 20 | 20 |

In the above series of tests conducted in Examples 24–27; wherein the safening effect of the indicated antidotes was evaluated against negative synergy induced by the interaction of commercial biocides (OP insecticides) with Herb. No. 21 (XRD-48), it was noted that combinations of XRD-498 with OP insecticides increased corn injury from 0–5% up to 30–55%. Safening activity was observed with many of the antidotes, notably Antidote Nos. 1 (MON-13900), 5, 12 (MON-7400) and 33. A reduction in giant foxtail control was noted in Antidote No. 5 (naphthalic anhydride).

The insecticides applied alone caused varying degrees of inhibition of giant foxtail; this response was substantially increased by the addition of XRD-498. Antidote response to negative synergy in these tests was related to the particular biocide used. Ease of antidote response shown was (from highest to lowest); THIMET>COUNTER>DYFONATE>LORSBAN.

EXAMPLE 28

The experiment conducted in this example was designed to compare the relative antidotal efficacy of Antidote No. 12 (MON-7400) and No. 1 (MON-13900) with that of a commercial safener, i.e., CGA-154281 (Antidote No. 28) against negative synergy induced by the interaction of COUNTER 15G (Biocide No. 1) with Herbicide No. 1 (MON-12000) and No. 21 (XRD-498) in corn. The test here was conducted according to Procedure IV, wherein herbicides and biocides and antidotes interact under PPI conditions. Observations made 13 days after planting. Test data are shown in Table 27.

TABLE 27

| Herb. No. | COUNTER® 15G | Antidote | Rate | % Inhibition | | |
|---|---|---|---|---|---|---|
| (0.14 kg/Ha) | (Kg/Ha) | No. | (Kg/Ha) | Corn | Gift | VELE |
| 1 | — | — | — | 10 | 30 | 95 |
| " | 8.96 | — | — | 70 | 90 | 85 |
| " | " | 12 | 4.48 | 0 | 80 | 100 |
| " | " | 1 | " | 5 | 85 | 90 |
| " | " | 28 | " | 5 | 80 | 90 |
| 21 | — | — | — | 5 | 40 | 75 |
| " | 8.96 | — | — | 75 | 95 | 80 |
| " | " | 12 | 4.48 | 20 | 85 | 90 |
| " | " | 1 | " | 10 | 90 | 90 |
| " | " | 28 | " | 35 | 90 | 90 |
| — | 8.96 | — | — | 0 | 0 | 0 |

In the above tests, the antidotes were all equivalent for safening corn injury from Herb. No. 1 and COUNTER 15G combinations. However, Antidotes No. 1 (MON-13900) and 12 (MON-7400) were superior to No. 28 (CGA-154281) for reducing corn injury from the induced negative synergy.

EXAMPLE 29

This example had as its objective the same comparative antidotal efficacy evaluation as in Example 28, except with different herbicides, viz. BEACON, ACCENT and PURSUIT (Herb. Nos. 8, 7 and 18, respectively). Also, these tests were conducted according to the Procedure V described above, wherein the herbicides were applied POE five (5) DAP (PPI) of COUNTER 15G; observations were taken thirteen (13) DAP. Test data are shown in Table 28.

TABLE 28

| Herbicide | COUNTER® 15G | Antidote | Rate | % Inhibition | | |
|---|---|---|---|---|---|---|
| No. | (Kg/Ha) | No. | (Kg/Ha) | Corn | Gift | VELE |
| 8 | — | — | — | 5 | 80 | 85 |
| " | 8.96 | — | — | 60 | 85 | 85 |
| " | " | 12 | 4.48 | 0 | 80 | 90 |
| " | " | 1 | " | 15 | 75 | 85 |
| " | " | 28 | " | 20 | 75 | 85 |
| 7 | — | — | — | 0 | 75 | 70 |
| " | 8.96 | — | — | 55 | 75 | 75 |
| " | " | 12 | 4.48 | 20 | 80 | 80 |
| " | " | 1 | " | 30 | 75 | 80 |
| " | " | 28 | " | 35 | 75 | 75 |
| 18 | — | — | — | 5 | 20 | 65 |

TABLE 28-continued

| Herbicide | COUNTER® 15G | Antidote | Rate | % Inhibition | | |
|---|---|---|---|---|---|---|
| No. | (Kg/Ha) | No. | (Kg/Ha) | Corn | Gift | VELE |
| " | 8.96 | — | — | 55 | 30 | 70 |
| " | " | 12 | 4.48 | 25 | 25 | 75 |
| " | " | 1 | " | 25 | 20 | 70 |
| " | " | 28 | " | 45 | 25 | 70 |
| — | 8.96 | — | — | 0 | 20 | 0 |

In these tests, Antidote No. 28, (CGA-151281), was comparable to MON-13900 (No. 1), but less effective than MON-7400 for safening negative synergy generated by combinations of COUNTER with BEACON and ACCENT. Both MON-7400 and MON-13900 were more active than Antidote No. 28 in relieving corn injury from COUNTER/PURSUIT negative synergy.

In additional tests, a large number of antidotal compounds from a variety of classes of chemistry, e.g., amides, benzhydryls, thiazoles, oximes, quinolines, isoquinolines, etc, etc. were tested for their efficacy against negative synergism induced by the interaction of Herb. No. 21 (XRD-498), and of the commercial herbicides BEACON® (Herb. No. 8) and PURSUIT® (Herb. No. 18) with the commercial insecticide COUNTER® 15G. In these tests, BEACON and PURSUIT were applied postemergence (POE) after the PPI planting of the seeds and covering with COUNTER in accordance with the procedure described in Procedure V above. XRD-498 was applied PPI in accordance with Procedure IV above. In the POE tests, the herbicides were applied thirteen (13) days initiation of the PPI operation of seed and insecticide. Observations of plant response were made nine (9) days later. Timing of observation dates were slightly different in the PPI tests. These tests are described in Examples 30–38 and test results for this series of experiments are shown in Tables 29–37.

EXAMPLE 30

In this example, BEACON was applied POE five (5) days after the PPI application of COUNTER insecticide according to Procedure V. Test plants were corn and the weeds shattercane and velvet leaf. Plant response observations were made nine (9) days later. Results of this test are shown in Table 29.

TABLE 29

| BEACON® | COUNTER® 15G | Antidote | Rate | % Inhibition | | |
|---|---|---|---|---|---|---|
| (Kg/Ha) | (Kg/Ha) | No. | (Kg/Ha) | Corn | Gift | VELE |
| 0.07 | — | — | — | 0 | 75 | 80 |
| " | 8.96 | — | — | 70 | 75 | 85 |
| " | " | 22 | 4.48 | 20 | 65 | 85 |
| " | " | 1 | " | 10 | 70 | 90 |
| " | " | 34 | " | 15 | 70 | 85 |
| " | " | 35 | " | 20 | 75 | 90 |
| " | " | 36 | " | 45 | 75 | 100 |
| " | " | 27 | " | 25 | 75 | 85 |
| " | " | 37 | " | 65 | 80 | 90 |
| " | " | 38 | " | 20 | 80 | 95 |
| " | " | 13 | " | 30 | 70 | 85 |
| " | " | 14 | " | 10 | 80 | 90 |
| " | " | 39 | " | 25 | 75 | 90 |
| " | " | 40 | " | 45 | 85 | 90 |
| " | " | 26 | " | 40 | 70 | 90 |
| " | " | 41 | " | 25 | 80 | 90 |
| " | " | 3 | " | 35 | 70 | 95 |

TABLE 29-continued

| BEACON® (Kg/Ha) | COUNTER® 15G (Kg/Ha) | Antidote No. | Rate (Kg/Ha) | % Inhibition Corn | Gift | VELE |
|---|---|---|---|---|---|---|
| " | " | 17 | " | 15 | 75 | 95 |
| " | " | 18 | " | 55 | 70 | 85 |
| 0.07 | 8.96 | 19 | 4.48 | 20 | 80 | 95 |
| " | " | 21 | " | 20 | 70 | 85 |
| " | " | 25 | " | 45 | 85 | 100 |
| — | 8.96 | — | — | 0 | 25 | 0 |

EXAMPLE 31

This test was conducted simultaneously with that in Example 30 under the same conditions, except using PURSUIT as the herbicidal component. Test results are shown in Table 30.

TABLE 30

| PURSUIT® (Kg/Ha) | COUNTER® 15G (Kg/Ha) | Antidote No. | Rate (Kg/Ha) | % Inhibition Corn | Gift | VELE |
|---|---|---|---|---|---|---|
| 0.01 | — | — | — | 0 | 30 | 70 |
| " | 8.96 | — | — | 55 | 35 | 70 |
| " | " | 22 | 4.48 | 40 | 25 | 75 |
| " | " | 1 | " | 35 | 30 | 75 |
| " | " | 34 | " | 35 | 25 | 70 |
| " | " | 35 | " | 35 | 30 | 65 |
| " | " | 36 | " | 45 | 35 | 80 |
| " | " | 27 | " | 30 | 30 | 75 |
| " | " | 37 | " | 50 | 35 | 75 |
| " | " | 38 | " | 45 | 25 | 70 |
| " | " | 13 | " | 40 | 40 | 70 |
| " | " | 14 | " | 45 | 35 | 75 |
| " | " | 39 | " | 40 | 40 | 80 |
| " | " | 40 | " | 35 | 40 | 70 |
| " | " | 26 | " | 50 | 35 | 75 |
| " | " | 41 | " | 45 | 30 | 70 |
| " | " | 3 | " | 60 | 40 | 70 |
| 0.07 | 8.96 | 17 | " | 30 | 45 | 75 |
| " | " | 18 | " | 50 | 20 | 70 |
| " | " | 19 | " | 35 | 30 | 70 |
| " | " | 21 | " | 40 | 30 | 70 |
| " | " | 25 | " | 50 | 45 | 70 |
| — | 8.96 | — | — | 5 | 10 | 0 |

EXAMPLE 32

Following the procedure described in Procedure IV above, the same antidotes used in the preceding two examples were evaluated for the efficacy against negative synergy induced by the in-soil contact between Herb. No. 21 (XRD-498) and COUNTER 15G (Antidote No. 1). In this example the test plant spectrum included corn, giant foxtail (GIFT) and velvetleaf (VELE). Observations were made thirteen (13) days after PPI. Test results are shown in Table 31.

TABLE 31

| XRD-498 (Kg/Ha) | COUNTER® 15G (Kg/Ha) | Antidote No. | Rate (Kg/Ha) | % Inhibition Corn | Gift | VELE |
|---|---|---|---|---|---|---|
| 0.02 | — | — | — | 5 | 30 | 80 |
| " | 8.96 | — | — | 70 | 75 | 80 |
| " | " | 22 | 4.48 | 45 | 70 | 80 |
| " | " | 1 | " | 25 | 70 | 85 |
| " | " | 34 | " | 35 | 75 | 80 |
| " | " | 35 | " | 40 | 70 | 80 |
| " | " | 36 | " | 60 | 75 | 90 |
| " | " | 27 | " | 30 | 75 | 85 |
| " | " | 37 | " | 60 | 80 | 85 |
| " | " | 38 | " | 50 | 70 | 85 |
| " | " | 13 | " | 65 | 80 | 90 |
| " | " | 14 | " | 45 | 75 | 90 |
| " | " | 39 | " | 50 | 85 | 95 |
| " | " | 40 | " | 60 | 70 | 85 |
| " | " | 26 | " | 65 | 75 | 80 |
| " | " | 41 | " | 60 | 90 | 80 |
| " | " | 3 | " | 55 | 75 | 95 |
| 0.02 | 8.96 | 17 | " | 55 | 75 | 85 |
| " | " | 18 | " | 65 | 75 | 90 |
| " | " | 19 | " | 55 | 75 | 80 |
| " | " | 21 | " | 60 | 65 | 95 |
| " | " | 25 | " | 80 | 100 | 100 |
| — | 8.96 | — | — | 0 | 30 | 0 |

EXAMPLE 33

This example was conducted according to the identical procedure described in Example 30, except that a different series of Antidotal compounds was used in this example to evaluate the negative synergy developed from the interaction of BEACON® herbicide and COUNTER® 15G insecticide. The herbicide was applied POE six (6) days after PPI application of the insecticide. Observations were made eight (8) days later. Test results are shown in Table 32.

TABLE 32

| BEACON® (Kg/Ha) | COUNTER® 15G (Kg/Ha) | Antidote No. | Rate (Kg/Ha) | % Inhibition Corn | SHCA | VELE |
|---|---|---|---|---|---|---|
| 0.07 | — | — | — | 0 | 75 | 90 |
| " | 8.96 | — | — | 70 | 75 | 85 |
| " | " | 12 | 4.48 | 0 | 80 | 85 |
| " | " | 42 | " | 70 | 75 | 90 |
| " | " | 43 | " | 55 | 65 | 85 |
| " | " | 44 | " | 65 | 80 | 85 |
| " | " | 45 | " | 65 | 85 | 80 |
| " | " | 46 | " | 50 | 70 | 90 |
| " | " | 80 | " | 20 | 80 | 85 |
| " | " | 47 | " | 25 | 75 | 85 |
| " | " | 48 | " | 20 | 80 | 90 |

TABLE 32-continued

| BEACON ® (Kg/Ha) | COUNTER ® 15G (Kg/Ha) | Antidote No. | Rate (Kg/Ha) | % Inhibition Corn | SHCA | VELE |
|---|---|---|---|---|---|---|
| " | " | 49 | " | 45 | 70 | 90 |
| " | " | 50 | " | 20 | 75 | 80 |
| " | " | 51 | " | 0 | 80 | 85 |
| " | " | 52 | " | 20 | 70 | 85 |
| " | " | 53 | " | 50 | 80 | 85 |
| " | " | 54 | " | 30 | 70 | 90 |
| " | " | 55 | " | 25 | 75 | 85 |
| " | " | 56 | " | 60 | 75 | 85 |
| " | " | 57 | " | 15 | 80 | 85 |
| " | " | 58 | " | 55 | 70 | 85 |
| " | " | 59 | " | 15 | 80 | 85 |
| — | 8.96 | — | — | 0 | 0 | 0 |

EXAMPLE 34

This example was conducted simultaneously with that in Example 33 under the same conditions, except using the herbicide PURSUIT. Test results are shown in Table 33.

TABLE 33

| PURSUIT ® (Kg/Ha) | COUNTER ® 15G (Kg/Ha) | Antidote No. | Rate (Kg/Ha) | % Inhibition Corn | SHCA | VELE |
|---|---|---|---|---|---|---|
| 0.01 | — | — | — | 5 | 30 | 70 |
| " | 8.96 | — | — | 65 | 30 | 70 |
| " | " | 12 | 4.48 | 40 | 40 | 75 |
| " | " | 42 | " | 60 | 30 | 70 |
| " | " | 43 | " | 65 | 35 | 75 |
| " | " | 44 | " | 60 | 30 | 65 |
| " | " | 45 | " | 65 | 25 | 70 |
| " | " | 46 | " | 55 | 25 | 70 |
| " | " | 80 | " | 55 | 35 | 75 |
| " | " | 47 | " | 50 | 30 | 75 |
| " | " | 48 | " | 45 | 25 | 70 |
| " | " | 49 | " | 70 | 30 | 80 |
| " | " | 50 | " | 45 | 25 | 70 |
| " | " | 51 | " | 30 | 35 | 70 |
| " | " | 52 | " | 45 | 25 | 75 |
| " | " | 53 | " | 50 | 25 | 70 |
| " | " | 54 | " | 55 | 20 | 65 |
| " | " | 55 | " | 50 | 25 | 70 |
| " | " | 56 | " | 60 | 30 | 75 |
| " | " | 19 | " | 55 | 30 | 70 |
| " | " | 57 | " | 65 | 35 | ND |
| " | " | 58 | " | 45 | 30 | 70 |
| — | 8.96 | 59 | — | 0 | 0 | 0 |

EXAMPLE 35

The example was conducted according to the PPI procedure described in Procedure IV above. The herbicidal component in this example was XRD-498 Herbicide No. 21. Observations of plant response made fourteen (14) days after PPI of chemicals. Test results are shown in Table 34.

TABLE 34

| XRD-498 (Kg/Ha) | COUNTER ® 15G (Kg/Ha) | Antidote No. | Rate (Kg/Ha) | % Inhibition Corn | GIFT | VELE |
|---|---|---|---|---|---|---|
| 0.02 | — | — | — | 20 | 35 | 80 |
| " | 8.96 | — | — | 75 | 65 | 90 |
| " | " | 12 | 4.48 | 25 | 60 | 90 |
| " | " | 42 | " | 75 | 70 | 90 |

TABLE 34-continued

| XRD-498 (Kg/Ha) | COUNTER ® 15G (Kg/Ha) | Antidote No. | Rate (Kg/Ha) | % Inhibition | | |
|---|---|---|---|---|---|---|
| | | | | Corn | GIFT | VELE |
| " | " | 43 | " | 80 | 70 | 90 |
| " | " | 44 | " | 75 | 65 | 95 |
| " | " | 45 | " | 70 | 75 | 90 |
| " | " | 46 | " | 65 | 60 | 85 |
| " | " | 80 | " | 40 | 65 | 100 |
| " | " | 47 | " | 60 | 65 | 85 |
| " | " | 48 | " | 30 | 60 | 95 |
| " | " | 49 | " | 55 | 65 | 100 |
| " | " | 50 | " | 60 | 70 | 95 |
| " | " | 51 | " | 25 | 65 | 90 |
| " | " | 52 | " | 40 | 65 | 85 |
| " | " | 53 | " | 60 | 70 | 100 |
| " | " | 54 | " | 55 | 60 | 90 |
| " | " | 55 | " | 45 | 65 | 90 |
| " | " | 56 | " | 65 | 75 | 85 |
| " | " | 19 | " | 35 | 65 | 90 |
| " | " | 57 | " | 65 | 70 | 80 |
| " | " | 58 | " | 30 | 60 | 90 |
| — | 8.96 | 59 | — | 0 | 30 | 20 |

EXAMPLE 36

This example was conducted according to the same procedure described in Examples 30 and 31, using BEACON as the herbicidal component and COUNTER 15G as the biocidal component, except that a different set of antidotal compounds were tested for their efficacy in combating negative synergism. Observations were made seven (7) days after POE application of the herbicide. Test results are shown in Table 35.

TABLE 35

| BEACON ® (Kg/Ha) | COUNTER ® 15G (Kg/Ha) | Antidote No. | Rate (Kg/Ha) | % Inhibition | | |
|---|---|---|---|---|---|---|
| | | | | Corn | SHCA | VELE |
| 0.07 | — | — | — | 0 | 65 | 75 |
| " | 8.96 | — | — | 70 | 75 | 80 |
| " | " | 60 | 8.96 | 40 | 60 | 80 |
| " | " | 61 | " | 35 | 65 | 75 |
| " | " | 62 | " | 30 | 65 | 80 |
| " | " | 63 | " | 30 | 70 | 80 |
| " | " | 64 | " | 20 | 65 | 75 |
| " | " | 65 | " | 25 | 70 | 80 |
| " | " | 7 | " | 20 | 65 | 75 |
| " | " | 66 | " | 30 | 60 | 80 |
| " | " | 67 | " | 35 | 65 | 85 |
| " | " | 68 | " | 25 | 70 | 85 |
| " | " | 69 | " | 30 | 75 | 80 |
| " | " | 70 | " | 70 | 70 | 90 |
| " | " | 9 | " | 15 | 70 | 90 |
| " | " | 11 | " | 25 | 75 | 80 |
| " | " | 71 | " | 20 | 65 | 85 |
| " | " | 72 | 4.48 | 70 | 75 | 85 |
| " | " | 73 | " | 70 | 70 | 75 |
| " | " | 74 | " | 65 | 80 | 80 |
| " | " | 75 | " | 70 | 70 | 85 |
| " | " | 76 | " | 55 | 65 | 80 |
| — | 8.96 | — | — | 0 | 20 | 20 |

EXAMPLE 37

The identical procedure in Example 36 was conducted simultaneously with this test, except for use of the herbicide PURSUIT here. Results are shown in Table 36.

TABLE 36

| PURSUIT ® (Kg/Ha) | COUNTER ® 15G (Kg/Ha) | Antidote No. | Rate (Kg/Ha) | % Inhibition Corn | SHCA | VELE |
|---|---|---|---|---|---|---|
| 0.01 | — | — | — | 5 | 30 | 65 |
| " | 8.96 | — | — | 65 | 40 | 70 |
| " | " | 60 | 8.96 | 60 | 35 | 65 |
| " | " | 61 | " | 55 | 35 | 65 |
| " | " | 62 | " | 55 | 30 | 60 |
| " | " | 63 | " | 55 | 40 | 65 |
| " | " | 64 | " | 60 | 35 | 70 |
| " | " | 65 | " | 50 | 30 | 65 |
| " | " | 7 | " | 50 | 30 | 65 |
| " | " | 66 | " | 50 | 25 | 60 |
| " | " | 67 | " | 45 | 40 | 70 |
| " | " | 68 | " | 65 | 45 | 60 |
| " | " | 69 | " | 50 | 40 | 70 |
| " | " | 70 | " | 65 | 25 | 85 |
| " | " | 9 | " | 30 | 40 | 90 |
| " | " | 11 | " | 15 | 40 | 65 |
| " | " | 71 | " | 45 | 30 | 75 |
| " | " | 72 | 4.48 | 60 | 30 | 70 |
| " | " | 73 | " | 70 | 35 | 70 |
| " | " | 74 | " | 60 | 20 | 70 |
| " | " | 75 | " | 65 | 40 | 75 |
| " | " | 76 | " | 55 | 30 | 70 |
| — | 8.96 | — | — | 0 | 10 | 10 |

EXAMPLE 38

This example describes tests with the same antidotes as used in Examples 36 and 37 using XRD-498 as the herbicide with COUNTER 15G as the biocide. The test procedure here was according to Procedure IV described above. Observations of plant response were taken thirteen (13) days after PPI treatment with chemicals. Test results are shown in Table 37.

TABLE 37

| XRD-498 (Kg/Ha) | COUNTER ® 15G (Kg/Ha) | Antidote No. | Rate (Kg/Ha) | % Inhibition Corn | GIFT | VELE |
|---|---|---|---|---|---|---|
| 0.02 | — | — | — | 15 | 25 | 90 |
| " | 8.96 | — | — | 75 | 70 | 90 |
| " | " | 60 | 8.96 | 60 | 75 | 90 |
| " | " | 61 | " | 60 | 70 | 90 |
| " | " | 62 | " | 65 | 75 | 95 |
| " | " | 63 | " | 65 | 70 | 90 |
| " | " | 64 | " | 60 | 70 | 90 |
| " | " | 65 | " | 45 | 70 | 90 |
| " | " | 7 | " | 55 | 80 | 85 |
| " | " | 66 | " | 50 | 70 | 90 |
| " | " | 67 | " | 55 | 75 | 95 |
| " | " | 68 | " | 45 | 65 | 80 |
| " | " | 69 | " | 35 | 70 | 90 |
| " | " | 70 | " | 75 | 70 | 95 |
| " | " | 9 | " | 20 | 95 | 100 |
| " | " | 11 | " | 25 | 70 | 90 |
| " | " | 71 | " | 30 | 70 | 90 |
| " | " | 72 | 4.48 | 75 | 75 | 90 |
| " | " | 73 | " | 70 | 90 | 90 |
| " | " | 74 | " | 70 | 85 | 90 |
| " | " | 75 | " | 75 | 75 | 85 |
| " | " | 76 | " | 65 | 70 | 90 |
| — | 8.96 | — | — | 0 | 30 | 20 |

The data in Tables 29–37 show that corn injury was increased from 0–5% to 55–70% when COUNTER was used in conjunction with BEACON, PURSUIT or XRD-498. The dichloroacetamide antidotes tested in Examples 3–37 (Tables 29–31) were more effective in BEACON than with PURSUIT and XRD-498. MON-13900 was the most active antidote in these tests followed by Antidote Nos. 27 and 34. In summary, nineteen of twenty of the tested dichloroamide antidotes exhibited significant safening activity, again, led by MON-13900. Significant activity was also shown by seventeen of twenty benzhydryl-class antidotes, of which Antidote No. 51 was most active closely followed by MON-7400. Of ten antidotes of thiazole chemistry all ten were active against negative synergism, with fluazole (No. 7) and Antidote No. 65 being slightly more active than other thiazoles tested. Other active safeners included the oxime Antidote No. 9 (cyometrinil) and the oxazole Antidote No. 11, against PURSUIT/COUNTER interactions.

In further tests to evaluate the applications of this invention, another series of tests were conducted to evaluate the antidotal efficacy of various representative antidotes in combating negative synergy induced by a diverse variety of herbicidal compounds used or expected to be used in loci previously treated with biocides to control various crop pests. In this series of tests, COUNTER 15 G was used because of its prevalent use in agriculture. These tests are described in Examples 39–50 below, using procedures described in Procedures VI and VII described above.

EXAMPLE 39

In this example, tests were conducted according to Procedure VII for the POE application of the herbicides following in-furrow application of COUNTER° 15G insecticide (BIOCIDE No. 1) and the antidote on the pre-planted test seeds. In this test, the herbicides were Nos. 1 (MON-12000), 10 (ALLY®) and #4 (HARMONY®) and the Antidote Nos. 1, 7, 12 and 33.

These in-furrow treatments comprised a 50–50 mix of blended granules of COUNTER with and without 5G granular antidotes at 7.4+7.4 mg/cm or 1.1+0.37 mg active ingredient (a.i.)/cm. The in-furrow initiation of the test was followed five (5) days later with POE application of the herbicides; observations were made eight (8) days later. Test results are shown in Table 38.

TABLE 38

| Herbicide No. | Rate (Kg/Ha) | Biocide No. | | Antidote No. | % Inhibition | | |
|---|---|---|---|---|---|---|---|
| | | | | | Corn | GIFT | VELE |
| 1 | 0.14 | — | | — | 0 | 0 | 85 |
| " | " | 1 | | — | 35 | 0 | 90 |
| " | " | 1 | + | 12 | 0 | 0 | 90 |
| " | " | 1 | + | 7 | 5 | 0 | 90 |
| " | " | 1 | + | 1 | 15 | 0 | 95 |
| " | " | 1 | + | 33 | 0 | 0 | 90 |
| 10 | 0.002 | — | | — | 15 | 0 | 90 |
| " | " | 1 | | — | 55 | 0 | 85 |
| " | " | 1 | + | 12 | 5 | 0 | 90 |
| " | " | 1 | + | 7 | 10 | 20 | 85 |
| " | " | 1 | + | 1 | 15 | 0 | 90 |
| " | " | 1 | + | 33 | 5 | 0 | 90 |
| 4 | 0.17 | — | | — | 0 | 0 | 80 |
| " | " | 1 | | — | 45 | 0 | 85 |
| " | " | 1 | + | 12 | 0 | 0 | 85 |
| " | " | 1 | + | 7 | 0 | 0 | 85 |
| " | " | 1 | + | 1 | 10 | 0 | 90 |
| " | " | 1 | + | 33 | 5 | 0 | 90 |

EXAMPLE 40

In another test, conducted simultaneously with that in Example 39, Herbicide Nos. 5 (chlorimuron ethyl, active ingredient in CLASSIC® herbicide), 7 (nicosulfuron, active ingredient in ACCENT® herbicide) and 15 (tribenuron methyl, active ingredient in EXPRESS® herbicide) were substituted as test herbicides. Test results are shown in Table 39.

TABLE 39

| Herbicide No. | Rate (Kg/Ha) | Biocide No. | | Antidote No. | % Inhibition | | |
|---|---|---|---|---|---|---|---|
| | | | | | Corn | GIFT | VELE |
| 5 | 0.07 | — | | — | 5 | 0 | 85 |
| " | " | 1 | | — | 75 | 0 | 90 |
| " | " | 1 | + | 12 | 0 | 0 | 85 |
| " | " | 1 | + | 7 | 55 | 0 | 90 |
| " | " | 1 | + | 1 | 15 | 0 | 95 |
| " | " | 1 | + | 33 | 30 | 0 | 90 |
| 7 | 0.56 | — | | — | 0 | 85 | 70 |
| " | " | 1 | | — | 60 | 85 | 65 |
| " | " | 1 | + | 12 | 5 | 85 | 75 |
| " | " | 1 | + | 7 | 25 | 85 | 70 |
| " | " | 1 | + | 1 | 10 | 85 | 75 |
| " | " | 1 | + | 33 | 10 | 80 | 65 |
| 15 | 0.0044 | — | | — | 0 | 0 | 75 |
| " | " | 1 | | — | 30 | 0 | 75 |
| " | " | 1 | + | 12 | 0 | 0 | 75 |
| " | " | 1 | + | 7 | 10 | 0 | 75 |
| " | " | 1 | + | 1 | 10 | 20 | 75 |
| " | " | 1 | + | 33 | 15 | 0 | 80 |

The above data in Tables 38 and 39 show that the test antidotes, applied as blended granules in furrow with COUNTER 15G, provided significant corn safening against interactions arising from POE applications of commercial sulfonylurea herbicides. Of the antidotes, MON-7400 provided the highest and most consistent safening effects with all tested herbicides.

EXAMPLE 41

In this example, using the same procedure as above, the following imidazolinone herbicides were used with the same insecticide/biocide and antidotes as above: Herb. No. 16 (imazaquin, a.i. in SCEPTER® herbicide; No. 19 (Code No. AC 222293, a.i. in ASSERT® herbicide); No. 6 (imazethapyr, a.i. in PURSUIT® herbicide and No. 18 (imazapyr, a.i. in ARSENAL® herbicide). Test results are shown in Table 40.

TABLE 40

| Herbicide No. | Rate (Kg/Ha) | Biocide No. | | Antidote No. | % Inhibition | | |
|---|---|---|---|---|---|---|---|
| | | | | | Corn | GIFT | VELE |
| 16 | 0.01 | — | | — | 50 | 20 | 30 |
| " | " | 1 | | — | 70 | 15 | 40 |
| " | " | 1 | + | 12 | 15 | 20 | 25 |
| " | " | 1 | + | 7 | 30 | 10 | 30 |
| " | " | 1 | + | 1 | 20 | 35 | 35 |
| " | " | 1 | + | 33 | 30 | 30 | 40 |
| 19 | 0.28 | — | | — | 5 | 45 | 70 |
| " | " | 1 | | — | 35 | 40 | 60 |
| " | " | 1 | + | 12 | 0 | 35 | 60 |
| " | " | 1 | + | 7 | 10 | 40 | 70 |
| " | " | 1 | + | 1 | 20 | 35 | 65 |
| " | " | 1 | + | 33 | 10 | 35 | 60 |
| 6 | 0.01 | — | | — | 5 | 50 | 60 |
| " | " | 1 | | — | 65 | 55 | 65 |
| " | " | 1 | + | 12 | 0 | 50 | 65 |
| " | " | 1 | + | 7 | 45 | 45 | 70 |
| " | " | 1 | + | 1 | 15 | 60 | 60 |
| " | " | 1 | + | 33 | 20 | 65 | 65 |
| 18 | 0.0044 | — | | — | 15 | 55 | 65 |
| " | " | 1 | | — | 30 | 55 | 60 |
| " | " | 1 | + | 12 | 10 | 60 | 70 |
| " | " | 1 | + | 7 | 20 | 50 | 60 |
| " | " | 1 | + | 1 | 15 | 65 | 65 |
| " | " | 1 | + | 33 | 10 | 65 | 65 |

The above data in Table 40 show that the test antidotes all reduced negative synergy induced by the interaction of the imidazolinone herbicides when contacted with COUNTER 15G insecticide. As in preceding tests, MON-7400 was the most efficacious antidote for these negative synergy interactions.

EXAMPLE 42

This example describes the testing of the above antidotes used in Examples 39–41 to safen negative synergy interactions between representative species of the class of herbicidal compounds identified as azolopyrimidine sulfonamides and COUNTER 15G. The same procedure used in the above examples was conducted in this test. In this test, the herbicides were formulated in 17% acetone and 83% water with 0.25% v/v X-77 surfactant. Test data are shown in Table 41.

TABLE 41

| Herbicide No. | Rate (Kg/Ha) | Biocide No. |   | Antidote No. | % Inhibition Corn | GIFT | VELE |
|---|---|---|---|---|---|---|---|
| 21 | 0.14 | — |   | — | 5 | 30 | 85 |
| " | " | 1 |   | — | 60 | 30 | 85 |
| " | " | 1 | + | 12 | 5 | 25 | 85 |
| " | " | 1 | + | 7 | 30 | 30 | 85 |
| " | " | 1 | + | 1 | 20 | 35 | 85 |
| " | " | 1 | + | 33 | 20 | 30 | 90 |
| 23 | 0.0006 | — |   | — | 10 | 10 | 60 |
| " | " | 1 |   | — | 60 | 20 | 55 |
| " | " | 1 | + | 12 | 5 | 25 | 65 |
| " | " | 1 | + | 7 | 30 | 15 | 60 |
| " | " | 1 | + | 1 | 20 | 20 | 60 |
| " | " | 1 | + | 33 | 15 | 25 | 70 |
| 9 | 0.009 | — |   | — | 0 | 0 | 90 |
| " | " | 1 |   | — | 55 | 20 | 90 |
| " | " | 1 | + | 12 | 0 | 10 | 85 |
| " | " | 1 | + | 7 | 15 | 20 | 85 |
| " | " | 1 | + | 1 | 10 | 30 | 90 |
| " | " | 1 | + | 33 | 5 | 25 | 85 |

In the data in Table 41 it is shown that negative synergy developed between COUNTER 15G and the sulfonamide herbicides significantly enhance corn injury. Also, this injury was significantly reduced by in-furrow treatments with MON-7400, flurazole, MON-13900 and Antidote No. 33. Once again, MON-7400 (No. 12) was the most effective safener and provided 92–100% safening of corn injury.

EXAMPLE 43

In continuing tests to evaluate the variations of this invention, a series of tests were conducted to determine the efficacy of the above safeners in Examples 39–42 to alleviate corn injury induced by the interaction of various additional commercial sulfonylurea herbicides with COUNTER 15G insecticide. In this example, the tests were conducted according to Procedure VI above. In modifications of that procedure, herbicides were applied to soil samples as acetone/water suspensions, incorporated by shaking in a closed container, with subsamples used to cover furrow-treated 10.2 cm pots. Pots were subirrigated followed by overhead misting on days 6–10. Test data (average of two reps) are shown in Table 42.

TABLE 42

| Herbicide No. | Rate (Kg/Ha) | Biocide No. |   | Antidote No. | % Inhibition Corn | GIFT | VELE |
|---|---|---|---|---|---|---|---|
| 12 | 0.0044 | — |   | — | 40 | 0 | 50 |
| " | " | 1 |   | — | 70 | 0 | 50 |

TABLE 42-continued

| Herbicide No. | Rate (Kg/Ha) | Biocide No. |   | Antidote No. | % Inhibition Corn | GIFT | VELE |
|---|---|---|---|---|---|---|---|
| " | " | 1 | + | 12 | 10 | 0 | 60 |
| " | " | 1 | + | 7 | 25 | 0 | 50 |
| " | " | 1 | + | 1 | 20 | 0 | 55 |
| " | " | 1 | + | 33 | 20 | 0 | 60 |
| 14 | 0.07 | — |   | — | 65 | 0 | 85 |
| " | " | 1 |   | — | 90 | 0 | 85 |
| " | " | 1 | + | 12 | 0 | 0 | 85 |
| " | " | 1 | + | 7 | 30 | 0 | 90 |
| " | " | 1 | + | 1 | 10 | 0 | 85 |
| " | " | 1 | + | 33 | 10 | 0 | 85 |
| 13 | 0.0022 | — |   | — | 60 | 25 | 55 |
| " | " | 1 |   | — | 75 | 30 | 65 |
| " | " | 1 | + | 12 | 55 | 25 | 60 |
| " | " | 1 | + | 7 | 70 | 30 | 65 |
| " | " | 1 | + | 1 | 70 | 35 | 60 |
| " | " | 1 | + | 33 | 90 | 35 | 50 |
| 11 | 0.0044 | — |   | — | 10 | 0 | 70 |
| " | " | 1 |   | — | 50 | 0 | 65 |
| " | " | 1 | + | 12 | 10 | 0 | 70 |
| " | " | 1 | + | 7 | 15 | 0 | 65 |
| " | " | 1 | + | 1 | 15 | 0 | 75 |
| " | " | 1 | + | 33 | 20 | 0 | 65 |

In these tests, the antidotes effectively reduced corn injury caused by enhanced herbicidal activity due to interaction of COUNTER 15G and Herbicide No. 12 (chlorsulfuron methyl, active ingredient in GLEAN® herbicide); No. 14 (bensulfuron methyl, a.i. in LONDAX® herbicide) and No. 11 (triasulfuron, a.i. in AMBER® herbicide). Under the conditions of this test, safening of Herbicide No. 13 (sulfometuron methyl, a.i. in OUST® herbicide) was limited to nil.

EXAMPLE 44

This example was designed to test the safening effect of those above safeners used in this test series to relieve corn injury by negative synergism induced by interaction of COUNTER 15G and three imidazolinone herbicides, i.e., imazaquin and imazapyr (used in the POE tests in Example 41) and AC 263222 (a.i. in CADRE® herbicide). As differing from the tests in Example 41, this test was a PPI test according to Procedure VI described above. Observation of test results (Table 43) were taken thirteen 913) days after in-furrow PPI preparation.

TABLE 43

| Herbicide No. | Rate (Kg/Ha) | Biocide No. |   | Antidote No. | % Inhibition Corn | GIFT | VELE |
|---|---|---|---|---|---|---|---|
| 16 | 0.07 | — |   | — | 45 | 40 | 70 |
| " | " | 1 |   | — | 65 | 45 | 65 |
| " | " | 1 | + | 12 | 40 | 35 | 60 |
| " | " | 1 | + | 7 | 55 | 50 | 60 |
| " | " | 1 | + | 1 | 45 | 30 | 60 |
| " | " | 1 | + | 33 | 35 | 45 | 65 |
| 17 | 0.14 | — |   | — | 15 | 80 | 80 |
| " | " | 1 |   | — | 55 | 80 | 75 |
| " | " | 1 | + | 12 | 10 | 80 | 80 |
| " | " | 1 | + | 7 | 35 | 75 | 80 |
| " | " | 1 | + | 1 | 45 | 75 | 80 |
| " | " | 1 | + | 33 | 20 | 80 | 75 |
| 18 | 0.04 | — |   | — | 10 | 60 | 65 |
| " | " | 1 |   | — | 25 | 50 | 60 |
| " | " | 1 | + | 12 | 5 | 50 | 70 |
| " | " | 1 | + | 7 | 10 | 65 | 45 |
| " | " | 1 | + | 1 | 10 | 55 | 50 |

TABLE 43-continued

| Herbicide No. | Rate (Kg/Ha) | Biocide No. | Antidote No. | % Inhibition Corn | GIFT | VELE |
|---|---|---|---|---|---|---|
| " | " | 1 | + 33 | 5 | 45 | 40 |

Each of the test antidotes exhibited varying degrees of safening the corn from the enhanced phytotoxicity due to the interaction of COUNTER 15G with the imidazolinone herbicides. Optimization of test conditions for maximum protection was not undertaken in this or any other tests described herein.

EXAMPLE 45

This example describes PPI tests to evaluate said test safeners in this series with analogs of the sulfonamide herbicides tested under POE herbicide application procedures described in Example 42. In these tests, conducted according to Procedure VI described above, Herbicide Nos. 20, 22 and 24 were applied PPI with the insecticide and antidote. Observations of tests results were made thirteen days after PPI initiation. Data for the average of two replications are shown in Table 44.

TABLE 44

| Herbicide No. | Rate (Kg/Ha) | Biocide No. | Antidote No. | % Inhibition Corn | GIFT | VELE |
|---|---|---|---|---|---|---|
| 20 | 1.12 | — | — | 25 | 15 | 95 |
| " | " | 1 | — | 55 | 20 | 95 |
| " | " | 1 | + 12 | 25 | 25 | 95 |
| " | " | 1 | + 7 | 35 | 10 | 95 |
| " | " | 1 | + 1 | 25 | 20 | 95 |
| " | " | 1 | + 33 | 50 | 30 | 90 |
| 22 | 0.28 | — | — | 0 | 10 | 80 |
| " | " | 1 | — | 60 | 25 | 75 |
| " | " | 1 | + 12 | 0 | 20 | 75 |
| " | " | 1 | + 7 | 15 | 25 | 80 |
| " | " | 1 | + 1 | 5 | 25 | 80 |
| " | " | 1 | + 33 | 5 | 15 | 90 |
| 24 | 0.14 | — | — | 35 | 10 | 90 |
| " | " | 1 | — | 65 | 10 | 95 |
| " | " | 1 | + 12 | 30 | 20 | 90 |
| " | " | 1 | + 7 | 30 | 15 | 95 |
| " | " | 1 | + 1 | 25 | 10 | 90 |
| " | " | 1 | + 33 | 40 | 25 | 95 |

The above data exhibit significant safening of the corn injury caused by interactions between COUNTER 15G insecticide and the sulfonamide herbicides.

EXAMPLE 46

An additional three (3) sulfonamide herbicide analogs were tested simultaneously and under the same conditions described in Example 45. Test data are shown in Table 45.

TABLE 45

| Herbicide No. | Rate (Kg/Ha) | Biocide No. | Antidote No. | % Inhibition Corn | GIFT | VELE |
|---|---|---|---|---|---|---|
| 25 | 0.14 | — | — | 20 | 30 | 70 |
| " | " | 1 | — | 85 | 35 | 70 |
| " | " | 1 | + 12 | 0 | 25 | 70 |
| " | " | 1 | + 7 | 5 | 20 | 75 |
| " | " | 1 | + 1 | 15 | 30 | 75 |

TABLE 45-continued

| Herbicide No. | Rate (Kg/Ha) | Biocide No. | Antidote No. | % Inhibition Corn | GIFT | VELE |
|---|---|---|---|---|---|---|
| " | " | 1 | + 33 | 20 | 25 | 70 |
| 26 | 2.24 | — | — | 0 | 0 | 40 |
| " | " | 1 | — | 20 | 0 | 65 |
| " | " | 1 | + 12 | 5 | 0 | 55 |
| " | " | 1 | + 7 | 5 | 10 | 70 |
| " | " | 1 | + 1 | 20 | 0 | 65 |
| " | " | 1 | + 33 | 10 | 15 | 50 |
| 28 | 0.04 | — | — | 20 | 25 | 80 |
| " | " | 1 | — | 70 | 50 | 85 |
| " | " | 1 | + 12 | 10 | 35 | 80 |
| " | " | 1 | + 7 | 55 | 45 | 90 |
| " | " | 1 | + 1 | 20 | 50 | 90 |
| " | " | 1 | + 33 | 30 | 40 | 80 |

In summary of the test data with sulfonamide herbicides in Examples 45 and 46, it was found that corn injury induced by the COUNTER® 15G/sulfonamides negative synergy was significantly reduced 22 out of 24 times with the test safeners.

EXAMPLE 47

Another test of this invention involved the safening effects of the safeners in this series against negative synergy inducted by the interaction of COUNTER 15G and a sulfonylurea herbicide (OUST®), Herbicide No. 13, and PURSUIT, an imidazolinone herbicide, No. 6. Test conditions were the same as those in Examples 43–46. Test data are shown in Table 46. Other procedures for applying herbicidal formulations are as described in Example 42.

TABLE 46

| Herbicide No. | Rate (Kg/Ha) | Biocide No. | Antidote No. | % Inhibition Corn | GIFT | VELE |
|---|---|---|---|---|---|---|
| 6 | 0.14 | — | — | 5 | 75 | 65 |
| " | " | 1 | — | 60 | 70 | 70 |
| " | " | 1 | + 12 | 10 | 60 | 65 |
| " | " | 1 | + 7 | 40 | 60 | 60 |
| " | " | 1 | + 1 | 15 | 65 | 70 |
| " | " | 1 | + 33 | 20 | 70 | 70 |
| 13 | 0.0011 | — | — | 30 | 0 | 20 |
| " | " | 1 | — | 65 | 10 | 25 |
| " | " | 1 | + 12 | 35 | 0 | 15 |
| " | " | 1 | + 7 | 50 | 0 | 10 |
| " | " | 1 | + 1 | 40 | 25 | 25 |
| " | " | 1 | + 33 | 40 | 10 | 20 |

In these tests, MON-13900, MON-7400 and Antidote No. 33 showed good activity in safening the COUNTER 15G/PURSUIT interaction. Flurazole (No. 7) was less effective than the other safeners. All four antidotes provided some safening, weak to moderate, against the COUNTER 15G/OUST interaction. These particular antidote/insecticide/herbicide combinations appear more difficult to reduce corn injury than the other combinations.

EXAMPLE 48

Additional tests were conducted to compare the safening effect of two benzhydryl (Antidote Nos. 8 and 51) with two dichloroacetamide safeners (Nos. 1 and 16) against negative synergy arising from the interaction COUNTER 15G and BEACON® in corn.

In these tests (according to Procedure VII) the safeners in solution with acetone were applied in furrow to the soil, followed by COUNTER 15G granules at 227 g/305 m (8 oz./1000'). Applications were made in alternate rows in two separate 13.7 cm×27.7 cm pans containing Dupo silt loam. Pans were seeded 1.3 cm deep, placed on benches in a greenhouse and subirrigated. BEACON was formulated in water with 0.25% v/v X-77 surfactant and applied by track sprayer at a rate of 187 L/Ha (20 gal/A). Weed species in this test were giant foxtail, shattercane and velvetleaf. The herbicide was applied five (5) days after PPI initiation and observation of test result (shown in Table 47) made eight (8) days later.

In Table 47 COUNTER 15G is abbreviated as "C" and the antidotes as "A" in the column headings which indicate the "C+A" ratios used in the tests. Control and COUNTER treatments are average of four (4) replications and COUNTER+Antidote treatments, average of 2 reps.

TABLE 47

| Herbicide No. 8 (Kg/Ha) | Anti-dote No. | % Corn Inhibition |||||||
|---|---|---|---|---|---|---|---|---|
| | | | | C:A Ratios ||||
| | | None | C | 5 | 10 | 20 | 40 | 80 | 160 |
| 0.28 | 8 | 0 | 24 | 3 | 5 | 5 | 3 | 5 | 10 |
| " | 51 | 0 | 25 | 0 | 5 | 3 | 8 | 10 | 10 |
| " | 16 | 1 | 26 | 3 | 10 | 10 | 15 | 28 | 23 |
| " | 1 | 0 | 18 | 3 | 3 | 0 | 0 | 3 | 13 |

| Weed Control (separate 10.2 cm pots) | |
|---|---|
| | % Inhibition |
| GIFT | 65 |
| SHCA | 70 |
| VELE | 80 |

The benzhydryl antidotes MON-7400 and Antidote No. 51 were similar to MON-13900 for safening COUNTER 15G/BEACON negative synergy. Significant safening was seen with C:A ratios of 5–160. Antidote No. 16 was not as active as the other safeners in the test.

In another test, wherein ACCENT® (Herbicide No. 7) was substituted for BEACON, using an application rate of 0.56 kg/ha, the results were generally similar with some variation in corn injury between the antidotes.

EXAMPLE 49

Other tests were conducted to test other safeners against corn injury by interactions of in-furrow applied COUNTER 15G followed by POE application of BEACOn or ACCENT herbicides.

The test procedure in this example was according to Procedure VII and followed the description in Example 48. Test data shown in Table 48 represent the average of two replications. Again, in the table "C" stands for COUNTER" and A" for "Antidote".

TABLE 48

| BEACON® (Kg/Ha) | In-Furrow Treatment C ± A | C:A Ratio | % Inhibition Corn |
|---|---|---|---|
| 0.28 | — | — | 0 |
| " | C | — | 55 |
| 0.28 | C + 78 | 20 | 5 |
| " | " | 40 | 5 |
| " | " | 80 | 20 |

TABLE 48-continued

| BEACON® (Kg/Ha) | In-Furrow Treatment C ± A | C:A Ratio | % Inhibition Corn |
|---|---|---|---|
| " | " | 160 | 20 |
| 0.28 | C + 79 | 20 | 0 |
| " | " | 40 | 5 |
| " | " | 80 | 15 |
| " | " | 160 | 20 |
| 0.28 | C + 8 | 20 | 0 |
| " | " | 40 | 0 |
| " | " | 80 | 5 |
| " | " | 160 | 15 |
| 0.28 | C + 16 | 20 | 10 |
| " | " | 40 | 20 |
| " | " | 80 | 20 |
| " | " | 160 | 25 |
| 0.28 | C + 1 | 20 | 5 |
| " | " | 40 | 5 |
| " | " | 80 | 10 |
| " | " | 160 | 15 |
| 0.28 | C + 28 | 20 | 5 |
| " | " | 40 | 5 |
| " | " | 80 | 10 |
| " | " | 160 | 15 |
| — | C | — | 0 |

Weed inhibition in this test was follows: GIFT, 95%, SHCA, 95%, VELE, 99%.

EXAMPLE 50

The above test was simultaneously duplicated procedurally, except using ACCENT® (Herbicide No. 7) as the herbicide; antidotes were the same as well as the insecticide. Test results are shown in Table 49.

TABLE 49

| | In-Furrow Treatment C + A | C:A Ratio | % Inhibition Corn |
|---|---|---|---|
| ACCENT® (Kg/Ha) | | | |
| 0.56 | — | — | 5 |
| " | C | — | 60 |
| 0.56 | C + 78 | 20 | 25 |
| " | " | 40 | 20 |
| " | " | 80 | 40 |
| " | " | 160 | 60 |
| 0.56 | C + 79 | 20 | 15 |
| " | " | 40 | 20 |
| " | " | 80 | 30 |
| " | " | 160 | 45 |
| 0.56 | C + 8 | 20 | 10 |
| " | " | 40 | 15 |
| " | " | 80 | 20 |
| " | " | 160 | 40 |
| BEACON® (Kg/Ha) | | | |
| 0.56 | C + 16 | 20 | 35 |
| " | " | 40 | 40 |
| " | " | 80 | 35 |
| " | " | 160 | 40 |
| 0.56 | C + 1 | 20 | 10 |
| " | " | 40 | 10 |
| " | " | 80 | 10 |
| " | " | 160 | 15 |
| 0.56 | C + 28 | 20 | 15 |
| " | " | 40 | 15 |
| " | " | 80 | 20 |
| " | " | 160 | 15 |
| — | C | — | 0 |

Weed inhibition in this test was follows: GIFT, 95%, SHCA, 95%, VELE, 90%.

In the tests in Examples 49 and 50, MON-7400 (Antidote No. 8) was similar to that of MON-13900 (No. 1) and CGA-154281 (No. 28) for protecting corn from COUNTER/BEACON injury. Acceptable corn injury was observed with COUNTER:Antidote ratios of 20 to 160. Comparable results were seen with COUNTER/ACCENT combinations, except that MON-13900 and CGA-154281 were more effective than MON-7400 at the 160 ratio. Antidote No. 16 was weak in safening effect in these tests.

EXAMPLE 51

Another series of tests were conducted to define the safening effect of various antidotes on a variety of additional biocide/herbicide interactions in corn. These tests are described in Examples 51–55 with test weeds indicated in the tables. In the first test in this series, various antidotes were evaluated for their ability to relieve corn injury from the negative synergy developed by the interaction of BEACON (Herbicide No. 8), ACCENT (Herbicide No. 7) and PURSUIT® (Herbicide No. 18) with the biocide ethoprop Biocide No. 8 (active ingredient in MOCAP®, a nematicide and soil insecticide).

The test procedure in this example was according to Procedure V described above. The herbicides were applied POE five (5) days after PPI initiation of biocide and antidote incorporation; observations were made nine (9) days later. Test results are shown in Table 50.

In this test MOCAP alone at 8.96 kg/ha produced corn stunting, leaf malformations and stand loss; these manifestations of injury were predominant in this test. No interactions or safening effects were observed between BEACON, ACCENT or PURSUIT under conditions of this test. This is not unexpected as the phenomenon of negative synergy can be capricious, depending upon many factors, e.g., climatic, edaphic, etc., as further exemplified by the varied results involving test evaluations of reported corn injury by ERADICANE® (EPTC+dichlormid) or SURPASS® and fonofos in the Canadian Journal of Plant Science, supra. As the authors concluded: results of tests involving negative can be inconsistent from year to year.

EXAMPLE 52

The test in this example paralleled that in Example 51, except the procedure was according to Procedure IV above and the herbicides used were No. 1 (MON-12000); No. 21 (XRD-498) and, again, No. 18 (PURSUIT); the biocide was, again, MOCAP®. Observations were taken thirteen (13) days after PPI treatment with biocide and antidote. Results are shown in Table 51.

TABLE 50

| Herbicide | Rate | Biocide No. 8 | Antidote | Rate | % Inhibition | | |
|---|---|---|---|---|---|---|---|
| No. | (Kg/Ha) | (kg/Ha) | No. | (Kg/Ha) | Corn | SHCA | VELE |
| 8 | 0.28 | — | — | — | 5 | 80 | 90 |
| " | " | 8.96 | — | — | 25 | 90 | 90 |
| " | " | " | 7 | 4.48 | 35 | 100 | 95 |
| " | " | " | 12 | " | 30 | 100 | 90 |
| " | " | " | 16 | " | 25 | 100 | 90 |
| " | " | " | 1 | " | 60 | 100 | 95 |
| " | " | " | 33 | " | 30 | 100 | 85 |
| " | " | " | 28 | " | 35 | 100 | 90 |
| 7 | 0.56 | — | — | — | 10 | 75 | 80 |
| " | " | 8.96 | — | — | 30 | 95 | 85 |
| " | " | " | 7 | 4.48 | 40 | 100 | 85 |
| " | " | " | 12 | " | 35 | 100 | 90 |
| " | " | " | 16 | " | 45 | 100 | 90 |
| " | " | " | 1 | " | 55 | 100 | 85 |
| " | " | " | 33 | " | 30 | 100 | 90 |
| " | " | " | 28 | " | 40 | 95 | 90 |
| 18 | 0.017 | — | — | — | 15 | 40 | 65 |
| " | " | 8.96 | — | — | 25 | 95 | 75 |
| " | " | " | 7 | 4.48 | 45 | 95 | 75 |
| " | " | " | 12 | " | 25 | 100 | 80 |
| " | " | " | 16 | " | 35 | 95 | 75 |
| " | " | " | 1 | " | 55 | 100 | 80 |
| " | " | " | 33 | " | 30 | 95 | 80 |
| " | " | " | 28 | " | 40 | 100 | 80 |
| — | — | 8.96 | — | — | 30 | 85 | 15 |

TABLE 51

| Herbicide | Rate | Biocide No. 8 | Antidote | Rate | % Inhibition | | |
|---|---|---|---|---|---|---|---|
| No. | (Kg/Ha) | (kg/Ha) | No. | (Kg/Ha) | Corn | GIFT | VELE |
| 1 | 0.14 | — | — | — | 0 | 60 | 85 |

TABLE 51-continued

| Herbicide No. | Rate (Kg/Ha) | Biocide No. 8 (kg/Ha) | Antidote No. | Rate (Kg/Ha) | % Inhibition Corn | GIFT | VELE |
|---|---|---|---|---|---|---|---|
| " | " | 8.96 | — | — | 50 | 95 | 85 |
| " | " | " | 7 | 4.48 | 55 | 100 | 90 |
| " | " | " | 12 | " | 40 | 100 | 95 |
| " | " | " | 16 | " | 30 | 95 | 90 |
| " | " | " | 1 | " | 55 | 100 | 95 |
| " | " | " | 33 | " | 40 | 100 | 100 |
| " | " | " | 28 | " | 50 | 100 | 100 |
| 21 | 0.14 | — | — | — | 10 | 70 | 80 |
| " | " | 8.96 | — | — | 55 | 100 | 90 |
| " | " | " | 7 | 4.48 | 60 | 100 | 95 |
| " | " | " | 12 | " | 35 | 100 | 95 |
| " | " | " | 16 | " | 40 | 100 | 90 |
| " | " | " | 1 | " | 60 | 100 | 80 |
| " | " | " | 33 | " | 45 | 100 | 90 |
| " | " | " | 28 | " | 45 | 100 | 95 |
| 18 | 0.14 | — | — | — | 15 | 75 | 65 |
| " | " | 8.96 | — | — | 60 | 100 | 75 |
| " | " | " | 7 | 4.48 | 70 | 100 | 80 |
| " | " | " | 12 | " | 50 | 95 | 65 |
| " | " | " | 16 | " | 60 | 100 | 75 |
| " | " | " | 1 | " | 55 | 100 | 75 |
| " | " | " | 33 | " | 50 | 100 | 80 |
| " | " | " | 28 | " | 50 | 100 | 80 |
| — | — | 8.96 | — | — | 30 | 90 | 20 |

In this PPI test, MOCAP applied alone caused significant corn injury (leaf malformations, stunting and stand reduction), which was enhanced by the addition of each of the herbicides. The antidote activity in this test ranged from moderate to nil, a probable consequence of MOCAP phytotoxicity.

EXAMPLE 53

This test was identical to that in Example 52, except for use of a different biocide, DIAZINON (Biocide No. 5, a nematicide and soil insecticide). Test results are shown in Table 52.

TABLE 52

| Herbicide No. | Rate (Kg/Ha) | Biocide No. 5 (kg/Ha) | Antidote No. | Rate (Kg/Ha) | % Inhibition Corn | SJCA | VELE |
|---|---|---|---|---|---|---|---|
| 1 | 0.14 | — | — | — | 0 | 70 | 85 |
| " | " | 8.96 | — | — | 65 | 95 | 85 |
| " | " | " | 7 | 4.48 | 10 | 95 | 90 |
| " | " | " | 12 | " | 5 | 95 | 95 |
| " | " | " | 16 | " | 0 | 95 | 85 |
| " | " | " | 1 | " | 0 | 95 | 90 |
| " | " | " | 33 | " | 15 | 95 | 90 |
| " | " | " | 28 | " | 5 | 100 | 95 |
| 21 | 0.14 | — | — | — | 5 | 70 | 80 |
| " | " | 8.96 | — | — | 35 | 90 | 80 |
| " | " | " | 7 | 4.48 | 15 | 95 | 85 |
| " | " | " | 12 | " | 0 | 90 | 80 |
| " | " | " | 16 | " | 40 | 95 | 85 |
| " | " | " | 1 | " | 5 | 95 | 85 |
| " | " | " | 33 | " | 15 | 90 | 80 |
| " | " | " | 28 | " | 5 | 90 | 85 |
| 18 | 0.14 | — | — | — | 10 | 75 | 75 |
| " | " | 8.96 | — | — | 50 | 95 | 80 |
| " | " | " | 7 | 4.48 | 45 | 95 | 75 |
| " | " | " | 12 | " | 15 | 95 | 70 |
| " | " | " | 16 | " | 15 | 90 | 70 |
| " | " | " | 1 | " | 10 | 95 | 70 |
| " | " | " | 33 | " | 5 | 95 | 75 |
| " | " | " | 28 | " | 0 | 95 | 60 |
| — | — | 8.96 | — | — | 0 | 50 | 25 |

In this test corn injury was seen with all biocide/herbicide combinations. Effective safening occurred with most combinations, especially those with MON-7400 (No. 12), MON-13900 (No. 1) and CGA 154281 (No. 28).

EXAMPLE 54

This test was also identical to that in the preceding two examples, except that the biocide was malathion (No. 7, an insecticide). Test results shown in Table 53.

TABLE 53

| Herbicide No. | Rate (Kg/Ha) | Biocide No. 7 (kg/Ha) | Antidote No. | Rate (Kg/Ha) | % Inhibition Corn | SJCA | VELE |
|---|---|---|---|---|---|---|---|
| 1 | — | — | — | — | 5 | 75 | 95 |
| " | " | 8.96 | — | — | 70 | 95 | 95 |
| " | " | " | 7 | 4.48 | 15 | 90 | 90 |
| " | " | " | 12 | " | 20 | 95 | 95 |
| " | " | " | 16 | " | 25 | 90 | 90 |
| " | " | " | 1 | " | 0 | 95 | 95 |
| " | " | " | 33 | " | 10 | 90 | 95 |
| " | " | " | 28 | " | 10 | 95 | 90 |
| 21 | 0.14 | — | — | — | 10 | 75 | 85 |
| " | " | 8.96 | — | — | 65 | 85 | 85 |
| " | " | " | 7 | 4.48 | 20 | 90 | 90 |
| " | " | " | 12 | " | 0 | 85 | 90 |
| " | " | " | 16 | " | 10 | 85 | 90 |
| " | " | " | 1 | " | 0 | 75 | 80 |
| " | " | " | 33 | " | 5 | 85 | 85 |
| " | " | " | 28 | " | 10 | 90 | 85 |
| 18 | 0.14 | — | — | — | 15 | 70 | 75 |
| " | " | 8.96 | — | — | 50 | 90 | 75 |
| " | " | " | 7 | 4.48 | 0 | 80 | 65 |
| " | " | " | 12 | " | 0 | 90 | 75 |
| " | " | " | 16 | " | 20 | 80 | 75 |
| " | " | " | 1 | " | 5 | 85 | 70 |
| " | " | " | 33 | " | 25 | 85 | 75 |
| " | " | " | 28 | " | 0 | 80 | 70 |
| — | — | 8.96 | — | — | 0 | 0 | 0 |

In this test malathion interacted with each of the herbicides to enhance corn injury. Flurazole (No. 7), MON-7400, CGA-154281 (No. 28) and Nos. 16 and 33 provided moderate to high degrees of safening against these interactions.

EXAMPLE 55

This test was identical to the preceding ones, except the biocide was DPX-43898 (No. 6, active ingredient in FORTRESS® insecticide, a soil insecticide). Also, the observation time was fourteen (14) days after PPI initiation. Test results are shown in Table 54.

TABLE 54

| Herbicide No. | Rate (Kg/Ha) | Biocide No. 6 (kg/Ha) | Antidote No. | Rate (Kg/Ha) | % Inhibition Corn | SJCA | VELE |
|---|---|---|---|---|---|---|---|
| 1 | — | — | — | — | 5 | 65 | 90 |
| " | " | 8.96 | — | — | 55 | 75 | 95 |
| " | " | " | 7 | 4.48 | 10 | 90 | 95 |
| " | " | " | 12 | " | 15 | 80 | 90 |
| " | " | " | 16 | " | 25 | 75 | 90 |
| " | " | " | 1 | " | 10 | 80 | 95 |
| " | " | " | 33 | " | 15 | 80 | 90 |
| " | " | " | 28 | " | 15 | 75 | 90 |
| 21 | 0.14 | — | — | — | 10 | 60 | 85 |
| " | " | 8.96 | — | — | 60 | 80 | 80 |
| " | " | " | 7 | 4.48 | 25 | 85 | 85 |
| " | " | " | 12 | " | 0 | 75 | 80 |
| " | " | " | 16 | " | 25 | 85 | 85 |
| " | " | " | 1 | " | 5 | 85 | 85 |
| " | " | " | 33 | " | 10 | 85 | 90 |
| " | " | " | 28 | " | 15 | 80 | 85 |
| 18 | 0.14 | — | — | — | 15 | 75 | 70 |
| " | " | 8.96 | — | — | 45 | 85 | 75 |
| " | " | " | 7 | 4.48 | 30 | 90 | 75 |
| " | " | " | 12 | " | 0 | 90 | 70 |
| " | " | " | 16 | " | 25 | 90 | 70 |
| " | " | " | 1 | " | 20 | 85 | 75 |
| " | " | " | 33 | " | 15 | 90 | 70 |
| " | " | " | 28 | " | 20 | 85 | 65 |
| — | — | 8.96 | — | — | 0 | 0 | 0 |

Once again, the test safeners all provided moderate to high degrees of safening activity against interactions from combinations of FORTRESS with MON-12000 and XRD-498. With the exception of MON-7400, these antidotes were less effective against the FORTRESS/PURSUIT interaction.

In another series of tests of the multiple variations of this invention, various herbicidal and co-herbicidal combinations were tested to evaluate the antidotal effectiveness of selected antidotes against corn injury by negative synergism induced by the interaction of said herbicidal/co-herbicidal mixtures and a biocide, exemplified by COUNTER® 15G. Test procedures in this series followed either Procedure VI or VII described above with noted variations. In the tables below COUNTER® 15G is symbolized by the letter "C" and the antidotes by the letter "A".

EXAMPLE 56

In the first test in this series of tests with co-herbicides, was conducted according to general Procedure VII described above, wherein the in-furrow treatments involving biocide/safener incorporation comprised granules of COUNTER 15G alone or blended in a 50:50 mix with safener 15G at 7.4+7.4 mg/cm or 1.1+0.37 mg active ingredient/cm.

The herbicide was BEACON® (No. 8) in combination with co-herbicides H (2,4-D); F (BANVEL®); G (BLADEX®); I (MON-12000) or J (XRD-498). BEACON and XRD-498 were formulated in 50% water/50% acetone containing 0.25 v/v % of X-77 surfactant. The POE combinations were applied as tank mixtures, five (5) days after the PPI operation and plant response observations taken eight (8) days later. Test results are shown in Table 55.

TABLE 55

| Herbicide No. | + | Co-Herbicide | Rate (Kg/Ha) | C ± A | % Inhibition Corn | SHCA | VELE |
|---|---|---|---|---|---|---|---|
| 8 | + | H | 0.14 + 0.28 | — | 10 | 60 | 80 |
| " | " | " | " | C | 25 | 65 | 80 |
| " | " | " | " | C + 12 | 10 | 70 | 85 |
| " | " | " | " | C + 7 | 5 | 60 | 80 |
| " | " | " | " | C + 1 | 20 | 65 | 80 |
| " | " | " | " | C + 16 | 5 | 55 | 80 |
| 8 | + | F | 0.14 + 0.28 | — | 0 | 70 | 85 |
| " | " | " | " | C | 30 | 75 | 85 |
| " | " | " | " | C + 12 | 0 | 70 | 80 |
| " | " | " | " | C + 7 | 5 | 70 | 85 |
| " | " | " | " | C + 1 | 5 | 75 | 90 |
| " | " | " | " | C + 16 | 15 | 80 | 85 |
| 8 | + | G | 0.14 + 1.12 | — | 10 | 75 | 95 |
| " | " | " | " | C | 35 | 75 | 100 |
| " | " | " | " | C + 12 | 10 | 75 | 100 |
| " | " | " | " | C + 7 | 15 | 80 | 95 |
| " | " | " | " | C + 1 | 15 | 70 | 100 |
| " | " | " | " | C + 16 | 20 | 80 | 100 |
| 8 | + | I | 0.14 + 0.07 | — | 0 | 75 | 90 |
| " | " | " | " | C | 20 | 70 | 90 |
| " | " | " | " | C + 12 | 10 | 70 | 90 |
| " | " | " | " | C + 7 | 0 | 70 | 90 |
| " | " | " | " | C + 1 | 10 | 75 | 90 |
| " | " | " | " | C + 16 | 5 | 70 | 95 |
| 8 | + | J | 0.28 + 0.07 | — | 0 | 70 | 85 |
| " | " | " | " | C | 70 | 80 | 85 |
| " | " | " | " | C + 12 | 10 | 75 | 90 |
| " | " | " | " | C + 7 | 40 | 75 | 90 |
| " | " | " | " | C + 1 | 20 | 80 | 90 |
| " | " | " | " | C + 16 | 15 | 75 | 85 |

In this test, MON-7400, flurazole, MON-13900 or MON-4660 (Antidote No. 16, also has the code No. AD-67) applied in furrow, reduced corn injury from the interaction of COUNTER 15G with each of herbicide/co-herbicide combinations.

EXAMPLE 57

The test in this example was conducted in the manner described in Example 56, except substituting ACCENT® for BEACON as the primary herbicide (in the context of this invention) and observing results seven (7) days after POE herbicide application. Results are shown in Table 56.

TABLE 56

| Herbicide No. | Co-Herbicide | Rate (Kg/Ha) | C ± A | % Inhibition Corn | SHCA | VELE |
|---|---|---|---|---|---|---|
| 7 | + H | 0.28 + 0.28 | — | 15 | 70 | 80 |
| " | " " | " | C | 25 | 60 | 85 |
| " | " " | " | C + 12 | 10 | 70 | 80 |
| " | " " | " | C + 7 | 10 | 75 | 85 |
| " | " " | " | C + 1 | 10 | 70 | 80 |
| " | " " | " | C + 16 | 15 | 75 | 80 |
| 7 | + F | 0.28 + 0.28 | — | 5 | 75 | 85 |
| " | " " | " | C | 30 | 60 | 80 |
| " | " " | " | C + 12 | 5 | 80 | 85 |
| " | " " | " | C + 7 | 20 | 70 | 80 |
| " | " " | " | C + 1 | 5 | 65 | 85 |
| " | " " | " | C + 16 | 10 | 70 | 85 |
| 7 | + G | 0.28 + 1.12 | — | 10 | 70 | 95 |
| " | " " | " | C | 20 | 55 | 100 |
| " | " " | " | C + 12 | 5 | 65 | 100 |
| " | " " | " | C + 7 | 15 | 65 | 100 |
| " | " " | " | C + 1 | 15 | 70 | 100 |
| " | " " | " | C + 16 | 15 | 75 | 95 |
| 7 | + I | 0.28 + 0.07 | — | 0 | 75 | 90 |
| " | " " | " | C | 30 | 70 | 90 |
| " | " " | " | C + 12 | 0 | 75 | 90 |
| " | " " | " | C + 7 | 5 | 70 | 90 |
| " | " " | " | C + 1 | 10 | 70 | 90 |
| " | " " | " | C + 16 | 10 | 75 | 90 |
| 7 | + J | 0.28 + 0.07 | — | 0 | 75 | 85 |
| " | " " | " | C | 75 | 75 | 90 |
| " | " " | " | C + 12 | 0 | 60 | 85 |
| " | " " | " | C + 7 | 40 | 70 | 90 |
| " | " " | " | C + 1 | 20 | 75 | 90 |
| " | " " | " | C + 16 | 40 | 75 | 85 |

In this example corn injury was reduced by in-furrow treatments of all herbicide/co-herbicide combinations applied POE and in contact with COUNTER 15G with all test antidotes.

EXAMPLE 58

This example describes a process substantially identical to that in Examples 56 and 57, except using PURSUIT® (Herbicide No. 18) as the herbicide. The co-herbicides, biocide and safeners are shown in Table 57, together with test results.

TABLE 57

| Herbicide No. | Co-Herbicide | Rate (Kg/Ha) | C ± A | % Inhibition Corn | SHCA | VELE |
|---|---|---|---|---|---|---|
| 18 | + H | 0.01 + 0.28 | — | 15 | 20 | 80 |
| " | " " | " | C | 40 | 30 | 80 |
| " | " " | " | C + 12 | 5 | 20 | 80 |
| " | " " | " | C + 7 | 20 | 25 | 85 |
| " | " " | " | C + 1 | 20 | 15 | 85 |
| " | " " | " | C + 16 | 15 | 25 | 80 |
| 18 | + F | 0.01 + 0.28 | — | 5 | 20 | 85 |
| " | " " | " | C | 35 | 20 | 80 |
| " | " " | " | C + 12 | 5 | 35 | 85 |
| " | " " | " | C + 7 | 15 | 20 | 85 |
| " | " " | " | C + 1 | 10 | 15 | 80 |
| " | " " | " | C + 16 | 20 | 20 | 85 |
| 18 | + G | 0.01 + 1.12 | — | 5 | 20 | 9 |
| " | " " | " | C | 40 | 25 | 95 |
| " | " " | " | C + 12 | 5 | 15 | 90 |
| " | " " | " | C + 7 | 20 | 25 | 100 |
| " | " " | " | C + 1 | 15 | 30 | 100 |
| " | " " | " | C + 16 | 20 | 20 | 95 |
| 18 | + I | 0.01 + 0.07 | — | 15 | 25 | 0– |
| " | " " | " | C | 75 | 2– | 0– |
| " | " " | " | C + 12 | 15 | 25 | 0– |
| " | " " | " | C + 7 | 30 | 30 | 90 |
| " | " " | " | C + 1 | 25 | 3– | 05 |
| " | " " | " | C + 16 | 35 | 35 | 05 |
| 18 | + J | 0.01 + 0.07 | — | 15 | 20 | 85 |

TABLE 57-continued

| Herbicide No. | Co- + Herbicide | Rate (Kg/Ha) | C ± A | % Inhibition Corn | SHCA | VELE |
|---|---|---|---|---|---|---|
| " | " | " | C | 70 | 25 | 90 |
| " | " | " | C + 12 | 25 | 30 | 90 |
| " | " | " | C + 7 | 60 | 25 | 90 |
| " | " | " | C + 1 | 45 | 35 | 85 |
| " | " | " | C + 16 | 55 | 25 | 90 |

Once again, it was found that each of the test antidotes effected corn injury reduction due to negative synergy induced by contacting POE applied herbicide/co-herbicide tank mixtures with previously in-furrow treated COUNTER+safener. MON-7400 was the most efficacious safener in this test.

EXAMPLE 59

The procedure used in this example involved the PPI application of biocide and safener as described in general Procedure VI above. The "primary" herbicide in this test was acetone and applied as tank mixtures, incorporated into Dupo silt loam soil with a rotary drum mixer. Subsamples were used to cover seeded and in-furrow treated 10.2 cm pots. Pots were placed on greenhouse benches and subirrigated. Plant responses were observed thirteen days after PPI initiation. Test results (average of two replications) are shown in Table 58, wherein giant foxtail (GIFT) was used in place of shattercane.

TABLE 58

| Herbicide No. | Co- + Herbicide | Rate (Kg/Ha) | C ± A | % Inhibition Corn | GIFT | VELE |
|---|---|---|---|---|---|---|
| 1 | + B | 0.14 + 0.56 | — | 40 | 100 | 100 |
| " | " " | " | C | 85 | 99 | 100 |
| " | " " | " | C + 12 | 0 | 95 | 100 |
| " | " " | " | C + 7 | 15 | 95 | 100 |
| " | " " | " | C + 1 | 10 | 95 | 95 |
| " | " " | " | C + 16 | 5 | 99 | 100 |
| 1 | + C | 0.14 + 0.4 | — | 20 | 99 | 95 |
| " | " " | " | C | 70 | 95 | 95 |
| " | " " | " | C + 12 | 0 | 95 | 95 |
| " | " " | " | C + 7 | 0 | 95 | 100 |
| " | " " | " | C + 1 | 10 | 99 | 100 |
| " | " " | " | C + 16 | 15 | 99 | 100 |
| 1 | + A | 0.14 + 0.28 | — | 35 | 99 | 100 |
| " | " " | " | C | 05 | 00 | 100 |
| " | " " | " | C + 12 | 20 | 95 | 100 |
| " | " " | " | C + 7 | 10 | 95 | 100 |
| " | " " | " | C + 1 | 15 | 100 | 100 |
| " | " " | " | C + 16 | 15 | 99 | 100 |
| 1 | + D | 0.14 + 2.24 | — | 0 | 95 | 100 |
| " | " " | " | C | 60 | 85 | 100 |
| " | " " | " | C + 12 | 0 | 90 | 100 |
| " | " " | " | C + 7 | 5 | 90 | 100 |
| " | " " | " | C + 1 | 15 | 85 | 100 |
| " | " " | " | C + 16 | 5 | 90 | 100 |
| 1 | + E | 0.14 + 2.24 | — | 10 | 95 | 95 |
| " | " " | " | C | 60 | 95 | 95 |
| " | " " | " | C + 12 | 0 | 90 | 95 |
| " | " " | " | C + 7 | 10 | 95 | 95 |
| " | " " | " | C + 1 | 15 | 90 | 100 |
| " | " " | " | C + 16 | 10 | 90 | 100 |
| 1 | + K | 0.14 + 0.07 | — | 30 | 20 | 95 |
| " | " " | " | C | 75 | 30 | 90 |
| " | " " | " | C + 12 | 15 | 25 | 95 |
| " | " " | " | C + 7 | 15 | 20 | 90 |
| " | " " | " | C + 1 | 10 | 20 | 95 |
| " | " " | " | C + 16 | 5 | 15 | 90 |

MON-12000 (Herbi-cide No. 1) in admixture with other herbicides designated as "co-herbicides", which included LASSO® (co-herbicide B); DUAL® (C); acetochlor (A); EPTAM® (D); butylate (E) and PURSUIT® (K).

The in-furrow treatments with blended COUNTER 15G and antidote mixtures was as described in above examples. MON-12000 and the co-herbicides were formulated in The above test data show that the tested safeners each provided high levels of corn safening against the negative synergy developed by contact of the herbicide/co-herbicide mixtures with COUNTER 15G.

EXAMPLE 60

This test was conducted in the same manner used in Example 59. All biocide and antidote components were the same and in these tests XRD-498 (Herbicide No. was the prime herbicide. Co-herbicides are shown in Table 59 together with test data.

EXAMPLE 61

In one other test conducted as described in the preceding examples in this series of tests, the herbicide PURSUIT® was used as the primary herbicide (in the context of this invention) together with the same insecticide and safeners as above and the co-herbicides shown in Table 60, together with test results.

TABLE 59

| Herbicide No. | + | Co-Herbicide | Rate (Kg/Ha) | C ± A | % Inhibition Corn | SHCA | VELE |
|---|---|---|---|---|---|---|---|
| 21 | + | B | 0.14 + 0.56 | — | 40 | 100 | 95 |
| " | " | " | " | C | 80 | 99 | 95 |
| " | " | " | " | C + 12 | 0 | 99 | 95 |
| " | " | " | " | C + 7 | 25 | 99 | 95 |
| " | " | " | " | C + 1 | 5 | 99 | 95 |
| " | " | " | " | C + 16 | 15 | 95 | 100 |
| 21 | + | C | 0.14 + 0.4 | — | 15 | 99 | 95 |
| " | " | " | " | C | 70 | 100 | 90 |
| " | " | " | " | C + 12 | 5 | 99 | 90 |
| " | " | " | " | C + 7 | 30 | 99 | 90 |
| " | " | " | " | C + 1 | 15 | 99 | 95 |
| " | " | " | " | C + 16 | 25 | 95 | 95 |
| 21 | + | A | 0.14 + 0.28 | — | 45 | 100 | 95 |
| " | " | " | " | C | 90 | 100 | 95 |
| " | " | " | " | C + 12 | 15 | 100 | 95 |
| " | " | " | " | C + 7 | 55 | 99 | 95 |
| " | " | " | " | C + 1 | 25 | 100 | 95 |
| " | " | " | " | C + 16 | 35 | 99 | 95 |
| 21 | + | D | 0.14 + 2.24 | — | 5 | 90 | 100 |
| " | " | " | " | C | 65 | 95 | 95 |
| " | " | " | " | C + 12 | 0 | 95 | 100 |
| " | " | " | " | C + 7 | 30 | 90 | 100 |
| " | " | " | " | C + 1 | 15 | 95 | 95 |
| " | " | " | " | C + 16 | 10 | 90 | 100 |
| 21 | + | E | 0.14 + 2.24 | — | 0 | 95 | 95 |
| " | " | " | " | C | 55 | 99 | 90 |
| " | " | " | " | C + 12 | 10 | 99 | 95 |
| " | " | " | " | C + 7 | 30 | 99 | 90 |
| " | " | " | " | C + 1 | 20 | 95 | 90 |
| " | " | " | " | C + 16 | 25 | 99 | 90 |
| 21 | + | K | 0.14 + 0.07 | — | 10 | 60 | 90 |
| " | " | " | " | C | 65 | 55 | 85 |
| " | " | " | " | C + 12 | 10 | 60 | 80 |
| " | " | " | " | C + 7 | 30 | 50 | 85 |
| " | " | " | " | C + 1 | 25 | 60 | 85 |
| " | " | " | " | C + 16 | 35 | 65 | 90 |

The corn injury resulting from negative synergy arising from interaction between in-furrow-applied COUNTER 15G and the XRD-498/co-herbicide mixture was significantly reduced by each of the safeners in the test. MON-7400 was the most effective safener in this test followed by MON-13900, MON-4660 and flurazole.

TABLE 60

| Herbicide No. | + | Co-Herbicide | Rate (Kg/Ha) | C + A | % Inhibition Corn | SHCA | VELE |
|---|---|---|---|---|---|---|---|
| 18 | + | B | 0.14 + 0.56 | — | 40 | 100 | 80 |
| " | " | " | " | C | 75 | 100 | 85 |
| " | " | " | " | C + 12 | 15 | 99 | 85 |
| " | " | " | " | C + 7 | 55 | 99 | 80 |
| " | " | " | " | C + 1 | 5 | 100 | 85 |
| " | " | " | " | C + 16 | 20 | 95 | 90 |
| 18 | + | C | 0.14 + 0.4 | — | 20 | 99 | 75 |
| " | " | " | " | C | 65 | 99 | 80 |
| " | " | " | " | C + 12 | 5 | 99 | 80 |
| " | " | " | " | C + 7 | 25 | 99 | 85 |
| " | " | " | " | C + 1 | 15 | 99 | 80 |
| " | " | " | " | C + 16 | 20 | 99 | 80 |
| 18 | + | A | 0.14 + 0.28 | — | 50 | 100 | 90 |
| " | " | " | " | C | 85 | 100 | 80 |

TABLE 60-continued

| Herbicide No. | Co-+ Herbicide | Rate (Kg/Ha) | C + A | % Inhibition | | |
|---|---|---|---|---|---|---|
| | | | | Corn | SHCA | VELE |
| " | " | " | C + 12 | 15 | 99 | 85 |
| " | " | " | C + 7 | 65 | 99 | 85 |
| " | " | " | C + 1 | 25 | 99 | 80 |
| " | " | " | C + 16 | 20 | 100 | 80 |
| 18 | + D | 0.14 + 2.24 | — | 30 | 95 | 90 |
| " | " | " | C | 70 | 99 | 95 |
| " | " | " | C + 12 | 5 | 95 | 95 |
| " | " | " | C + 7 | 45 | 95 | 100 |
| " | " | " | C + 1 | 15 | 95 | 100 |
| " | " | " | C + 16 | 35 | 95 | 90 |
| 18 | + E | 0.14 + 2.24 | — | 35 | 99 | 95 |
| " | " | " | C | 70 | 95 | 90 |
| " | " | " | C + 12 | 10 | 95 | 85 |
| " | " | " | C + 7 | 35 | 99 | 85 |
| " | " | " | C + 1 | 20 | 95 | 90 |
| " | " | " | C + 16 | 35 | 95 | 95 |

In this test, corn injury arising from the expected herbicide/biocide interaction was reduced by in-furrow applications of MON-7400, flurazole, MON-13900 or MON-4660. Of the safeners here, MON-7400 and MON-13900 were more effective than flurazole or MON-4660 in safening the negative synergy developed.

The above series of tests with various herbicide/co-herbicide combinations, safeners and a commercial biocide indicate the broad scope of this invention. In particular, it is to be noted that all of the above herbicides, except XRD-498, whether designated for purposes of illustration herein as the "prime" or "principal" herbicide or as a "co-herbicide" are commercial products. Thus, the importance of the invention is emphasized.

Moreover, the successful safening with a wide variety of antidotal compounds of negative synergy from a wide variety of herbicides, co-herbicides and biocides suggests the broad scope of the invention. Other products which may suitably be useful according to this invention are combinations of the herbicidal compound dicamba and its alkali metal salts or alkylamine or ammonium salts with any of the herbicides exemplified above as herbicides and/or co-herbicides, whether primarily suitable as graminaceous or broad leaf herbicides, e.g., alachlor, acetochlor, metolachlor, or other α-haloacetamides and α-haloacetanilides or other chemistries mentioned herein, further containing or contacted with any suitable antidote and biocide particularly those designated herein as preferred, e.g., COUNTER® insecticide, MON-7400, MON-13900, CGA-151284, etc., antidotes.

Tests according to this invention in various crops indicate widespread application of the invention. In Examples 62–66 below are described tests with a variety of herbicides contacted with COUNTER® 15G in the presence and absence of MON-7400 (Antidote No. 12); MON-13900 (No. 1); MON-4660 (No. 16) and flurazole (No. 16). Those tests were conducted according to Procedures IV or V described above and illustrated further in other foregoing examples. Plants used in all tests were, for crops (as abbreviated in parentheses); cotton (COTT); soybean (SOBE); CORN, grain sorghum (GRSO); wheat (WHEA) and RICE, and the weeds giant foxtail (GIFT) and velvetleaf (VELE). The data in the tables below represent averages of two replications.

EXAMPLE 62

In this test the crops and weeds were planted 1.3 cm deep in 13.7 cm×27.7 cm pans containing Dupo silt loam soil. The test safeners were applied in acetone solution and COUNTER 15G as dry granules to soil cover layers and incorporated by shaking in a bag. Treated cover layers were placed on seeded pans which were transferred to greenhouse benches and subirrigated. Herbicide was applied POE six (6) days after PPI initiation and observations of plant injury made ten (10) days later; results are shown in Table 61. The herbicide used in this example was BEACON (No. 8).

TABLE 61

| Herb. No. 8 Kg/Ha) | Biocide No. 1 (Kg/Ha) | Antidote No. | Rate (Kg/Ha) | % Inhibition | | | | | | | |
|---|---|---|---|---|---|---|---|---|---|---|---|
| | | | | COTT | SOBE | CORN | GRSO | WHEA | RICE | GIFT | VELE |
| 0.14 | — | — | — | 70 | 55 | 0 | 80 | 70 | 80 | 80 | 95 |
| " | 8.96 | — | — | 65 | 50 | 35 | 80 | 70 | 80 | 85 | 95 |
| " | " | 12 | 4.48 | 65 | 60 | 0 | 85 | 65 | 70 | 80 | 90 |
| " | " | 7 | " | 70 | 55 | 5 | 85 | 70 | 80 | 90 | 95 |
| " | " | 1 | " | 65 | 40 | 5 | 80 | 65 | 75 | 80 | 95 |
| " | " | 16 | " | 70 | 60 | 0 | 80 | 65 | 80 | 85 | 95 |
| 0.17 | — | — | — | 65 | 45 | 0 | 75 | 60 | 70 | 65 | 95 |
| " | 8.96 | — | — | 70 | 45 | 10 | 70 | 75 | 70 | 80 | 95 |
| " | " | 12 | 4.48 | 65 | 40 | 5 | 70 | 70 | 65 | 75 | 95 |
| " | " | 7 | " | 60 | 40 | 0 | 75 | 70 | 65 | 70 | 95 |
| " | " | 1 | " | 60 | 40 | 0 | 75 | 60 | 60 | 75 | 95 |
| " | " | 16 | " | 65 | 45 | 5 | 70 | 60 | 60 | 85 | 90 |
| 0.0022 | — | — | — | 30 | 25 | 0 | 65 | 40 | 30 | 50 | 85 |
| " | 8.96 | — | — | 40 | 25 | 0 | 60 | 55 | 35 | 75 | 90 |
| " | " | 12 | 4.48 | 30 | 20 | 0 | 65 | 50 | 30 | 70 | 80 |

TABLE 61-continued

| Herb. No. 8 | Biocide No. 1 | Antidote | Rate | % Inhibition | | | | | | | |
|---|---|---|---|---|---|---|---|---|---|---|---|
| Kg/Ha) | (Kg/Ha) | No. | (Kg/Ha) | COTT | SOBE | CORN | GRSO | WHEA | RICE | GIFT | VELE |
| " | " | 7 | " | 45 | 25 | 5 | 55 | 55 | 20 | 80 | 80 |
| " | " | 1 | " | 30 | 20 | 0 | 55 | 50 | 30 | 70 | 85 |
| " | " | 16 | " | 50 | 30 | 0 | 65 | 30 | 25 | 75 | 90 |
| — | " | — | — | 15 | 0 | 0 | 10 | 0 | 10 | 20 | 10 |

EXAMPLE 63

The test procedure described in Example 62 was repeated using ACCENT® (Herbicide No. 7) as the herbicide; the biocide and safeners were the same. Test results are shown in Table 62.

TABLE 62

| Herb. No. 7 | Biocide No. 1 | Antidote | Rate | % Inhibition | | | | | | | |
|---|---|---|---|---|---|---|---|---|---|---|---|
| Kg/Ha) | (Kg/Ha) | No. | (Kg/Ha) | COTT | SOBE | CORN | GRSO | WHEA | RICE | GIFT | VELE |
| 0.28 | — | — | — | 50 | 40 | 0 | 75 | 60 | 50 | 75 | 65 |
| " | 8.96 | — | — | 55 | 35 | 25 | 70 | 60 | 45 | 80 | 70 |
| " | " | 12 | 4.48 | 45 | 40 | 0 | 70 | 65 | 55 | 75 | 70 |
| " | " | 7 | " | 55 | 35 | 0 | 75 | 65 | 45 | 85 | 70 |
| " | " | 1 | " | 50 | 45 | 0 | 65 | 50 | 60 | 75 | 65 |
| " | " | 16 | " | 50 | 35 | 0 | 80 | 70 | 65 | 90 | 75 |
| 0.035 | — | — | — | 40 | 20 | 0 | 65 | 45 | 40 | 70 | 60 |
| " | 8.96 | — | — | 45 | 25 | 15 | 60 | 45 | 50 | 80 | 65 |
| " | " | 12 | 4.48 | 40 | 20 | 0 | 70 | 50 | 40 | 75 | 65 |
| " | " | 7 | " | 40 | 20 | 5 | 70 | 55 | 40 | 85 | 65 |
| " | " | 1 | " | 50 | 25 | 0 | 75 | 40 | 45 | 70 | 60 |
| " | " | 16 | " | 60 | 20 | 0 | 70 | 60 | 45 | 85 | 80 |
| 0.0044 | — | — | — | 25 | 10 | 0 | 60 | 35 | 20 | 65 | 40 |
| " | 8.96 | — | — | 30 | 15 | 5 | 65 | 45 | 25 | 70 | 45 |
| " | " | 12 | 4.48 | 30 | 10 | 0 | 65 | 40 | 30 | 70 | 40 |
| " | " | 7 | " | 35 | 5 | 0 | 60 | 45 | 20 | 75 | 35 |
| " | " | 1 | " | 20 | 20 | 0 | 65 | 45 | 15 | 60 | 40 |
| " | " | 16 | " | 20 | 20 | 0 | 65 | 50 | 20 | 70 | 50 |
| — | " | — | — | 0 | 0 | 0 | 0 | 0 | 20 | 20 | 25 |

EXAMPLE 64

This example shows the results of tests in various crop/weed combinations using PURSUIT® (No. 18) as the herbicidal component in the procedure described above. Test results are in Table 63.

TABLE 63

| Herb. No. 18 | Biocide No. 1 | Antidote | Rate | % Inhibition | | | | | | | |
|---|---|---|---|---|---|---|---|---|---|---|---|
| Kg/Ha) | (Kg/Ha) | No. | (Kg/Ha) | COTT | SOBE | CORN | GRSO | WHEA | RICE | GIFT | VELE |
| 0.14 | — | — | — | 50 | 10 | 40 | 75 | 35 | 60 | 80 | 100 |
| " | 8.96 | — | — | 55 | 15 | 75 | 75 | 40 | 65 | 85 | 100 |
| " | " | 12 | 4.48 | 45 | 10 | 65 | 75 | 30 | 60 | 85 | 95 |
| " | " | 7 | " | 50 | 15 | 70 | 80 | 45 | 70 | 90 | 95 |
| " | " | 1 | " | 50 | 15 | 65 | 70 | 35 | 65 | 85 | 95 |
| " | " | 16 | " | 50 | 20 | 70 | 75 | 25 | 65 | 90 | 100 |
| 0.035 | — | — | — | 45 | 10 | 25 | 65 | 20 | 45 | 80 | 95 |
| " | 8.96 | — | — | 45 | 5 | 70 | 70 | 35 | 40 | 85 | 95 |
| " | " | 12 | 4.48 | 45 | 5 | 60 | 75 | 10 | ·35 | 80 | 85 |
| " | " | 7 | " | 40 | 10 | 55 | 70 | 10 | 35 | 90 | 90 |
| " | " | 1 | " | 45 | 10 | 50 | 65 | 20 | 35 | 85 | 90 |
| " | " | 16 | " | 50 | 15 | 50 | 70 | 25 | 40 | 90 | 90 |
| 0.009 | — | — | — | 40 | 5 | 5 | 60 | 0 | 20 | 60 | 75 |
| " | 8.96 | — | — | 30 | 0 | 55 | 55 | 20 | 35 | 70 | 75 |

TABLE 63-continued

| Herb. No. 18 | Biocide No. 1 | Antidote | Rate | % Inhibition ||||||||
|---|---|---|---|---|---|---|---|---|---|---|---|
| Kg/Ha) | (Kg/Ha) | No. | (Kg/Ha) | COTT | SOBE | CORN | GRSO | WHEA | RICE | GIFT | VELE |
| " | " | 12 | 4.48 | 30 | 0 | 40 | 50 | 10 | 30 | 65 | 70 |
| " | " | 7 | " | 30 | 0 | 30 | 50 | 15 | 25 | 75 | 75 |
| " | " | 1 | " | 25 | 0 | 25 | 50 | 0 | 35 | 60 | 70 |
| " | " | 16 | " | 35 | 0 | 20 | 55 | 35 | 10 | 75 | 80 |
| — | " | — | — | 0 | 0 | 0 | 0 | 0 | 0 | 0 | 0 |

In the above Tables 61–63, it can be noted that interactions occurred between COUNTER 15G and BEACON in corn and wheat. Corn injury was effectively reduced by MON-7400, flurazole, MON-13900 and Antidote No. 33. The weak interaction effect on wheat was reduced slightly by these safeners.

The negative synergy between COUNTER and ACCENT was specific to corn and the resulting enhanced injury was corrected by the antidotes.

COUNTER and PURSUIT interacted negatively at one or more application rates to cause enhanced injury in corn, wheat and rice. Slight to moderate safening of corn was observed. Safening of weak interactions in wheat and rice ranged from slight to nil, depending on the antidote.

EXAMPLE 65

In another test in the several crops and weeds used in this test series, the herbicidal component was MON-12000 (No. 1); the other components were the same. the procedure used in this test was the same as that described in Example 62, modified to use a light overhead irrigation (about 0.32 cm/day) during days 4–7 of the test. Results are shown in Table 64.

various components of the system (biocide, herbicide and safener) were applied concurrently to soil covers of the seeded plants. Test results are shown in Table 65.

TABLE 64

| Herb. No. 1 | Biocide No. 1 | Antidote | Rate | % Inhibition ||||||||
|---|---|---|---|---|---|---|---|---|---|---|---|
| Kg/Ha) | (Kg/Ha) | No. | (Kg/Ha) | COTT | SOBE | CORN | GRSO | WHEA | RICE | GIFT | VELE |
| 0.28 | — | — | — | 60 | 70 | 10 | 20 | 0 | 40 | 40 | 100 |
| " | 8.96 | — | — | 55 | 75 | 60 | 15 | 35 | 25 | 85 | 100 |
| " | " | 12 | 4.48 | 40 | 80 | 10 | 0 | 0 | 10 | 75 | 95 |
| " | " | 7 | " | 50 | 75 | 20 | 15 | 0 | 20 | 90 | 95 |
| " | " | 1 | " | 35 | 70 | 10 | 0 | 0 | 25 | 85 | 95 |
| " | " | 16 | " | 50 | 75 | 15 | 10 | 30 | 25 | 90 | 95 |
| 0.07 | — | — | — | 20 | 45 | 0 | 0 | 0 | 0 | 20 | 90 |
| " | 8.96 | — | — | 0 | 70 | 10 | 15 | 0 | 10 | 70 | 85 |
| " | " | 12 | 4.48 | 40 | 70 | 10 | 15 | 0 | 10 | 70 | 85 |
| " | " | 7 | " | 0 | 55 | 5 | 0 | 0 | 0 | 80 | 90 |
| " | " | 1 | " | 35 | 75 | 15 | 0 | 0 | 10 | 70 | 85 |
| " | " | 16 | " | 0 | 60 | 0 | 0 | 20 | 0 | 80 | 90 |
| 0.018 | — | — | — | 10 | 15 | 0 | 0 | 0 | 0 | 0 | 70 |
| " | 8.96 | — | — | 15 | 5 | 0 | 0 | 0 | 0 | 70 | 75 |
| " | " | 12 | 4.48 | 10 | 5 | 0 | 0 | 0 | 0 | 30 | 50 |
| " | " | 7 | " | 25 | 10 | 0 | 0 | 0 | 10 | 80 | 60 |
| " | " | 1 | " | 20 | 35 | 5 | 0 | 0 | 0 | 50 | 65 |
| " | " | 16 | " | 30 | 10 | 0 | 0 | 25 | 10 | 75 | 75 |
| — | " | — | " | 0 | 0 | 0 | 0 | 0 | 10 | 30 | 0 |

EXAMPLE 66

In yet another test in this series, XRD-498 (Herbicide No. 21) was used as the herbicidal component in contact with COUNTER 15G in the presence of the above safeners. The

TABLE 65

| Herb. No. 1 Kg/Ha) | Biocide No. 1 (Kg/Ha) | Antidote No. | Rate (Kg/Ha) | % Inhibition ||||||||
|---|---|---|---|---|---|---|---|---|---|---|---|
| | | | | COTT | SOBE | CORN | GRSO | WHEA | RICE | GIFT | VELE |
| 0.28 | — | — | — | 40 | 20 | 10 | 80 | 0 | 60 | 70 | 90 |
| " | 8.96 | — | — | 75 | 15 | 75 | 85 | 85 | 90 | 90 | 90 |
| " | " | 12 | 4.48 | 35 | 15 | 20 | 55 | 20 | 70 | 85 | 85 |
| " | " | 7 | " | 60 | 5 | 40 | 70 | 30 | 70 | 95 | 90 |
| " | " | 1 | " | 45 | 5 | 20 | 65 | 70 | 95 | 95 | 90 |
| " | " | 16 | " | 40 | 10 | 25 | 85 | 25 | 85 | 90 | 95 |
| 0.07 | — | — | — | 20 | 0 | 0 | 40 | 0 | 40 | 60 | 80 |
| " | 8.96 | — | — | 20 | 0 | 0 | 20 | 0 | 25 | 65 | 80 |
| " | " | 12 | 4.48 | 10 | 0 | 0 | 20 | 0 | 20 | 80 | 75 |
| " | " | 7 | " | 0 | 0 | 10 | 30 | 25 | 30 | 60 | 65 |
| " | " | 1 | " | 20 | 0 | 5 | 25 | 25 | 25 | 80 | 75 |
| " | " | 16 | " | | | | | | | | |
| 0.018 | — | — | — | 0 | 0 | 0 | 0 | 0 | 0 | 20 | 15 |
| " | 8.96 | — | — | 0 | 0 | 0 | 15 | 0 | 0 | 30 | 10 |
| " | " | 12 | 4.48 | 15 | 0 | 0 | 0 | 0 | 0 | 25 | 0 |
| " | " | 7 | " | 0 | 0 | 0 | 0 | 0 | 0 | 60 | 0 |
| " | " | 1 | " | 10 | 0 | 0 | 0 | 10 | 10 | 40 | 10 |
| " | " | 16 | " | 0 | 0 | 0 | 20 | 20 | 0 | 30 | 30 |
| — | " | — | — | 0 | 0 | 0 | 0 | 0 | 0 | 30 | 0 |

The tests in Examples 65 and 66 showed that increased injury to corn and wheat occurred as a result of the interaction between COUNTER 15G and MON-12000. All four safeners provided good protection against corn injury. With the exception of Antidote No. 33, the test antidotes showed good wheat safening.

The combination of COUNTER 15G with the sulfonamide herbicide XRD-498 caused severe interactions with enhanced injury to corn and wheat. That injury was corrected to varying degrees by the antidotes. COUNTER 15G/XRD-498 negative synergy was also seen with cotton, grain sorghum and rice.

Other tests of the invention were conducted with respect to various modes of application of the components of the invention, viz., herbicide/biocide/antidote. Crop seeds, e.g., were coated with various safeners and contacted with COUNTER 15G and herbicides. Other PPI, POE and in-furrow tests were conducted and in all these areas, negative synergy was observed and safening effected, both to varying degrees depending upon the system components.

As will be apparent, the data in the above tables reflect the fact that interactions between insecticides and herbicides are susceptible to having their phytotoxicity to crops reduced by antidotal (safener) compounds, while still providing control or suppression of weeds. The data also reflect the common occurrence that the safening effect on various herbicides by safeners will have different degrees of effect depending upon a variety of factors, including, relative concentrations of herbicides and/or co-herbicides and/or antidotes, weather and soil conditions, water content, etc., as well appreciated in the art.

The herbicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate, and polymethylene bisnaphthalene sulfonate. Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from above 0.5 to 60 parts (preferably from 5–20 parts) of active ingredient, from about 0.25 to 25 parts (preferably 1–15 parts) of wetting agent, from about 0.25 to 25 parts (preferably 1.0–15 parts) of dispersant and from 5 to about 95 parts (preferably 5–50 parts) of inert solid extender, all parts being by weight of the total composition. Where required, from about 0.1 to 2.0 parts of the solid inert extender can be replaced by a corrosion inhibitor or antifoaming agent or both.

Other formulations include dust concentrates comprising from 0.1 to 60% by weight of the active ingredient on a suitable extender; these dusts may be diluted for application at concentrations within the range of from about 0.1–10% by weight.

Aqueous suspensions or emulsions may be prepared by stirring a nonaqueous solution of a water-insoluble active ingredient and an emulsification agent with water until uniform and then homogenizing to give stable emulsion of very finely divided particles. The resulting concentrated aqueous suspension is characterized by its extremely small particle size, so that when diluted and sprayed, coverage is very uniform. Suitable concentrations of these formulations contain from about 0.1–60%, preferably 5–50% by weight of active ingredient, the upper limit being determined by the solubility limit of active ingredient in the solvent. Concentrates are usually solutions of active ingredient in water-immiscible or partially water-immiscible solvents together with a surface active agent. Suitable solvents for the active ingredient of this invention include dimethylformamide, dimethylsulfoxide, N-methylpyrrolidone, hydrocarbons, and water-immiscible ethers, esters, or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5–60 parts) active ingredient, about 0.25 to 50 parts (preferably 1–25 parts) surface active agent and where required about 5 to 94 parts solvent, all parts being be weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate extender, a surface active agent can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention included, for example, triazines, ureas, sulfonylureas, carbamates, acetamides, acetanilides, uracils, acetic acid or phenol derivatives, thiolcarbamates, triazoles, benzoic acid and its derivatives, nitriles, biphenyl ethers, nitrobenzenes, etc.

Fertilizers useful in combination with the active ingredients include, for example, ammonium nitrate, urea, potash and superphosphate. Other useful additaments include materials in which plant organisms take root and grow such as compost, manure, humus, sand and the like.

As will be appreciated by those skilled in the art, the practice of this invention comprises the use of the antidotal compounds disclosed and claimed herein with any herbicidally-active azolopyrimidine sulfonamide or derivative compound which may optionally be combined with co-herbicides from many different classes of chemistry. Obviously, the above listings of exemplary compounds is not intended to be exhaustive, but representative. Again, as noted earlier herein, it is expected that not every combination of herbicide, insecticide and antidote will result in safening of all crops, but it is within the skill of the art to test any given herbicide/insecticide combination with an invention antidote in plant screens of any spectrum of plants and note the results.

The foregoing embodiments illustrate that the combinations of herbicide, insecticide and antidote of this invention are useful in controlling weeds while reducing herbicidal injury to crop plants under greenhouse and field test conditions.

The herbicide, insecticide, antidote, or a mixture thereof, may be applied to the plant locus without any adjuvants other than a solvent. As indicated above, these mixtures may be in the form of emulsifiable concentrates, microencapsulates, particulate solids, granules of varying particle size, e.g., water-dispersible or water-soluble granules or larger dry granules, pellets, wettable powders, dusts, solutions, aqueous dispersions, emulsions or other formulation types conventional in the art.

Examples of suitable adjuvants are finely-divided solid carriers and extenders including talcs, clays, pumice, silica, diatomaceous earth, quartz, Fuller's earth, sulfur, powdered cork, powdered wood, walnut flour, chalk, tobacco dust, charcoal, and the like. Typical liquid diluents include Stoddard's solvent, acetone, methylene chloride, alcohols, glycols, ethyl acetate, benzene, and the like. Liquids and wettable powders usually contain as a conditioning agent one or more surface-active agents in amounts sufficient to make a composition readily dispersible in water or in oil. The term "surface-active agent" includes wetting agents, dispersing agents, suspending agents, and emulsifying agents. Typical surface-active agents are mentioned in U.S. Pat. No. 2,547,724.

Compositions of this invention generally may contain from about 5 to 95 parts herbicide-insecticide-and-antidote, about 1 to 50 parts surface-active agent, and about 4 to 94 parts solvent, all parts being by weight based on the total weight of the composition.

The crop may be protected by treating the crop seed with an effective amount of antidote prior to planting. Generally, smaller amounts of antidote are required to treat such seeds. A weight ratio of as little as 0.6 parts of antidote per 1000 parts of seed may be effective. The amount of antidote utilized in treating the seed may be increased if desired. Generally, however, a weight ratio of antidote-to-seed weight may range from 0.1 to 10.0 parts of antidote per 1000 parts of seed. Since only a very small amount of active antidote is usually required for the seed treatment, the compound preferably is formulated as an organic solution, powder, emulsifiable concentrate, water solution, or flowable formulation, which can be diluted with water by the seed treater for use in seed treating apparatus. Under certain conditions, it may be desirable to dissolve the antidote in an organic solvent or carrier for use as a seed treatment or the pure compound alone may be used under properly controlled conditions.

For antidote seedcoating and for antidotes applied to soil in granular or liquid formulations, suitable carriers may be either solids, such as talc, sand, clay, diatomaceous earth, sawdust, calcium carbonate, and the like, or liquids, such as water, kerosene, acetone, benzene, toluene, xylene and the like, in which the active antidote may be either dissolved or dispersed. Emulsifying agents are used to achieve a suitable emulsion if two immiscible liquids are used as a carrier. Wetting agents may also be used to aid in dispersing the active antidote in liquids used as a carrier in which the antidote is not completely soluble. Emulsifying agents and wetting agents are sold under numerous tradenames and trademarks and may be either pure compounds, mixtures of compounds of the same general groups, or they may be mixtures of compounds of different classes. Typical satisfactory surface active agents which may be used are alkali metal higher-alkylarylsulfonates such as sodium dodecylbenzenesulfonate and the sodium salts of alkylnaphthalenesulfonic acids, fatty alcohol sulfates such as the sodium salts of monoesters of sulfuric acid with n-aliphatic alcohols containing 8–18 carbon atoms, long-chain quaternary ammonium compounds, sodium salts of petroleum-derived alkylsulfonic acids, polyethylene sorbitan monooleate, alkylaryl polyether alcohols, water-soluble lignin sulfonate salts, alkali casein compositions, long-chain alcohols usually containing 10–18 carbon atoms, and condensation products of ethylene oxide with fatty acids, alkylphenols and mercaptans.

The invention herein has been specifically exemplified with the herbicidal compounds identified above as Herbicide Nos. 1–28, co-Herbicides A-K, including several commercial herbicides, as representative of the herbicidal component; with Insecticide Nos. 1–10 as the biocidal component and by a wide variety of antidotes from multiple classes of chemistry, including, inter alia, numerous preferred dichloroacetamide antidote as representative of the compounds according to Formulae V and VI. It is to be understood that other compounds within the scope of the above formulae and other chemical classes are specifically contemplated as within the scope of this invention either as the herbicidal component or as a co-herbicide. For example, other triazolopyrimidine—and imidazolopyrimidine sulfonamides and their derivatives contemplated herein include the compounds described in the following U.S. patents and EP applications as relevant to the compounds of Formula I:

A. Compounds wherein R is the —$SO_2N(R_6)(R_7)$ moiety, A and B are both N and

1. $R_1$ and $R_2$ are discrete, uncombined radicals:
U.S. Pat. No. 4,889,553
U.S. Pat. No. 4,959,094

2. $R_1$ and $R_2$ are combined to form substituted and/or unsubstituted bivalent radicals which may contain one or more hetero atoms and saturated, partially saturated or unsaturated bonds:

| | |
|---|---|
| 4,740,233 | 4,854,964 |
| 4,741,764 | 4,960,455 |
| 4,755,212 | 4,859,231 |
| 4,818,273 | 4,795,483 |
| 4,886,883 | 4,910,306 |
| 4,954,163 | 4,959,473 |
| 4,979,981, | 5,013,351, |
| 5,041,157, | AU Appln. AU-A-68391, |
| EP Appln. 0 375 076, EP Appln 0 343 752 | |

B. Compounds analogous to those in A2 above, except that in Formula I only one of A or B is N while the other is $CR_3$ as defined above:
U.S. Pat. No. 4,731,446
U.S. Pat. No. 4,799,952
U.S. Pat. No. 4,892,576

C. Compounds wherein R is the —$N(R_4)SO_2R_5$ moiety, A and B are both N and $R_1$ and $R_2$ are combined to form a bivalent radical as in A2 above:
U.S. Pat. No. 4,638,075
U.S. Pat. No. 4,822,404
U.S. Pat. No. 4,650,892
U.S. Pat. No. 4,685,958

The above specifically mentioned herbicidal compounds used alone and/or as co-herbicides herein are intended merely as exemplary of the classes of herbicides which they represent. However, it is expressly contemplated that many other herbicidal compounds analogous to those represented herein having a variety of equivalent radicals substituted on the central nucleus may similarly be safened to various crop plants to a greater or lesser extent with the antidotal compounds of this invention. For example, other α-haloacetamide and α-haloacetanilide compounds useful as herbicides or co-herbicides herein are described in U.S. Pat. No. 3,442,945, 3,547,620, 3,574,746, 3,586,496, 3,830,841, 3,901,768, 4,249,935, 4,319,918, 4,517,011, 4,601,745, 4,657,579 and 4,666,502 and Australian Patent No. AU-Al-18044/88.

Herbicidally-useful thiocarbamate compounds are described in U.S. Pat. Nos. 2,913,327, 3,330,643 and 3,330,821.

Other herbicidal pyridine compounds are described in U.S. Pat. No. 4,692,184 and copending U.S. Ser. No. 07/134,231 and U.S. Pat. No. 4,826,532, both of common assignment herewith.

Herbicidally-useful heterocycyl phenyl ethers (especially pyrazolyl aryl ethers) are described, e.g., in U.S. Pat. No. 4,298,749.

Herbicidal diphenyl ethers and nitrophenyl ethers include 2,4-dichlorophenyl 4'-nitrophenyl ether ("nitrofen"), 2-chloro-1-(3'-ethoxy-4'-nitrophenoxy)-4-trifluoromethylbenzene ("Oxyfluorfen"), 2',4'-dichlorophenyl 3-methoxy-4-nitrophenyl ether ("Chlormethoxynil"), methyl 2-[4'-(2", 4"-dichlorophenoxy)-phenoxy]-propionate, N-(2'-phenoxyethyl)-2-[5'-(2"-chloro-4"-trifluoromethylphenoxy)-phenoxy] -propionamide, 2-methoxyethyl 2-[nitro-5-(2-chloro-4-trifluoromethylphenoxy)-phenoxyl-propionate and 2-chloro-4-trifluoromethylphenyl 3'-oxazolin-2'-yl-4'-nitrophenylether.

Another generic class of agrichemically-important herbicidal compounds specifically contemplated for use as co-herbicidal compounds in combination with the antidotal compounds of this invention are the urea derivatives. Important herbicidal ureas include 1-(benzothiazol- 2-yl)-1,3-dimethylurea; phenylureas, for example: 3-(3-chloro-p-tolyl)-1,1-dimethylurea ("chlorotoluron"), 1,1-dimethyl-3-(α,α,α-trifluoro-m-tolyl)urea ("fluometuron"), 3-(4-bromo-3-chlorophenyl)-methoxy-1-methylurea ("chlorbromuron"), 3-(4-bromophenyl)-1-methoxy- 1-methylurea ("metobromuron"), 3-(3,4-dichlorophenyl)- 1-methoxy-1-methylurea ("linuron"), 3-( 4-chlorophenyl)-1-methoxy-1-methylurea ("monolinuron"), 3-(3,4-dichlorophenyl)-1,1-dimethylurea ("diuron"), 3-( 4-chlorophenyl)-1,1-dimethylurea ("monuron") and 3-(3-chloro- 4-methoxyphenyl)-1,1-dimethylurea ("metoxuron");

Important herbicidal sulfonylureas and sulfonamides specifically contemplated as useful as the herbicidal component herein and/or a co-herbicides in compositions with the antidotal compounds of this invention include those disclosed in the following patents: U.S. Pat. Nos. 4,383,113, 4,127,405, 4,238,621, 4,432,245, 4,443,243, 4,478,635, 4,537,619, 4,479,821, 4,481,029, 4,514,212, 4,548,638, 4,420,325, 4,638,004, 4,675,046, 4,681,620, 4,741,760, 4,723,123, 4,411,690, 4,718,937, 4,620,868, 4,668,277, 4,592,776, 4,666,508, 4,670,559, 4,671,819, 4,696,695, 4,731,446, 4,744,814, 4,678,498, 4,759,791, 4,786,314, 4,786,734, 4,889,550, 4,931,081 and 4,6 68,279; EP Numbers 084224, 173312, 8778 0, 190105, 2563 96, 264021, 264672, 142152, 244847, 176304, 177163, 187470, 187489, 184385, 232067, 234352, 189069, 224842, 249938, 246984 and 282613, and German Offen. DE 3,618,004.

Among other herbicidal sulfonylureas disclosed in one or more of the above patents which are of particular interest are mentioned the species N-[(4-methoxy- 6-methylpyrimidin-2-yl)aminocarbonyl]-3-chloro-4-methoxy-carbonyl-1-methylpyrazole-5-sulfonamide; N-[(4,6-dimethoxypyrimidin-2- yl)aminocarbonyl]-3-chloro- 4-methoxycarbonyl-1-methylpyrazole-5-sulfonamide; N-[(4-methoxy-6-methylpyrimidin-2-yl)aminocarbonyl]-3-chloro-4-ethoxycarbonyl-1-methylpyrazole-5-sulfonamide; N-[(4,6-dimethoxypyrimidin-2-yl)aminocarbonyl]-3-chloro-4-ethoxycarbonyl-1-methylpyrazole-5-sulfonamide; N-[(4-methoxy- 6-methylpyrimidin-2-yl)aminocarbonyl]-3-bromo-4-ethoxycarbonyl-1-methylpyrazole-5-sulfonamide; N-[(4,6-dimethoxypyrimidin-2-yl)aminocarbonyl]-3-bromo-4-ethoxy-carbonyl- 1-methylpyrazole-5-sulfonamide; N-(methoxycarbonyl- 1-phenyl sulfonyl-N'-(bis-difluoromethoxypyrimidin- 2-yl)urea and N-[(4,6-dimethoxypyrimidin- 2-yl)-aminocarbonyl]-4-ethoxycarbonyl-1-methylpyrazole- 5-sulfonamide.

Other herbicidal imidazolinone, imidazolidinethione and imidazolidinone or -dione compounds useful as the herbicidal component within the purview of this invention or as co-herbicides which may be safened for use in various crops include compounds disclosed in the following exemplary publications: EP Application Numbers 436483, 041623, 133310, 198552, 216360 and 98029; JA 1109-790, JA 1197-580A, J6 1183-272A and J6 3196-750A; and Australian published Application No. AU 8661-073A, GB 2 172 886A and U.S. Pat. Nos. 4,188,487, 4,297,128, 4,562,257, 4,554,013, 4,608,079, 4,647,301, 4,638,068, 4,650,514, 4,709,036, 4,749,403, 4,749,404, 4,776,619, 4,776,876, 4,798,619, 4,741,767 4,851,031, 4,895,588, 4,992,092 and 5,062,881.

Still other classes of herbicidal compounds contemplated for combination with the herbicidal and insecticidal components and with the antidotes of this invention include the following representative species:

Triazines and triazinones: 2,4-bis-(isopropylamino)-6-methylthio- 1,3,5-triazine ("prometryn"), 2,4-bis-(ethylamino)- 6-methylthio-1,3,5-triazine ("simetryn"), 2-(1',2'-dimethylpropylamino)-4-ethylamino-6-methylthio-1,3,5-triazine ("dimethametryn"), 2-(chloro-4,6-bis-(ethylamino)-1,3,5-triazine ("simazine"), 2-tert-butyl-amino- 4-chloro-6-ethylamino-1,3,5-triazine ("terbuthylazine"), 2-tert-butylamino-4-ethylamino-6-methoxy-1,3,5-triazine ("terbumeton"), 2-tertbutylamino-4-ethylamino-6-methylthio-1,3,5-triazine ("terbutryn"), 2-ethylamino-4-isopropylamino-6-methylthio-1,3,5-triazine ("ametryn") and 3,4-his-(methylamino)-6-tert-butyl-4,4-dihydro-1,2,-4-triazin-5-one.

Oxadiazolones: 5-tert-butyl-3-(2', 4'-dichloro-5'-isopropoxyphenyl)- 1,3,4-oxadiazol-2-one ("Oxadiazon").

Phosphates: S-2-methylpiperidinocarbonylmethyl O,O-dipropyl phosphorodithioate ("Piperophos").

Pyrazoles: 1,3-dimethyl-4-(2',4'-dichlorobenzolyl)-5-(4'-tolylsulfonyloxy)-pyrazole; aryl- and heterocyclic-substituted pyrazoles, e.g., as exemplified in EP No. 0361114; Japanese Kokai No. JP 50137061 and U.S. Pat. No. 4,008, 249.

Also aryloxy- and α-(phenoxyphenoxy)-propionic acid derivatives and α-pyridyl-2-oxyphenoxy)-propionic acid derivatives. An exemplary herbicide in the latter class is propionic acid, 2-[4-(3-fluoro-5-chloro-pyridin- 2-yloxy)phenoxy] propynyl ester (code number CGA-184927).

Other heteroaromatic oxyphenoxypropionic acid esters include those of 1,3-benzoxazoloxyphenoxypropionic acid and ester derivatives, typified by (±)2-[4-(6-chloro-1,3-benzoxazol-2-yloxy)phenoxy] propionic acid ethyl ester (common name "fenoxaprop-ethyl").

Other herbicidal compounds useful as co-herbicides herein include aromatic and heterocyclic di- and triketones exemplified in U.S. Pat. Nos. 4,797,147, 4,853,028, 4,854, 966, 4,855,477, 4,938,796 and 4,869,748 and N-benzoyl-N-phenylalanine and its derivatives.

Still other co-herbicidal compounds contemplated herein are pyrrolidinones, e.g, the 1-phenyl-3-carboxyamidopyrrolidinones disclosed in U.S. Pat. No. 4,874,422, and the 1-phenyl-4-haloalkylpyrrolidones disclosed in U.S. Pat. No. 4,515,627, etc.

Still other herbicidal compounds useful as co-herbicides herein include benzoic acid derivatives of the type exemplified by 5-(2'-chloro-4'-trifluoromethyl-phenoxy)- 2-nitrobenzoic acid ("Acifluorfen"), 2,6-dichlorobenzonitrile ("dichlobenil"), 3,6-dichloro-2-methoxybenzoic acid ("dicamba"), etc. and compounds disclosed in U.S. Pat. Nos. 3,013,054, 3,027,248 and 3,979,437, etc.

Another class of herbicidal compounds suitable for use herein includes benzothiadiazin-4-(3H)-one-2,2-dioxide and its derivatives, exemplified by 3-isopropyl-1H-2,1,3-benzothiadiazin-4(3H)-one-2,2-dioxide (common name "bentazon").

In addition to the antidotal compounds exemplified herein, other representative antidotal compounds according to Formula V or other structure which are contemplated for use with one or more herbicides or co-herbicides disclosed herein are expressly disclosed in various patents, e.g., U.S. Pat. Nos. 3,959,304, 4,072,688, 4,137,070, 4,124,372, 4,124,376 4,483,706, 4,636,244, 4,033,756, 4,493,726, 4,708,735, 4,256,481, 4,199,506, 4,251,261, 4,070,389, 4,231,783, 4,269,775, 4,152,137, 4,755,218, 4,933,166, 4,954,161, 4,964,893, 4,623,727, 4,822,884, 4,851,031, 4,902,340, 4,749,406, 4,758,264, 4,785,105, 4,785,106 4,294,764, 5,028,256, 5,037,256, 5,041,157 and EP Patent Application Nos. 159,287, 159,290, 258,184, 94,349, 2,121, 403, 0253291, 0007588, 0190105, 0229649, 312762, 312763, 0430004 and 16618; PCT Patent Application Nos. WO 91/07874 and WO 91/08202; W. German Patent Application Nos. 28 28 222, 28 28 293.1, and 29 30 450.5, South African Patent No. 82/7681 and PRC Application No. 102 879-87.

Other antidotal compounds contemplated as suitable herein include 1-(5-chloro-isoquinon-8-yloxy)-1-methylhexyl acetate (Code No. CGA-185072), a safener for CGA-184927 herbicide in wheat, and 3-[(2,4-dichlorophenyl] 2-(trichloromethyl)-5-(ethoxycarbonyl)-triazol- 3-yl (Code No. HOE 70541), a safener also for use in wheat.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

We claim:

1. Herbicidal composition comprising
   (a) a herbicidally-effective amount of at least one herbicidal compound selected from the group consisting of sulfonylurea, imidazolinone, and azolopyrimidine sulfonamide herbicides which in the absence of component (c) interacts with a biocide to induce negative synergism;
   (b) an effective amount of an orthophosphate insecticide to control target insect pests and
   (c) an amount of at least one antidotal compound sufficient to reduce or eliminate said negative synergism.

2. Composition according to claim 1 wherein said antidotal compound is:
   N,N-diallyldichloroacetamide;
   N-(2-propenyl)-N-(1,3-dioxolanylmethyl)-dichloroacetamide;

Oxazolidine, 3-(dichloroacetyl)-2,2,5-trimethyl-;
Oxazolidine, 3-(dichloroacetyl)-2,2-dimethyl-5-phenyl-;
Oxazolidine, 3-(dichloroacetyl)-2,2-dimethyl-5-(2-furanyl)-;
Oxazolidine, 3-(dichloroacetyl)-2,2-dimethyl-5-(2-thienyl)-;
Pyridine, 3-[3-(dichloroacetyl)-2,2-dimethyl-5-oxazolidinyl]-;
4-(Dichloroacetyl)-1-oxa-4-azaspiro-(4,5)-decane;
4-(Dichloroacetyl)-3,4-dihydro-3-methyl-2H-2,4-benzoxazine;
Ethanone, 2,2-dichloro-1-(1,2,3,4-tetrahydro-1-methyl-2-isoquinolinyl)-;
N-(Dichloroacetyl)-1,2,3,4-tetrahydroquinaldine;
1-(Dichloroacetyl)-1,2,3,4-tetrahydroquinoline;
Cis/trans-piperazine, 1,4-bis(dichloro-1,4-acetyl)-2,5-dimethyl-;
1,5-Diazacyclononane, 1,5-bis-(dichloroacetyl;
1-Azaspiro[4,4]nonane, 1-(dichloroacetyl);
Pyrrolo[1,2-a]-pyrimidine-[6(2H)]-one, 1-(dichloroacetyl-)hexahydro-3,3,8a-trimethyl;
2,2-Dimethyl-3-(dichloroacetyl)-1,3-oxazole;
2,2-Dimethyl-5-methoxy-3-(dichloroacetyl)-1,3-oxazole;
Phosphorothioic acid, O,O-diethyl O-(3-methylphenyl)ester;
α-[(Cyanomethoxy)imino]benzeneacetonitrile,
α-[(1,3-Dioxolan-2-yl-methoxy)imino]benzeneacetonitrile,
O-[1,3-Dioxolan-2-ylmethyl]-2,2,2-trifluoromethyl-4'-chloroacetophenone oxime,
Benzenemethamine, N-[4-(dichloromethylene)-1,3-dithiolan-2-ylidene]-α-methyl, hydrochloride,
Diphenylmethoxy acetic acid, methyl ester,
1,8-Naphthalic anhydride,
4,6-Dichloro-2-phenyl-pyrimidine,
2-Chloro-N-[1-(2,4,6-trimethylphenyl)ethenyl]acetamide,
Ethylene glycol acetal of 1,1-dichloroacetone,
1,3-Dioxolane, 2-(dichloromethyl)-2-methyl-,
5-Thiazolecarboxylic acid, 2-chloro-4-(trifluoromethyl)-, (phenylmethyl) ester,
Phosphorothioic acid, O,O-diethyl O-(3-methylphenyl) ester,
4-Pentenenitrile, 2-methyl-2-[(4-methylphenyl)thio]-,
5-Chloro-8-(cyanomethoxy)quinoline,
1-Methylhexyl-2-(5-chloro-8-quinolinoxy)acetate,
O-(Methoxycarbonyl)-2-(8-quinolinoxy)acetamide oxime,
5-Oxazolecarboxylic acid, 2-[(2,2-dimethylethyl)amino]-4-(trifluoromethyl)-, ethyl ester,
Allyl-N-methyl dithiocarbanilate,
4-Isoxazolecarboxylic acid, 5-(2,4-dichlorophenyl)-, ethyl ester,
Pyrimidine, 4,6-dichloro-2-phenyl,
4-Pentenenitrile, 2-methyl-2-[(4-methylphenyl)thio]-,
Acetonitrile, [(5-chloro-8-quinolinyl)oxy]-,
Acetamide 2-(diphenylmethoxy)-N-methyl-,
Glycine, N-[bis(4-methoxyphenyl)-methyl]-, ethyl ester,
Glycine, N-[bis(4-chlorophenyl)-methyl]-, ethyl ester,
Acetic acid, [(10,11-dihydro-5H-dibenzo[a,d]cyclohepten-5-yl)oxy]-, 1,1-dimethylethyl ester,
Ethanethioamide, 2-(diphenylmethoxy)-,
Acetic acid, (diphenylmethoxy)-, propyl ester,
Acetic acid, (diphenylmethoxy)-, 2,2,2-trifluoroethyl ester,
Acetic acid, {phenyl[3-(trifluoro-methyl)phenyl]methoxy}-, 2-methyl-2-propanamine salt,
Acetic acid, (diphenylmethoxy)-, phenyl ester,
Ethanethioic acid, 2-(diphenylmethoxy)-, S-ethyl ester,
Acetic acid, (diphenylmethoxy-, 2-cyanoethyl ester,
Acetic acid, {phenyl[3-(trifluoro-methyl)phenyl]methoxy}-, 2,2,2-trifluoroethyl ester,
Acetic acid, (diphenylmethoxy)-, 2-propynyl ester,
Acetic acid, (diphenylmethoxy)-, 3-furanylmethyl ester,
Acetic acid, [bis(2,6-dimethylphenyl)-methoxy]-,
Acetic acid, (diphenylmethoxy)-, 3-nitrophenyl ester,
Acetic acid, {[bis(2,6-dimethyl-phenyl)]methoxy}-, ethyl ester,
Acetic acid, (diphenylmethoxy)-, 1-cyano-1-methylethyl ester,
5-Thiazolecarboxylic acid, 2-chloro-4-(trifluoromethyl)-, ethyl ester,
5-Thiazolecarboxylic acid, butyl ester, 2-chloro-, 4-(trifluoromethyl)
5-Thiazolecarboxylic acid, 2-chloro-, hexyl ester, 4-(trifluoromethyl)-,
5-Thiazolecarboxylic acid, 2-chloro-4-(trifluoromethyl)-, octyl ester,
5-Thiazolecarboxylic acid, 2-chloro-4-(trifluoromethyl)-, phenyl ester,
5-Thiazolecarboxylic acid, 2-chloro-4-(trifluoromethyl)-,
5-Thiazolecarboxylic acid, 2-[bromo-4-(trifluoromethyl)]-, ethyl ester,
5-Thiazolecarboxylic acid, 2-iodo-4-(trifluoromethyl)-, ethyl ester,
5-Thiazolecarboxylic acid, 2-chloro-4-(trifluoromethyl)-, 1-methylethanamine salt,
Benzylamine-, (alpha-methyl-, N-4-(methyl)-1,3-dithiol-2-ylidene) hydrochloride,
Pyridine, N-oxide, (3,4,5,6-tetrachloro-2-pyridylthio)-,
Acetic acid, [3,5-bis(trifluoromethyl)-phenoxy]-,
Propanamide, 2-chloro-N-[5-iodo-4-(trifluoromethyl)-2-thiazolyl-,
Cyclopropanecarbonitrile, 1-[(3,4-dimethylphenyl)thio]-,
Propanenitrile, 3-[[2-(1,1-dimethyl-ethyl)phenyl]thio]-,
4-Pentenenitrile, 2-methyl-2-[[4-(1-methylethyl)phenyl] thio]-,
Ethanimidamide, N'-[(methoxycarbonyl)-oxo]-2-(8-quinolinyloxy)-,
1(3H)-Isobenzofuranone, 3-[2-(2,5-dimethoxyphenyl)-2-oxoethyl]-,
Acetic acid, 2-(diphenylmethoxy) sodium salt hemihydrate,
Acetic acid, 2-(diphenylmethoxy)-, or
Acetic acid, (diphenylmethoxy)-, 2-propanamine salt.

3. Composition according to claim 2 wherein said compound (a) is N-(2,6-dichloro-3-methyl-phenyl)-1-(4-chloro-6-methoxypyrimidinyl-2-yl)-1H-1,2,4-triazole-3-sulphonamide; N-(2,6-difluorophenyl)-1-(pyrimidin-2-yl)-5-methyl-1,2,4-triazole-3-sulphonamide; N-(2,6-dichloro-3-methylphenyl)-1-(pyrimidin-2-yl)-5-methyl-1,2,4-triazole-3-sulphonamide; N-(2-methyl-6-nitrophenyl)-1-pyrimidin-2-yl)-5-methyl-1,2,4-triazole-3-sulphonamide; N-(2,6-difluorophenyl)-1-(4,6-dimethylpyrimidin- 2-yl)-5-methyl-1,2,4-triazole-3-sulphonamide; N-(2,6-dichlorophenyl)-1-pyrimidin- 2-yl)-5-methyl-1,2,4-triazole-3-sulphonamide; N-(2,6-di-fluorophenyl)-1-(4-methylpyrimidin- 2-yl)-5-methyl-1,2,4-triazole-3-sulphonamide; N-(2,6-difluorophenyl)-1-(4-methoxy-6-methylpyrimidin-2-yl)-5-methyl-1,2, 4-triazole-3-sulphonamide; N-(2,6-dichlorophenyl)-1-(4,6-dimethoxy-1,3,5-triazin-2-yl)-5-methyl-1,2,4-triazole-3-sulphonamide; N-(2,6-dichlorophenyl)-1-(4,6-dimethyl-pyrimidin-2-yl)-1,2,4-triazole-3-sulphonamide; N-(2,6-dichlorophenyl)-1-(4,6-dimethylpyrimidin-2-yl)-5-methyl-1,2,4-triazole- 3-sulphonamide; N-(2-methyl-6-nitrophenyl)-1-(4,6-dimethylpyrimidin-2-yl)-5-methyl-1,2,4-triazole-3-sulphonamide; N-(2,6-dichlorophenyl)-5-(2,5-dimethylpyrrol-1-yl)-1,2,4-triazole-3-sulphonamide; N-(2, 6-difluorophenyl)-5-(2,5-dimethylpyrrol-1-yl)-1,2,4-triazole-3-sulphonamide; N-(2,6-dichloro-3-methylphenyl)-1-(4,6-dimethylpyrimidin-2-yl)-1,2,4-triazole-3-sulphonamide; N-(2,6-dichlorophenyl)-5-amino-1-(4,6-dimethylpyrimidin-2-yl)-1,2,4-triazole-3-sulphonamide; or N-(2,6-dichloro-3-methylphenyl)-5-amino-1-(4,6-dimethoxy-1,3,5-triazin-2-yl)-1,2,4-triazole-3-sulphonamide.

4. Composition according to claim 2 wherein said compound (a) is
N-(2,6-difluorophenyl)-4,6-dimethylimidazolo[1,2-a]-pyrimidine-2-sulfonamide;
N-(2,6-difluorophenyl)-3-chloro-4,6-dimethylimidazolo[1,2-a]-pyrimidine-2-sulfonamide;
N-(2,6-difluorophenyl)-3-bromo-4,6-dimethylimidazolo[1,2-a]-pyrimidine-2-sulfonamide;
N-(2,6-difluorophenyl)-3-methylthio-4,6-dimethylimidazolo[1,2-a]-pyrimidine-2-sulfonamide;
N-(2,6-dichlorophenyl)-4,6-dimethylimidazolo[1,2-a]-pyrimidin e-2-sulfonamide;
N-(2,6-difluorophenyl)-3-cyano-4,6-dimethylimidazolo[1,2-a]-pyrimidine-2-sulfonamide;
N-(2,6-difluorophenyl)-N-benzyl-3-chloro-4,6-dimethylimidazolo[1,2-a]-pyrimidine-2-sulfonamide;
N-(2-trifluoromethylphenyl)-4,6-dimethylimidazolo[1,2-a]-pyrimidine-2-sulfonamide;
N-(2-trifluoromethylphenyl)-3-chloro-4,6-dimethylimidazolo[1,2-a]-pyrimidine-2-sulfonamide;
N-(2-carbomethoxy-6-methylphenyl)-3-chloro-4,6-dimethylimidazolo[1,2-a]-pyrimidine- 2-sulfonamide;
N-(2,6-dichlorophenyl)-3-chloro-4,6-dimethylimidazolo[1,2-a]-pyrimidine-2-sulfonamide;
N-(2-chloro-6-methylphenyl)-3-chloro-4,6-dimethylimidazolo[1,2-a]-pyrimidine-2-sulfonamide;
N-(2,6-difluorophenyl)-4-chloro-6-methylimidazolo[1,2-a]-pyrimidine-2-sulfonamide;
N-(2,6-difluorophenyl)-4-methoxy-6-methylimidazolo[1,2-a]-pyrimidine-2-sulfonamide;
N-(2,6-difluorophenyl)-4,6-dichloroimidazolo-[1,2-a]-pyrimidine-2-sulfonamide; or
N-(2,6-difluorophenyl)-4,6-bismethoxyimidazolo-[1,2-a]-pyrimidine-2-sulfonamide monohydrate.

5. Composition according to claim 1 wherein said compound (a) is
N-(2,6-Dichlorophenyl)-6,7-dihydro-5,6-dimethyl-3-methoxycarbonyl-7-oxo-pyrazolo[ 1,5-a]-[1,3,5]-triazine-2-sulphonamide;
N-(2,6-Difluorophenyl)-6,7-dihydro-5,6-dimethyl-3-methoxycarbonyl-7-thioxo-pyrazolo[ 1,5-a]-[1,3,5]-triazine-2-sulphonamide;
N-(2,6-Difluorophenyl)-6,7-dihydro-5,6-dimethyl-3-methoxycarbonyl-7-oxo-pyrazolo[ 1,5-a]-[1,3,5]-triazine-2-sulphonamide;
N-(2,6-Dichlorophenyl)-6,7-dihydro-5,6-dimethyl-3-methoxycarbonyl-7-thioxopyrazolo[ 1,5-a]-[1,3,5]-triazine-2-sulphonamide;
N-(2,6-Dichloro-3-methylphenyl)-6,7-dihydro-5,6-dimethyl-3-methoxycarbonyl-7-oxopyrazolo[1,5-a]-[1,3,5]-triazine-2-sulphonamide;
N-(2,6-Dichloro-3-methylphenyl)-6,7-dihydro-5,6-dimethyl-3-methoxycarbonyl-7-thioxopyrazolo-[1,5-a]-[1,3,5]-triazine-2-sulphonamide;
N-(2-Chloro-6-fluorophenyl)-6,7-dihydro-5,6-dimethyl-methoxycarbonyl-7-oxopyrazolo-[1,5-a][1,3,5]-triazine-2-sulphonamide;
N-(2-Chloro-6-fluorophenyl)-6,7-dihydro-5,6-dimethyl-3-methoxycarbonyl-7-thioxopyrazolo-[1,5-a][1,3,5]-triazine-2-sulphonamide;
N-(2-Chloro-6-methylphenyl)-6,7-dihydro-5,6-dimethyl-3-methoxycarbonyl-7-oxopyrazolo-[1,5-a][1,3,5]-triazine-2-sulphonamide;
N-(2-Chloro-6-methylphenyl)-6,7-dihydro-5,6-dimethyl-3-methoxycarbonyl-7-thioxopyrazolo-[1,5-a][1,3,5]-triazine-2-sulphonamide;
N-(2,6-Dibromophenyl)-6,7-dihydro-5,6-dimethyl-3-methoxycarbonyl-7-oxopyrazolo[ 1,5-a][1,3,5]-triazine-2-sulphonamide; or
N-(2,6-Dibromophenyl)-6,7-dihydro-5,6-dimethyl-3-methoxycarbonyl-7-thioxopyrazolo[ 1,5-a]-[1,3,5]-triazine-2-sulfonamide.

6. Composition according to claim 2 wherein said compound (a) is N-(2,6-difluorophenyl)-thiazole[3,2-b][1,2,4]triazole-2-sulfonamide.

7. Composition according to claim 2 wherein said compound (a) is:
N-5,7-dimethyl-4,5,6,7-tetrahydro-1,2,4-triazolo-[1,5-a]-pyrimidine-2-yl- 2-(2,6-dichlorophenyl)sulfonamide;
N-5-methyl-4,5,6,7-tetrahydro-1,2,4-triazolo[1,5-a]-pyrimidine-2-yl-2-(2,6-difluorophenyl)sulfonamide;
N-(5,7-Dimethyl-1,2,4-triazolo[1,5-a]-pyrimidin-2-yl)-2-thiophene sulfonamide;
N-Acetyl-2,6-dichloro-N-(5,7-dimethyl-1,2,4-triazolo[1,5-a]-pyrimidin-2-yl)benzenesulfonamide;
N-(5-Amino-1,2,4-triazol-3-yl)-2-nitrobenzenesulfonamide;
N-(5,7-Dimethyl-1,2,4-triazolo[1,5-a]-pyrimidin-2-yl)-2-nitrobenzenesulfonamide;
N-(5-Amino-1,2,4-triazol-3-yl)-2,5-dichlorobenzenesulfonamide;
N-(5,7-Dimethyl-1,2,4-triazolo[1,5-a]pyrimidin-2-yl)-2,5-dichlorobenzenesulfonamide;
2-Chloro-N-(5-methyl-7-trifluoromethyl-1,2,4-triazolo[1,5-a]pyrimidin-2-yl)benzenesulfonamide
2-Chloro-N-(7-methyl-1,2,4-triazolo[1,5-a]-pyrimidin-2-yl)benzenesulfonamide;
2-Chloro-N-(1,2,4-triazolo[1,5-a]pyrimidin-2-yl)-benzenesulfonamide;
2-Chloro-N-(6-Chloro-1,2,4-triazolo[1,5-a]-pyrimidin-2-yl)benzenesulfonamide;
2-Chloro-N-(6-methyl-1,2,4-triazolo[1,5-a]-pyrimidin-2-yl)benzenesulfonamide; or
N-(5-Amino-1,2,4-triazol-3-yl)-2,6-dichloro-benzenesulfonamide.

8. Composition according to claim 2 wherein said compound (a) is
N-(5,7-dimethyl)-6,7-dihydro-[1,2,4]-triazole-[1,5-a]-[1,3,5]-triazine-2-( 2,6-difluorophenyl)-sulfonamide;
N-(5-methyl)-6,7-dihydro-[1,2,4]-triazole[1,5-a]-[1,3,5]-triazine-2-( 2,6-difluorophenyl)-sulfonamide;
N-(7-methoxy-6,7-dihydro-[1,2,4]-triazole[1,5-a]-[1,3,5]-triazine-2-( 2,6-dichlorophenyl)-sulfonamide;
N-(5,7-dimethoxy)-6,7-dihydro-[1,2,4]-triazole-[1,5-a][1,3,5]-triazine-2-(2,3,6-trimethylphenyl)sulfonamide;
N-(5-chloro)-6,7-dihydro-[1,2,4]-triazole[1,5-a]-[1,3,5]-triazine-2-(2-acetyl- 6-methyl-phenyl)-sulfonamide; or
N-(5-methoxymethyl)-6,7-dihydro[1,2,4]-triazole-[1,5-a][1,3,5]-triazine-2-(2,6-difluorophenyl)-sulfonamide.

9. Composition according to claim 2 wherein said compound (a) is
N-(5,7-dimethyl)-6,7-dihydro-[1,2,4]-triazole-[1,5-1][1,3,5]-triazine- 2-thiophenesulfonamide;
N-(5-methyl)-6,7-dihydro-[1,2,4]-triazole-[1,5-a]-[1,3,5]-triazine- 2-thiophene-sulfonamide;
N-(5,7-dimethoxy)-6,7-dihydro-[1,2,4]-triazole-[1,5-a][1,3,5]-triazine- 2-furanesulfonamide;
N-(5-methoxymethyl)-6,7-dihydro-[1,2,4]-triazole-[1,5-a][1,3,5]-triazine-furanesulfonamide;
N-(5-methyl)-6,7-dihydro-[1,2,4]-triazole-[1,3,5]-triazine-2-(3-chloro-1-methyl- 5-trifluoromethylpyrazol-4-yl)sulfonamide; or N-(5,7-dimethyl)-6,7-dihydro-[1,2,4]-triazole-[1,3,5]-triazine-2-[4-chloro-5-methyl-sulfonyl)pyrazol-4-yl]sulfonamide.

10. Composition according to claim 2 wherein said compound (a) is a sulfonylurea compound selected from the group consisting of Benzenesulfonamide, 2-chloro-N-[[(4-methoxy-6-methyl-1,3,5-triazin-2-yl)amino]carbonyl];

Benzoic acid, 2-[[[[(4-chloro-6-methoxy-2-pyrimidin-2-yl)amino]carbonyl]-amino] -sulfonyl]-ethyl ester;

2-Thiophenecarboxylic acid, 3-[[[[(4,6-di-methoxy-1,3,5-triazin-2-yl)amino] carbonyl]amino]sulfonyl]-, methyl ester;

Benzoic acid, 2-[[[[(4,6-dimethyl-2-pyrimidinyl)amino]carbonyl]-amino] sulfonyl]-, methyl ester;

Benzenesulfonamide, 2-(2-chloroethoxy)-N-[[(4-methoxy-6-methyl-1,3,5-triazin-2-yl)amino]carbon yl];

Benzoic acid, 2-[[[[(4-methoxy-6-methyl-1,3,5-triazin-2-yl)amino]-carbonyl] amino]sulfonyl]-, methyl ester;

Benzoic acid, 2-[[[[(4,6-di(difluoro-methoxy)-2-pyrimidin-2-yl]amino]-carbonyl] amino]sulfonyl]-, methyl ester;

Pyridine, 3-[[[[(4,6-dimethyl-2-pyrimidin-2-yl)amino]carbonyl]amino] sulfonyl]-N,N-dimethylcarbamoyl;

Pyridine, 3-[[[[(4,6-dimethoxy-2-pyrimidin-2-yl)amino]carbonyl]amino] sulfonyl]ethylsulfonyl;

Benzenesulfonamide, 2-(methoxyethoxy)-N-[[(4,6-dimethoxy-1,3,5-triazine- 2-yl)amino]carbonyl];

Methyl-2-[[[[(4,6-dimethoxy-2-pyrimidin-2-yl)amino]carbonyl]amino] sulfonyl]methyl]benzoate;

N-[(4,6-dimethoxypyrimidin-2-yl)aminocarbonyl]-3-chloro-4-methoxycarbonyl-1-methoxycarbonyl-1-methylpyrazole;

N-[(4,6-dimethoxypyrimidin-2-yl)aminocarbonyl]-4-ethoxycarbonyl-1-methylpyrazole;

N-[(4,6-dimethylpyrimidin-2-yl)aminocarbonyl]-1-(1-methylethyl)-1H-imidazole- 2-sulfonamide;

N-[(4-methoxy-6-methylpyrimidin-2-yl)aminocarbonyl]-1-(1-methylethyl)-1H-imidazole-2-sulfonamide;

N-[(4,6-dimethoxypyrimidin-2-yl)aminocarbonyl]-1-(1methylethyl)1H-imidazole- 2-sulfonamide;

N-[(4,6-dimethylpyrimidin-2-yl)aminocarbonyl]-1-ethyl-1H-imidazole-2-sulfonamide;

N-[(4-methoxy-6-methylpryimidin-2yl)aminocarbonyl]-1-ethyl-1H-imidazole-2-sulfonamide;

N-[-(4,6-dimethoxypyrimidin-2-yl)aminocarbonyl]-1-ethyl-1H-imadazole-2-sulfonamide; and N-[(4,6-dimethoxypyrimidin-2-yl)aminocarbonyl]-5-bromo-1-methyl-1H-imidazole-4-sulfonamide.

11. Composition according to claim 2 wherein said herbicidal component is an imidazolinone compound.

12. Composition according to claim 11 wherein said imidazolinone compound is:

3-Quinolinecarboxylic acid, 2-[4,5-dihydro-4-methyl-4-(1-methylethyl)-5-oxo-1H-imidazol- 2-yl]-;

3-Pyridinecarboxylic acid, 2-[4,5-dihydro-4-methyl-4-(1-methylethyl)-5-oxo-1H-imidazol- 2-yl]-;

Benzoic Acid, 2-[4,5-dihydro-4-methyl-4-(1-methylethyl)-5-oxo-1H-imidazol-2-yl]-4(or 5)-methyl;

3-Pyridinecarboxylic acid, 5-ethyl-2-[4,5-dihydro-4-methyl- 4-(1-methylethyl)-5-oxo-1H-imidazol-2-yl]-;

3-Pyridinecarboxylic acid, 2-[4,5-dihydro-4-methyl-4-(1-methylethyl)-5-oxo-1H-imidazol- 2-yl]-5-methyl-, ammonium salt;

2-(5-Methyl-5-trifluoromethyl-1-H-imidazol-4-on-2-yl)-pyridin-3-carboxylic acid;

2-(5-Methyl-5-trifluoromethyl-1-H-imidazol-4-on-2-yl) 5-(m)ethyl isonicotinic acid;

2-[5-(1-Fluoroethyl)-5-(m) ethyl-H-imidazol-4-on-2-yl] isonicotinic acid;

2-(5-(Difluoromethyl-5-(m) ethyl1-H-imidazol- 4-on-2-yl]-5-(m) ethylisonicotinic acid;

2-(5-(1-Fluoroethyl)-5-(m) ethyl)-imidazol-4-on-2-yl]isonicotinic (m) ethyl ester.

13. Composition according to claim 2 wherein said compound (b) is terbufos, chlorpyrifos, disulfoton, phorate, dimethoate or malathion.

14. Composition according to claim 13, further containing as a biocide one of the fungicidal compounds anilazine, benodanil, benomyl, butacarb, captafol, captan, carboxin, chloranil, chlorbromuron, chloroneb, chlorothalnil, chlorquinox, dazomet, dichlofluanid, dichlone, dichlorophen, dichloran, dithianon, dodine, edifenphos, Dowside-A, ferbam, folpet, mancozeb, maneb, pyrazophos, thiabendazole, thiram, zineb or ziram and/or one of the nematicides fensulfothion, carbofuran, ethoprop, fenamiphos, dichloropropene, aldicarb or oxamyl and/or one of the miticides formetanate hydrochloride, propargite, profenofos, DIKAR®, ethion, dinocap, dicofol, amitraz, quinomethionate, cyhexatin, fenbutatinoxide or phosalone.

15. Composition according to claim 14 wherein said compound (c) is N,N-diallyldichloroacetamide or N-(2-propenyl)-N-(1,3-dioxolanylmethyl)dichloroacetamide.

16. Composition according to claim 2 wherein said compound (a) is 5-methyl-N-( 2,6-difluorophenyl)-1,2,4-triazolo [1,5a]-pyrimidine-2-sulfonamide.

17. Composition according to claim 2 wherein said compound (a) is 5,7-di-methyl-N-(2,6-dichlorophenyl)-1,2,4-triazolo[1,5-a]-pyrimidine-2-sulfonamide;

5-methyl-N-(2,6-dichlorophenyl)-1,2,4-triazolo[1,5-a]-pyrimidine-2-sulfonamide;

5-methyl-N-(2-bromo-6-chlorophenyl)-1,2,4-triazolo[1,5-a] -pyrimidine-2-sulfonamide;

5-methyl-N-(2,6-difluoro-3-methylphenyl)-1,2,4-triazolo-[1,5-a]-pyrimidine-2-sulfonamide;

5-methyl-N-(2,6-difluorophenyl)-1,2,4-triazolo[1,5-a]-pyrimidine-2-sulfonamide;

5,7-dimethoxy-N-(2,6-dichloro-3-methylphenyl)-1,2,4-triazolo-[1,5-a]-pyrimidine- 2-sulfonamide;

5,7-dimethoxy-N-(2-methoxy-6-trifluoromethyl-phenyl)-1,2,4-triazolo-[1,5-a]-pyrimidine- 2-sulfonamide;

5-methyl-7-methylthio-N-(2,6-dichlorophenyl)-1,2,4-triazolo-[1,5-a]-pyrimidine- 2-sulfonamide;

5-methyl-7-methylthio-N-(2-trifluoromethylphenyl)-1,2,4-triazolo-[1,5-a]-pyrimidine- 2-sulfonamide;

7-ethoxy-5-methyl-N-(2,6-dichloro-3-methylphenyl)-1,2,4-triazolo-[1,5-a]pyrimidine- 2-sulfonamide;

5,7-dimethyl-N-(2-chloro-6-phenylphenyl)-1,2,4-triazolo[1,5-a]pyrimidine-2-sulfonamide;

5-methyl-N-(2-chloro-6-methylphenyl)-1,2,4-triazolo[1,5-a]-pyrimidine-2-sulfonamide;

5-methyl-N-(2-methyl-6-nitrophenyl)-1,2,4-triazolo[1,5-a]-pyrimidine-2-sulfonamide;

Methyl-3-methyl-N-(5,7-dimethyl-1,2,4-triazolo-[1,5-a]-pyrimidine-2-sulfonyl)anthranilate;

Methyl-3-methyl-N-(5-methyl-7-ethoxy-1,2,4-triazolo-[1,5-a]-pyrimidine-2-sulfonyl)anthranilate;

Isopropyl-3-methyl-N-(5-methyl-1,2,4-triazolo-[1,5-a]-pyrimidine-2-sulfonyl)anthranilate;

6-Methyl-N-(2-bromo-6-methylphenyl)-1,2,4-triazolo-[1,5-a]-pyrimidine-2-sulfonamide;

6-Methyl-N-(2-fluoro-6-chlorophenyl)-1,2,4-triazolo-[1,5-a]-pyrimidine-2-sulfonamide;

6-Methyl-N-(2-chloro-6-methylphenyl)-1,2,4-triazolo[1,5-a]-pyrimidine-2-sulfonamide;

6-Methyl-N-(2-methyl-6-nitrophenyl)-1,2,4-triazolo-[1,5-a]-pyrimidine-2-sulfonamide;
7-Ethoxy-5-methyl-N-(2-trifluoromethylphenyl)-1,2,4-triazolo-[1,5-a]-pyrimidine- 2-sulfonamide;
7-Methoxy-5-methyl-N-(2,6-dichloro-3-methylphenyl)-1,2,4-triazolo-[1,5-a]-pyrimidine- 2-sulfonamide;
7-Ethoxy-5-methyl-N-(2-bromo-6-chloro-3-methylphenyl)-1,2,4-triazolo-[ 1,5-a]-pyrimidine-2-sulfonamide;
5,7-Dimethoxy-N-(2,6-dibromo-3-methylphenyl)-1,2,4-triazolo-[1,5-a]-pyrimidine- 2-sulfonamide;
5,7-Dimethoxy-N-(2,6-dichlorophenyl)-1,2,4-triazolo-[1,5-a]-pyrimidine-2-sulfonamide;
7-Methyl-N-(2,6-dichlorophenyl)-1,2,4-triazolo-[1,5-a]-pyrimidine-2-sulfonamide;
N-(2,6-Dichlorophenyl)-1,2,4-triazolo-[1,5-a]-pyrimidine-2-sulfonamide;
7-Ethoxy-5-methyl-N-(2,6-dibromo-3-methylphenyl)-1,2,4-triazolo-[1,5-a]-pyrimidine- 2-sulfonamide;
6-Chloro-N-(2,6-difluorophenyl)-1,2,4-triazolo-[1,5-a]-pyrimidine-2-sulfonamide;
5-Methyl-7-trifluoromethyl-N-(2-methoxy-6-trifluoromethylphenyl)-1,2,4-triazolo-[ 1,5-a]-pyrimidine-2-sulfonamide;
Methyl-3-fluoro-N-(6-chloro-1,2,4-triazolo-[1,5-a]-pyrimidine-2-sulfonyl)anthranilate;
5,7-Dimethyl-N-(1,3-dimethyl-5-trifluoromethyl-4-pyrazolyl)-1,2,4-triazolo-[ 1,5-a]-pyrimidine-2-sulfonamide;
5-Methyl-N-(1,3-dimethyl-5-trifluoromethyl-4-pyrazolyl)-1,2,4-triazolo-[1,5-a]-pyrimidine- 2-sulfonamide;
5,7-Dimethyl-N-(1-methyl-4-ethoxycarbonyl-5-pyrazolyl)-1,2,4-triazolo-[ 1,5-a]-pyrimidine-2-sulfonamide;
5,7-Dimethoxy-N-(2-chloro-1-napthyl)-1,2,4-triazolo-[1,5-a]pyrimidine-2-sulfonamide;
5-Methyl-7-methoxy-N-(2-chloro-1-naphthyl)-1,2,4-triazolo-[1,5-a]-pyrimidine- 2-sulfonamide;
5-Methyl-7-ethoxy-N-(2-chloro-1-naphthyl)-1,2,4-triazolo-[1,5-a]-pyrimidine-2-sulfonamide;
5-Methyl-N-(2-methylpropanoyl)-N-(2,6-difluorophenyl)-1,2,4-triazolo-[1,5-a]-pyrimidine- 2-sulfonamide;
5-Methyl-N-acetyl-N-(2,6-dichlorophenyl)-1,2,4-triazolo-[1,5-a]-pyrimidine-2-sulfonamide;
5,7-Dimethyl-2-(N-[2-chloro, 6-propargyloxyphenyl]sulphamoyl)-1,2,4-triazolo-[ 1,5-a]-pyrimidine;
5,7-Dimethyl-2-(N-[2-chloro-6-(2-ethoxyethoxy)phenyl]-sulphamoyl)-1,2,4-triazolo-[ 1,5-a]-pyrimidine;
5,7-Dimethyl-2-(N-[2-benzyloxy-6-chlorophenyl]sulphamoyl)-1,2,4-triazolo- 1,5-a]-pyrimidine;
5,7-Dimethyl-2-(N-[2-allyloxy-6-fluorophenyl]sulphamoyl)-1,2,4-triazolo- 1,5-a]-pyrimidine;
5,7-Dimethyl-2-(N-[2-chloro-6-(2-methoxymethoxy)phenyl]sulphamoyl)- 1,2,4-triazolo-[1,5-a]pyrimidine;
5,7-Dimethyl-2-(N-[2-chloro-6-(2-hydroxyethoxy)phenyl]sulphamoyl)-1,2,4-triazolo-[ 1,5-a]-pyrimidine;
5,7-Dimethyl-2-(N-[2-2-ethoxyethoxy)-6-fluorophenyl]sulphamoyl)-1,2,4-triazolo-[ 1,5-a]-pyrimidine;
5,7-Dimethyl-2-(N-[2-fluoro-6-(2-methylthioethoxy)phenyl]sulphamoyl)- 1,2,4-triazolo-[1,5-a]-pyrimidine;
5,7-Dimethyl-2-(N-[2-chloro-6-(2-phenoxyethoxy)phenyl]sulphamoyl)-1,2,4-triazolo[ 1,5-a]-pyrimidine;
5,7-Dimethyl-2-(N-[2-chloro-6-(2-methoxyethoxy)phenyl]sulphamoyl-1,2,4-triazolo-[1,5-a]-pyrimidine;
5,7-Dimethyl-2-(N-[2-chloro-6-(2-n-propoxyethoxy)phenyl]sulphamoyl)- 1,2,4-triazolo[1,5-a]-pyrimidine;
5,7-Dimethyl-2-(N-[2-chloro-6-(3-methoxy-n-propoxy)phenyl]-sulphamoyl)-1,2,4-triazolo-[1,5-a]-pyrimidine;
5,7-Dimethyl-2-(N-[2-chloro-6-(2-isopropoxy)-ethoxyphenyl]sulphamoyl)-1,2,4-triazolo-[1,5-a]-pyrimidine;

5,7-Dimethyl-(N-[2-fluoro-6-(2-n-propoxyethoxy)phenyl] sulphamoyl-1,2,4-triazolo-[ 1,5-a]-pyrimidine;
5,7-Dimethyl-2-(N-[2-(2-ethoxyethoxy)phenyl]sulphamoyl)-1,2,4-triazolo-[ 1,5-a]-pyrimidine;
5,7-Dimethyl-2-(N-[2,6-di(2-ethoxyethoxy)phenyl]sulphamoyl)-1,2,4-triazolo-[ 1,5-a]-pyrimidine;
5,7-Dimethyl-2-(N-[2-2-ethoxyethoxy)-6-methoxyphenyl] sulphamoyl)-1,2,4-triazolo-[1,5-a]-pyrimidine;
5,7-Dimethyl-2-(N-[2-chloro-6-tetrahydrofurfur2-yl-oxyphenyl]-sulphamoyl)-1,2,4-triazolo-[1,5-a]-pyrimidine;
5,7-Dimethyl-2-(N-[2-(2-emthoxyethylamino)phenyl]sulphamoyl)-1,2,4-triazolo[1,5-a]-pyrimidine;
5,7-Dimethyl-2-(N-[2-(2-methoxyethylthiophenyl]sulphamoyl)-1,2,4-triazolo-[ 1,5-a]-pyrimidine;
5,7-Dimethyl-2-(N-acetyl-N-[2-chloro-6-(2-ethoxyethoxy)phenyl]sulphamoyl)-1,2,4-triazolo-[ 1,5-a]-pyrimidine;
5,7-Dimethyl-2-(N-acetyl-N-[2-chloro-6-(2-methoxyethoxy)phenyl]sulphamoyl)-1,2,4-triazolo-[1,5-a]-pyrimidine;
5,7-Dimethyl-2-(N-methyl-N-[2-chloro-6-(2-ethoxyethoxy)phenyl]sulphamoyl-1,2,4-triazolo-1,5-a]-pyrimidine;
5,7-Dimethyl-2-(N-[2-(2-ethoxyethoxy)-6-nitrophenyl]sulphamoyl-1,2,4-triazolo-[ 1,5-a]pyrimidine;
5Methoxymethyl-N-(2-chloro-6-methylphenyl)-1,2,4-triazolo-[2,5-a]-pyrimidine- 2-sulfonamide;
5,7-Dimethyl-N-(2-chloro-6-methylphenyl)-1,2,4-triazolo [1,5-a]-[4H,7H]-dihydropyrimidine-2-sulphanonamide;
7-Methyl-N-(2-chloro-6-methylphenyl)-1,2,4-triazolo-[1,5-a][4H,7H]-dihydropyrimidine- 2-sulphonamide;
5,7-Dimethyl-N-(2-chloro-6-ethoxyphenyl)-1,2,4-triazolo-[1,5-a][4H, 7H]-dihydropyrimidine-2-sulphonamide; or
5,7-Dimethyl-N-(2-chloro-6-isopropoxyphenyl)-1,2,4-triazolo-[1,5-a][4H, 7H]-dihydropyrimidine-2-sulphonamide.

18. Composition comprising as the herbicidal component: nicosulfuron, primisulfuron, DPX E9636, NC-311, NC-319, or XRD-498; as the biocidal component terbufos, chlorpyrifos, disulfoton or phorate; and as the antidotal component: dichlormid, PPG-1292, AD-67, MON-7400 or MON-13900.

19. Method for combatting negative synergism in crops induced by the interaction of a herbicidal compound selected from sulfonylurea, imidazolinone, azolopyrimidine sulfonamide herbicides and an orthophosphate insecticide comprising the step of treating said crop with (a) a herbicidally-effective amount of at least one herbicidal compound selected from the group consisting of sulfonylurea, imidazolinone, and azolopyrimidine sulfonamide herbicides which in the absence of component (c) interacts with a biocide to induce negative synergism;

(b) an effective amount of an orthophosphate insecticide to control target insect pests; and (c) an amount of at least one antidotal compound in sufficient amount to reduce or inhibit said negative synergism.

20. Method according to claim 19 wherein said antidotal compound is

N,N-diallyldichloroacetamide;
N-(2-propenyl)-N-(1,3-dioxolanylmethyl)-dichloroacetamide;
Oxazolidine, 3-(dichloroacetyl)-2,2,5-trimethyl-;
Oxazolidine, 3-(dichloroacetyl)-2,2-dimethyl-5-phenyl-;
Oxazolidine, 3-(dichloroacetyl)-2,2-dimethyl-5-(2-furanyl)-;
Oxazolidine, 3-(dichloroacetyl)-2,2-dimethyl-5-(2-thienyl)-;
Pyridine, 3-[3-(dichloroacetyl)-2,2-dimethyl-5-oxazolidinyl]-;
4-(Dichloroacetyl)-1-oxa-4-azaspiro-(4,5)-decane;
4-(Dichloroacetyl)-3,4-dihydro-3-methyl-2H-2,4-benzoxazine;

Ethanone, 2,2-dichloro-1-(1,2,3,4-tetrahydro-1-methyl-2-isoquinolinyl);
N-(Dichloroacetyl)-1,2,3,4-tetrahydroquinaldine;
1-(Dichloroacetyl)-1,2,3,4-tetrahydroquinoline;
Cis/trans-piperazine, 1,4-bis(dichloro-1,4-acetyl)-2,5-dimethyl-;
1,5-Diazacyclononane, 1,5-bis-(dichloroacetyl;
1-Azaspiro[4,4]nonane, 1-(dichloroacetyl);
Pyrrolo[1,2-a]-pyrimidine-[6(2H)]-one, 1-(dichloroacetyl-)hexahydro-3,3,8a-trimethyl]-;
2,2-Dimethyl-3-(dichloroacetyl)-1,3-oxazole;
2,2-Dimethyl-5-methoxy-3-(dichloroacetyl)-1,3-oxazole;
Phosphorothioic acid, O,O-diethyl O-(3-methylphenyl)ester;
α-[(Cyanomethoxy)imino]benzeneacetonitrile,
α-[(1,3-Dioxolan-2-yl-methoxy)imino]benzeneacetonitrile,
O-[1,3-Dioxolan-2-ylmethyl]-2,2,2-trifluoromethyl-4'-chloroacetophenone oxime,
Benzenemethamine, N-[4-(dichloromethylene]-1,3-dithiolan-2-ylidene] -α-methyl, hydrochloride,
Diphenylmethoxy acetic acid, methyl ester,
1,8-Naphthalic anhydride,
4,6-Dichloro-2-phenyl-pyrimidine,
2-Chloro-N-[1-(2,4,6-trimethylphenyl)ethenyl]acetamide,
Ethylene glycol acetal of 1,1-dichloroacetone,
1,3-Dioxolane, 2-(dichloromethyl)-2-methyl-,
5-Thiazolecarboxylic acid, 2-chloro-4-(trifluoromethyl)-, (phenylmethyl)-ester,
Phosphorothioic acid, O,O-diethyl O-(3-methylphenyl)ester,
4-Pentenenitrile, 2-methyl-2-[(4-methylphenyl)thio]-,
5-Chloro-8-(cyanomethoxy)quinoline,
1-Methylhexyl-2-(5-chloro-8-quinolinoxy)acetate,
O-(Methoxycarbonyl)-2-(8-quinolinoxy)acetamide oxime
5-Oxazolecarboxylic acid, 2-[(2,2-dimethylethyl)amino]-4-(trifluoromethyl)-, ethyl ester,
Allyl-N-methyldithiocarbanilate,
4-Isoxazolecarboxylic acid, 5-(2,4-dichlorophenyl)-, ethyl ester,
Pyrimidine, 4,6-dichloro-2-phenyl,
4-Pentenenitrile, 2-methyl-2-[(4-methylphenyl)thio]-,
Acetonitrile, [(5-chloro-8-quinolinyl)oxy]-,
Acetamide 2-(diphenylmethoxy)-N-methyl-,
Glycine, N-[bis(4-methoxyphenyl)-methyl]-, ethyl ester,
Glycines N-[bis(4-chlorophenyl)-methyl]-, ethyl ester,
Acetic acid, [(10,11-dihydro-5H-dibenzo[a,d]cyclohepten-5-yl)oxy]-, 1,1-dimethylethyl ester,
Ethanethioamide, 2-(diphenylmethoxy)-,
Acetic acid, (diphenylmethoxy)-, propyl esters
Acetic acid, (diphenylmethoxy)-, 2,2,2-trifluoroethyl ester,
Acetic acid, {phenyl[3-(trifluoro-methyl)phenyl]methoxy}-, 2-methyl-2-propanamine salt,
Acetic acid, (diphenylmethoxy)-, phenyl ester,
Ethanethioic acid, 2-(diphenylmethoxy)-, S-ethyl ester,
Acetic acid, (diphenylmethoxy-, 2-cyanoethyl ester,
Acetic acid, {phenyl[3-(trifluoro-methyl)phenyl]methoxy}-, 2,2,2-trifluoroethyl ester,
Acetic acid, (diphenylmethoxy)-, 2-propynyl ester,
Acetic acid, (diphenylmethoxy)-, 3-furanylmethyl ester,
Acetic acid, [bis(2,6-dimethylphenyl)-methoxy]-,
Acetic acid, (diphenylmethoxy)-, 3-nitrophenyl ester,
Acetic acid, }[bis(2,6-dimethyl-phenyl)]methoxy}-, ethyl ester,
Acetic acid, (diphenylmethoxy)-, 1-cyano-1-methylethyl ester,
5-Thiazolecarboxylic acid, 2-chloro-4-(trifluoromethyl)-, ethyl ester,
5-Thiazolecarboxylic acids butyl ester, 2-chloro-, 4-(trifluoromethyl)-,
5-Thiazolecarboxylic acid, 2-chloro-, hexyl ester, 4-(trifluoromethyl)-,
5-Thiazolecarboxylic acid, 2-chloro-4-(trifluoromethyl)-, octyl ester,
5-Thiazolecarboxylic acid, 2-chloro-4-(trifluoromethyl)-, phenyl ester,
5-Thiazolecarboxylic acid, 2-chloro-4-(trifluoromethyl)-,
5-Thiazolecarboxylic acid, 2-[bromo-4-(trifluoromethyl)]-, ethyl ester,
5-Thiazolecarboxylic acid, 2-iodo-4-(trifluoromethyl)-, ethyl ester,
5-Thiazolecarboxylic acid, 2-chloro-4-(trifluoromethyl)-, 1-methylethanamine salt,
Benzylamine-, (alpha-methyl-, N-4-(methyl)-1,3-dithiol-2-ylidene) hydrochloride,
pyridine, N-oxide, 2-(3,4,5,6-tetrachloro-2-pyridylthio-)-,
Acetic acid, [3,5-bis(trifluoromethyl)-phenoxy]-,
Propanamide, 2-chloro-N-[5-iodo-4-(trifluoromethyl)-2-thiazolyl]-,
Cyclopropanecarbonitrile, 1-[(3,4-dimethylphenyl)thio]-,
Propanenitrile, 3-[[2-(1,1-dimethyl-ethyl)phenyl]thio]-,
4-Pentenenitrile, 2-methyl-2-[[4-(1-methylethyl)phenyl]thio]-,
Ethanimidamide, N'-[(methoxycarbonyl)-oxo]-2-(8-quinolinyloxy)-,
1(3H)-Isobenzofuranone, 3-[2-(2,5-dimethoxyphenyl)-2-oxoethyl]-,
Acetic acid, 2-(diphenylmethoxy) sodium salt hemihydrate,
Acetic acid, 2-(diphenylmethoxy)-, or
Acetic acid, (diphenylmethoxy)-, 2-propanamine salt.

21. Method according to claim 20 wherein said herbicide is nicosulfuron, primisulfuron, DPX E9636, NC-311, NC-319 or XRD-498.

22. Method according to claim 21 wherein said orthophosphate insecticide is terbufos, chlorpyrifos, disulfoton or phorate.

23. Method according to claim 22 wherein said antidotal compound is dichlormid or PPG-1292.

24. Method for combatting negative synergism in crops induced by the interaction of the herbicide nicosulfuron, primisulfuron, DPX E9636, NC-311, NC-319, or XRD-498 and the insecticide phorate, terbufos or chlorpyrifos, which comprises treating said crops, in conjunction with said herbicide and said insecticide, with a sufficient amount of the antidotal compound dichlormid, R-29148, PPG-1292, AD-67, MON-7400 or MON-13900 to reduce or inhibit said negative synergism.

25. Method for combatting negative synergism in corn induced by the interaction of the herbicide nicosulfuron, primisulfuron, DPX E9636, NC-311, NC-319, or XRD-498 with the insecticide phorate, terbufos or chlorpyrifos, which comprises treating said corn, in conjunction with said herbicide and said insecticide, with a sufficient amount of dichlormid, R-29148, PPG-1292, AD-67, MON-7400 or MON-13900 to reduce or inhibit said negative synergism.

* * * * *